US011118006B1

(12) United States Patent
Tong et al.

(10) Patent No.: US 11,118,006 B1
(45) Date of Patent: Sep. 14, 2021

(54) METHOD FOR PRODUCING POLYLACTIC ACID

(71) Applicants: Nutrition & Health Research Institute, COFCO Corporation, Beijing (CN); COFCO (jilin) Bio-Chemical Technology Co., Ltd, Changchun (CN); Jilin COFCO Biomaterial Co., Ltd, Changchun (CN); COFCO Biotechnology Co., Ltd., Bengbu (CN)

(72) Inventors: Yi Tong, Beijing (CN); Yi Li, Beijing (CN); Bo Chen, Beijing (CN); Peng Chen, Ningbo (CN); Weiqiang Zhou, Beijing (CN); Zhigang Liu, Changchun (CN); Tai An, Beijing (CN); Xiaoyan Wang, Beijing (CN); Chao Peng, Beijing (CN); Kai Yang, Beijing (CN)

(73) Assignees: Nutrition & Health Research Institute, COFCO Corporation, Beijing (CN); COFCO (jilin) Bio-Chemical Technology Co., Ltd, Changchun (CN); Jilin COFCO Biomaterial Co., Ltd, Changchun (CN); COFCO Biotechnology Co., Ltd., Bengbu (CN)

( * ) Notice: Subject to any disclaimer, the term of this patent is extended or adjusted under 35 U.S.C. 154(b) by 0 days.

(21) Appl. No.: 17/138,233

(22) Filed: Dec. 30, 2020

(30) Foreign Application Priority Data

Jun. 28, 2020 (CN) .......................... 202010594402.4

(51) Int. Cl.
C08G 63/08 (2006.01)
C08G 63/78 (2006.01)

(52) U.S. Cl.
CPC ............ C08G 63/08 (2013.01); C08G 63/78 (2013.01)

(58) Field of Classification Search
CPC ..................................................... H01F 27/30
USPC ........................... 528/354; 336/122, 123, 124
See application file for complete search history.

(56) References Cited

U.S. PATENT DOCUMENTS

2005/0227099 A1* 10/2005 Hiruma ............... C08L 2666/18
428/480
2009/0018237 A1* 1/2009 Fujii ....................... C08L 67/04
523/201
2011/0263811 A1* 10/2011 Sawai .................... B01D 71/56
528/272
2013/0049484 A1* 2/2013 Weissentern ............ H02J 5/005
307/104
2013/0224813 A1* 8/2013 Weusthuis .............. C12R 1/645
435/135

FOREIGN PATENT DOCUMENTS

| CN | 1101325 A | 4/1995 |
|---|---|---|
| CN | 1159959 A | 9/1997 |
| CN | 1754897 A | 4/2006 |
| CN | 101880696 A | 11/2010 |
| CN | 102517346 A | 6/2012 |
| CN | 103819658 A | 5/2014 |
| CN | 103898780 A | 7/2014 |
| CN | 104494062 A | 4/2015 |
| CN | 104924593 A | 9/2015 |
| CN | 105238829 A | 1/2016 |
| CN | 205182213 U | 4/2016 |
| CN | 208161595 U | 11/2018 |
| CN | 109504630 A | 3/2019 |
| CN | 109536409 A | 3/2019 |
| CN | 109628339 A | 4/2019 |
| CN | 109694559 A | 4/2019 |
| CN | 110272858 A | 9/2019 |
| CN | 209957681 U | 1/2020 |
| CN | 210022060 U | 2/2020 |
| CN | 110904162 A | 3/2020 |

OTHER PUBLICATIONS

The translation of OA1 (202010451638.2; citing Antibiotic Production).
Zhao et al. Homofermentative Production of Pure L-lactic Acid by Genetic Engineered *Escherichia coli*. (2012).
Principles of Food Engineering, edited by GAO Fucheng, China Light Industry Press, p. 389-390, Printing Date Dec. 1998.

* cited by examiner

*Primary Examiner* — Terressa Boykin
(74) *Attorney, Agent, or Firm* — Volpe Koenig

(57) ABSTRACT

The present disclosure relates to the technical field of biotechnology and polymer synthesis, and discloses a method for producing polylactic acid, the method comprises the following steps: (i) inoculating a lactic acid fermentation strain into a lactic acid fermentation culture medium to perform a fermentation, so as to obtain a fermentation broth containing lactate; (ii) separating the fermentation broth to obtain a lactic acid; (iii) synthesizing a polymer-grade lactide by using the lactic acid as a raw material; (iv) subjecting the polymer-grade lactide to a polymerization reaction in a polymerization reaction device to obtain a polylactic acid. Through the above technical solution, the polylactic acid can be efficiently produced in the present disclosure.

16 Claims, 6 Drawing Sheets

METHOD FOR PRODUCING POLYLACTIC ACID

PRIORITY CLAIM & CROSS REFERENCE

The application claims priority to Chinese Application No. 202010594402.4, filed on Jun. 28, 2020, entitled "Method for producing polylactic acid", which is herein specifically and entirely incorporated by reference.

FIELD OF INVENTION

The present disclosure relates to the technical field of biology, in particular to a method for producing polylactic acid.

BACKGROUND

Under the global background of inhibiting plastic bags, the biodegradable bio-based materials have attracted increasing attention from the governments of all countries. By the end of 2020, China will take the lead to forbid and limit the production, sale and use of a portion of plastic products in a part of areas and fields. As a result, the global consumption of degradable polylactic acid (PLA) has been increasing year by year, the lactic acid and polylactic acid industries have started its blowout growth.

The polylactic acid is a polymer obtained by polymerization of lactic acid monomers with high optical purity serving as a main raw material. Lactic acid is classified into the levorotatory-form (L-form) and dextrorotatory-form (D-form) according to the optical rotation of its chemical structure, the L-lactic acid is the main existing form of lactic acid in nature, and the application of D-lactic acid in foods and beverages is limited because it is not metabolized in the human body. The key production mode of lactic acid is a microbial fermentation process, particularly the homofermentation which utilizes lactic acid bacteria as strains, the theoretical glucose-lactic acid conversion rate is 100%, namely, one molecule of glucose can generate two molecules of lactic acid through glycolysis, the fermentation process belongs to a facultative anaerobic or trace oxygen consumption state, the stirring rate and aeration level during the fermentation process are mild. The differences of the production conditions of the D-lactic acid and the L-lactic acid mainly reside in the strains and fermentation conditions, and the differences of the recovery and purification processes are not obvious.

In order to achieve the goals of increasing production, improving purity, reducing cost, improving benefit, enhancing thallus tolerance and the like during the process of producing lactic acid on a large scale by a microbial fermentation method, it is required to perform systematic optimization of upstream, midstream and downstream in bioengineering, such as strain transformation, substitution with cheap raw materials, enhancing production intensity, and optimizing the separation and extraction process, so as to continuously exploit the potentials from multiple sectors of the lactic acid production process and improve the production efficiency.

The polymerization process of the polymer-grade lactic acid raw material with high optical purity is relatively mature, the improvements are mainly orientated in the aspects of process parameters, product control, equipment upgrading and the like, such that the quality and efficiency improvement of the polylactic acid polymerization process are finally realized. The polymerization methods are divided into a one-step method of directly dehydrating and polycondensing lactic acid monomers, and a two-step method of initially dehydrating lactic acid to generate lactide and then subjecting the lactide to ring-opening polymerization to prepare polylactic acid. The two-step method does not produce by-product water during the ring-opening polymerization reaction, can accurately control the molecular weight of the polymerization reaction product to reach 100,000 or more, and can remove impurities and a small amount of racemic lactic acid in lactic acid raw materials during the preparation and purification of lactide, thereby improving the chemical purity and the optical purity.

However, each step in the current polylactic acid production process still has room for further improvement.

SUMMARY

The present disclosure aims to overcome the problems in the prior art and provide a method for producing polylactic acid.

In order to fulfill the above purpose, the present disclosure provides a method for producing polylactic acid, the method comprises the following steps:

(i) inoculating lactic acid fermentation strains into a lactic acid fermentation culture medium to perform a fermentation, so as to obtain a fermentation broth containing lactate (ion);

(ii) separating the fermentation broth to obtain a lactic acid;

(iii) synthesizing polymer-grade lactide by using the lactic acid as a raw material;

(iv) subjecting the polymer-grade lactide to a polymerization reaction in a polymerization reaction device to obtain a polylactic acid, wherein the polymerization reaction device comprises a polymerization reactor and a stirring component disposed in the flow channel of the polymerization reactor, the stirring component includes an electromagnetic winding mechanism and a magnetic induction element, the electromagnetic winding mechanism is configured to encircle around the inner wall of the polymerization reactor, the electromagnetic winding mechanism is disposed around the magnetic induction element and forms a clearance between the electromagnetic winding mechanism and the magnetic induction element, so that the magnetic induction element and the electromagnetic winding mechanism can generate an electromagnetic induction, thereby allow the magnetic induction element to carry out autorotation around its axis, thread grooves are formed on the magnetic induction element.

Through the aforementioned technical solution, the polylactic acid can be efficiently produced in the present disclosure, and in a preferred embodiment, each step can produce a desirable treatment effect.

BIOLOGICAL DEPOSITION

The *Lactobacillus rhamnosus* of the present disclosure with a CGMCC No. 19507 was deposited in China General Microbiological Culture Collection Center (CGMCC) (address: No. 3, Courtyard 1, Beichen West Road, Chaoyang District, Beijing; Institute of Microbiology, Chinese Academy of Sciences, zip code: 100101) on Mar. 25, 2020, and the accession number was CGMCC No. 19507.

The *Lactobacillus rhamnosus* of the present disclosure with a CGMCC No. 19508 was deposited in China General Microbiological Culture Collection Center (CGMCC) (address: No. 3, Courtyard 1, Beichen West Road, Chaoyang District, Beijing; Institute of Microbiology, Chinese Academy of Sciences, zip code: 100101) on Mar. 25, 2020, and the accession number was CGMCC No. 19508.

DESCRIPTION OF THE REFERENCE SIGNS

Figure 1:
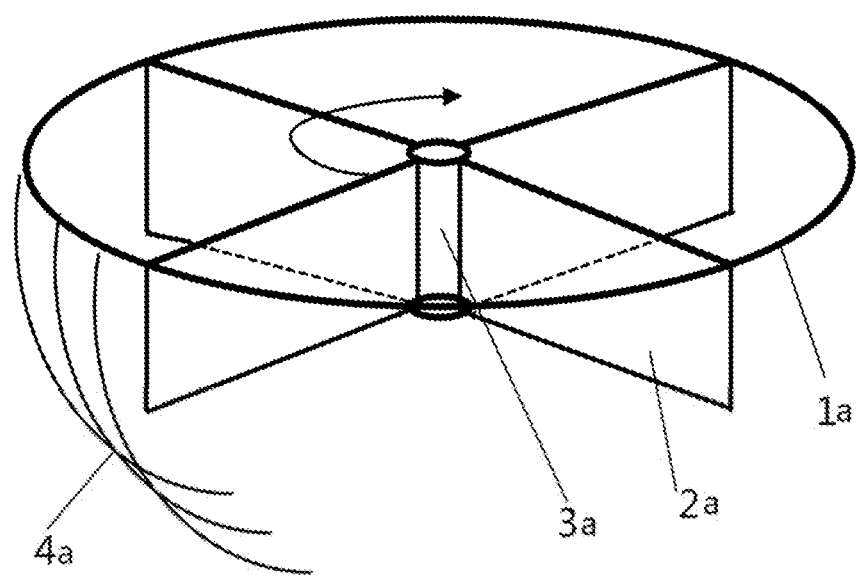
FIG. 1 illustrates a schematic view of the structure of a stirring apparatus according to an embodiment of the present disclosure.
Figure 2:
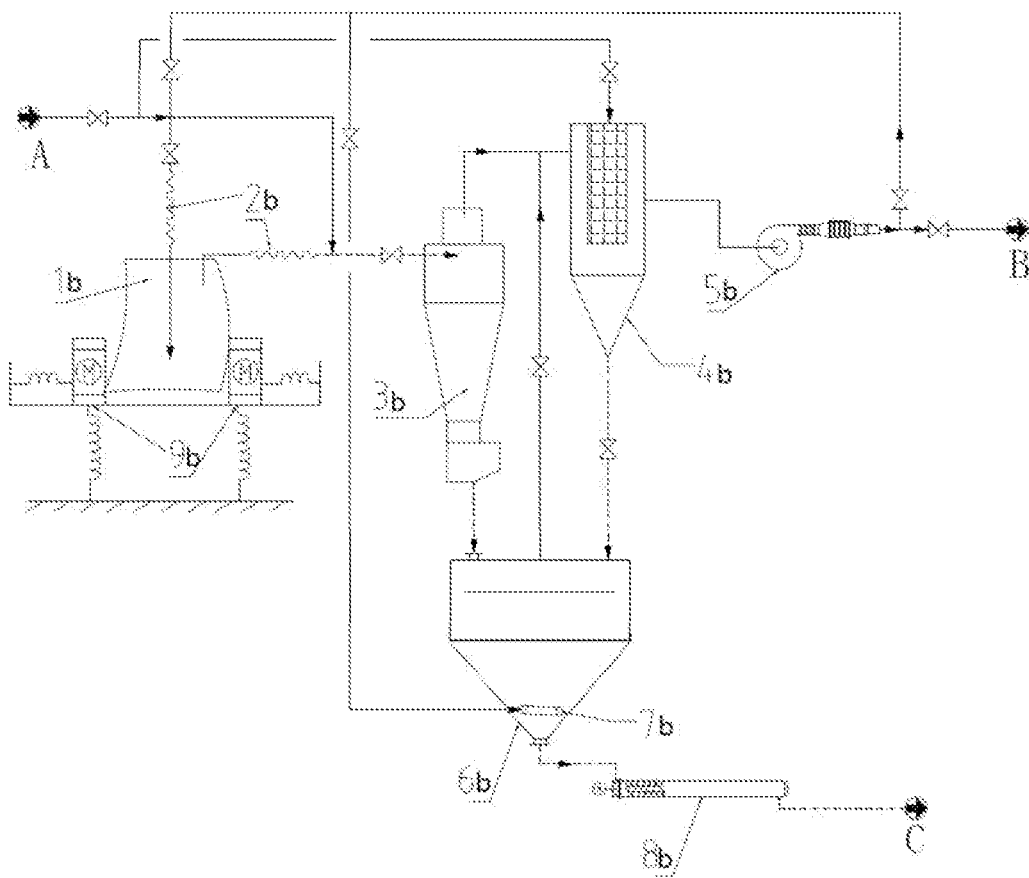
FIG. 2 illustrates a schematic view of the overall structure of an embodiment of the continuous feeding system for synthesizing polylactic acid from the air-insulated lactide according to the present disclosure.

In FIG. 1:
1a—Toroidal support; 2a—Blade; 3a—Shaft; 4a—Brush type strip
In FIG. 2:
1b—Raw material bag/box; 2b—Connection hose; 3b—Cyclone separator; 4b—Filter; 5b—Blower; 6b—Raw material collector; 7b—Gas distributor; 8b—Spiral conveyor; 9b—Vibration and extrusion crusher; A—Inert gas input pipeline; B—Air separation station; C—Reaction system
In FIGS. 3-4:
110—Polymerization reactor; 111—Melt feed inlet; 112—Melt discharge outlet; 120—Stirring component; 121—Magnetic induction element; 122—Coil rack; 123—Electromagnetic coil; 124—Magnetic isolation sleeve; 131—Circulation pipe fitting; 132—Static mixer; 133—Circulation pump; 140—Heat exchange liquid circulation cavity; 141—Heat exchange liquid inlet; 142—Heat exchange liquid outlet;
In FIG. 5:
I. Lactide melting tank; II. First polymerization reactor; III. Second polymerization reactor; IV. Demonomerization reactor; V. Twin-screw extruder
In FIGS. 6-7:
4-1. Electromagnetic vibration exciter; 4-2. Stirring drive motor; 4-3. Connecting shaft
4-4. Polylactic acid melt inlet; 4-5. Heat conduction oil inlet; 4-6. Heat conduction oil outlet;
4-7. Stirring driving device; 4-7-1. Stirring shaft; 4-7-2. Scraper
4-8. Lactide monomer outlet; 4-9. Polylactic acid finished product outlet
In FIG. 8:
1c. Motor
2c. Zone I of the twin-screw extruder
3c. Zones II to III of the twin-screw extruder
4c. Zone IV of the twin-screw extruder
5c. Zone V of the twin-screw extruder
6c. Zones VI to XI of the twin-screw extruder
7c. Headpiece of the twin-screw extruder
8c. First solid modifier hopper
9c. Second solid modifier hopper
10c. Polylactic acid melt feedstock metering pump
11c. First auxiliary material hopper
12c. Liquid feedstock metering pump
13c. Second auxiliary material hopper
14c. Polylactic acid melt pipeline
In FIGS. 9-10:
1. Feeding pipe
2. Distributor
3. Cylinder body
4. Clamp ferrule
5. Stirring shaft
6. Stirring belt
7. Steam condensate outlet pipe
8. Discharge pipe
9. Conical cylinder
10. Discharge port
11. Inert gas injection pipe
12. Support frame
13. Sealing cover
14. Steam inlet pipe
15. Material distribution port
16. Sealed gas injection pipe
17. Sealing filler
18. Sealing box
19. Connection rod
20. Support rod
21. Upper connection base
22. Heating spiral coil pipe
23. Liquid heating medium outlet pipe
24. Liquid heating medium inlet pipe
25. Lower connection base
26. Connection base exhaust hole
27. Stirring shaft exhaust hole

DETAILED DESCRIPTION

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

The present disclosure is based on one or more lactic acid fermentation strains, homotype fermentation is carried out under the facultative anaerobic condition, and the obtained fermentation broth is subjected to solid-liquid separation, decolorization and desalination treatment, and evaporation and concentration to obtain a lactic acid raw material with high purity and high-optical purity; based on lactic acid raw materials, lactic acid is subjected to condensation polymerization, purification of lactide and other processes to obtain a polymer-grade lactide, the polymer-grade lactide is subjected to polymerization process and demonomerization process to obtain a polylactic acid melt, the polylactic acid is subjected to direct melt spinning or chip spinning to produce polylactic acid fibers which are used for producing normal and profiled fibers. Therefore, the present disclosure provides a method for producing polylactic acid, it is characterized in that the method comprises:

(i) inoculating lactic acid fermentation strains into a lactic acid fermentation culture medium to perform a fermentation, so as to obtain a fermentation broth containing lactate;

(ii) separating the fermentation broth to obtain a lactic acid;

(iii) synthesizing polymer-grade lactide by using the lactic acid as a raw material;

(iv) subjecting the polymer-grade lactide to a polymerization reaction in a polymerization reaction device to obtain a polylactic acid.

Lactic Acid Fermentation Strain

The common lactic acid fermentation strains can be adopted, including *Lactobacillus plantarum, Lactobacillus rhamnous, Pediococcus acidilactici*, but not limited to wild strains, domesticated strains or genetically engineered strains, one or more of the strains are cultured in combination; preferably, the strain is a pentose domesticated *Pediococcus acidilactici* strain (such as *Pediococcus acidilactici* under accession number CGMCC No. 16833), *Lactobacillus plantarum* Lp-DA (CGMCC No. 16835), *Lactobacillus rhamnosus* Lr-ALHT (CGMCC No. 16834), *Lactobacillus rhamnosus* under accession number CGMCC No. 19507 or *Lactobacillus rhamnosus* under accession number CGMCC No. 19508.

The fermentation effect can be further improved and the yield and the optical purity of the L-lactic acid can be enhanced by using the *Lactobacillus rhamnosus* under accession number CGMCC No. 19507 or the *Lactobacillus rhamnosus* under accession number CGMCC No. 19508 as the lactic acid fermentation strain.

Before inoculating the lactic acid fermentation strain to the fermentation culture medium, the lactic acid fermentation strain may be initially activated, the specific manner of activation may be: inoculating the lactic acid fermentation strain frozen at low temperature into MRS liquid culture medium for activation culture under the temperature of 33-48° C. (preferably 37-42° C.) and a rotation speed of 150-200 r/min for overnight cultivation to obtain fresh seed solution.

Lactic Acid Fermentation Culture Medium

The lactic acid fermentation culture medium used in the present disclosure may comprise a carbon source, a nitrogen source and inorganic salts. The carbon source may be a carbon source consumed and utilized by lactic acid fermentation strains, it includes but not limited to glucose, starch sugar, molasses, glycerol, sucrose, cellulose hydrolysate, and other raw material or a combination thereof. The nitrogen source may be a nitrogen source consumed and utilized by lactic acid fermentation strains, it includes but not limited to yeast powder, yeast extract, corn steep liquor (powder), soybean meal hydrolysate, cottonseed protein and other raw material or a combination thereof. Preferably, the starch sugar is treated by pretreatment processes such as size mixing, liquefaction and saccharification, or a liquid phase obtained by crushing, sulfuric acid hydrolysis, steam explosion and cellulase enzymolysis. The inorganic salts may include buffer salts, trace elements and the like, preferably, phosphate buffer salts, sulfate salts or hydrochloride salts capable of providing $Mg^{2+}$, $Mn^{2+}$ and the like.

In order to expedite production of lactic acid, the lactic acid fermentation culture medium may further comprise a neutralizing agent, which is an alkaline substance capable of neutralizing lactic acid and maintaining the pH of the fermentation broth, including but not limited to calcium carbonate, sodium hydroxide, ammonia, sodium citrate and other substance which exhibits alkalinity upon hydrolysis or a combination thereof, preferably ammonia or sodium citrate, wherein the salts of strong alkali and weak acid such as sodium citrate can provide additional carbon elements for growth or acid production while performing a neutralizing effect.

Fermentation Process

In the present disclosure, the fermentation conditions may comprise: inoculating seed solution of freshly cultured lactic acid fermentation strains according to an inoculation amount of 1-10 vol %, controlling the temperature in the fermentation process to be generally within a range of 33-48° C., preferably 37-42° C., controlling the fermentation rotation speed to be 100-300 r/min, preferably 150-250 r/min, controlling the openable trace aeration level to be 0.05-0.1 vvm, and controlling the pH to be within a range of 5.5-7, preferably 5.8-6.4. The stirring paddle used in the fermentation is a stirring paddle capable of providing a desired mass transfer mixing effect, such as a six-flat-blade stirring paddle, a three-oblique-blade stirring paddle, a brush-type flat-blade stirring paddle, and preferably, a combination of the three-oblique-blade stirring paddle with the brush-type flat-blade stirring paddle in the upper and lower positions.

In order to overcome the problem that the existing stirring paddle cannot stir the precipitate, as shown in FIG. 1, the present disclosure provides a stirring device for a lactic acid fermentation tank, which comprises a stirring paddle body and a brush type strip 4a arranged to hang down from the stirring paddle body, such that the brush type strip 4a is rotatable along with the rotation of the stirring paddle body and contacts with the bottom of the lactic acid fermentation tank, the precipitate at the bottom of the lactic acid fermentation tank is swept and stirred by the brush type strip 4a.

The stirring device provided by the present disclosure can sweep and brush precipitate at the bottom of the lactic acid fermentation tank by utilizing the brush type strip, so that the mixing effect of insoluble solid substrates in a stirring state with low rotation speed can be improved. During the lactic acid fermentation process, the calcium carbonate and calcium lactate precipitates are deposited at the bottom of the fermentation tank, such that the mixing effect of the whole reaction system is reduced, and the neutralization capacity is negatively influenced. By means of the stirring device provided with the brush type strip, the insoluble calcium salt deposited at the bottom is scattered, the stable pH level inside the lactic acid fermentation tank is controlled, and the overall mixed mass transfer effect is enhanced under the premise that bubbles are broken.

Preferably, the stirring paddle body includes a shaft portion 3a and a paddle blade 2a disposed on a circumferential outer side of the shaft portion 3a. Most of the existing stirring paddles are a combination of inclined blade stirring paddles and flat blade stirring paddles, or flat blade stirring paddles, wherein the flat blade stirring paddles can effectively break bubbles to promote the transfer of oxygen, so that the radial mixing is obvious, but the axial mixing is insufficient; while the combination of inclined blade stirring paddles and flat blade stirring paddles provides the balanced axial and radial mixing, but its stirring effect on the insoluble substrate is weak. With respect to the stirring paddle of the present disclosure, the original disc is modified into a thin sleeve shape for connecting the rotating shaft, and the contact area between the paddle blade 2a and the mixed solution in the lactic acid fermentation tank is large under a slow stirring state, so that bubbles can be effectively scattered, the condition of uneven stirring of the central part of the lactic acid fermentation tank is avoided, and the reaction efficiency of the lactic acid fermentation tank is improved.

Preferably, the paddle blade 2a is formed in a flat plate shape, and an axis of the shaft portion 3a is parallel to a plate surface of the paddle blade 2a. Most of the existing stirring paddles are a combination of inclined blade stirring paddles and flat blade stirring paddles, or flat blade stirring paddles, and the flat blade stirring paddles can effectively break bubbles to promote the transfer of oxygen, so that the radial mixing is obvious, but the axial mixing is insufficient; while the combination of inclined blade and flat blade agitation provides balanced axial and radial mixing, but the stirring effect in regard to the insoluble substrate is weak. The paddle blade 2a of the present disclosure is a vertical paddle, and after being combined with the inclined blade paddle, the paddles can effectively break bubbles and blend the mixed liquid in an axial range and a radial range under the condition of a lower rotation speed.

Preferably, the stirring paddle body includes a circular ring-shaped support 1a, the circular ring-shaped support 1a is fixed at an upper end and an outside of a plurality of paddle blades 2a, the central axis of the circular ring-shaped support 1a is in coincidence with an axis of the shaft portion 3a. The circular ring-shaped support 1a is connected with the paddle blades 2a, so that the stability of the stirring device is further enhanced.

Preferably, the brush type strips 4a are uniformly spaced around the circumferential edge of the circular ring-shaped support 1a. There are limited positions between the vertically arranged paddle blades 2 which can be used for installation of the brush type strips 4a; if the paddle blades are directly disposed below the paddle blades 2, such an arrangement is not conducive to smashing of bubble; the circular ring-shaped support 1a allows the brush type strip to be evenly disposed at intervals, such that the brush type strips 4a clean the lactic acid fermentation tank bottom in a more even manner, also blend the mixed liquid in the lactic acid fermentation tank in a more uniform manner. Further, the installation modes of the brush type strips 4a comprise: the brush type strips 4a can be tied on a side surface of the circular ring-shaped support 1a; the upper end of the brush type strips 4a can be attached to the bottom of the circular ring-shaped support 1a.

Preferably, the paddle blades 2a have 3-8 blades uniformly arranged on the circumferential side surface of the shaft portion 3a. A plurality of uniformly arranged paddle blades can efficiently blend the mixed liquid in the lactic acid fermentation tank.

Preferably, 1-8 brush type strips 4a are arranged on the circular ring-shaped support 1a between the adjacent paddle blades 2a. The plurality of brush type strips 4a uniformly arranged on the circular ring-shaped support 1a improves the stirring efficiency of the mixed liquid in the lactic acid fermentation tank.

Preferably, the brush type strips 4a are polymeric plastic brush type strips. The high temperature-resistant and acid-resistant polymeric plastic brush type strips have enough toughness, and can contact with the bottom of the lactic acid fermentation tank like brushes in a static or stirring state, so as to improve the mixing degree of solid small particles in the mixed liquid in the lactic acid fermentation tank.

The present disclosure also provides a lactic acid fermentation tank, which comprises any one of the aforementioned stirring devices. The stirring device provided by the present disclosure can sweep and brush precipitates at the bottom of the lactic acid fermentation tank by utilizing the brush type strips, so that the mixing effect of insoluble solid substrates in a stirring state with a low rotation speed can be improved. During the lactic acid fermentation process, calcium carbonate and calcium lactate precipitate are deposited at the bottom of the fermentation tank, so that the mixing effect of the whole reaction system is reduced, and the neutralization capacity is negatively influenced. By means of the stirring device provided with the brush type strip, the insoluble calcium salt deposited at the bottom is scattered, the stable pH level inside the lactic acid fermentation tank is controlled, and the overall mixed mass transfer effect is enhanced under the premise that bubbles are broken.

Preferably, the lactic acid fermentation tank includes a reaction tank, the stirring device is disposed at the lower part of reaction tank, the bottom of reaction tank is further provided with a ring type gas distributor, the external diameter of stirring paddle body is larger than the external diameter of the ring type gas distributor. In the initial reaction stage of the mixed liquid in the lactic acid fermentation tank, air will be introduced into the mixed liquid in the lactic acid fermentation tank through the ring-type gas distributor, the introduced bubbles generally vertically rise due to buoyancy, and the outer diameter of the stirring paddle body is larger than the outer diameter of the ring-type gas distributor, which enables the introduced bubbles to be within the stirring range of the stirring paddle body, so as to improve the scattering efficiency of the bubbles, thereby increase the area of the mixed liquid contacting with the air in the lactic acid fermentation tank, and further improve the reaction efficiency of the lactic acid fermentation tank.

In order to overcome the problems of large air ventilation demand, high equipment investment, energy consumption and grain consumption in the fermentation and production process of the D-lactic acid, the present disclosure provides a specific embodiment and a method for preparing the D-lactic acid by fermentation, it is characterized that the method comprises the following steps: inoculating *Lactobacillus plantarum* into a fermentation culture medium to perform a lactic acid fermentation, wherein at least a part of a carbon source in the fermentation culture medium is provided by saccharified liquid (starch sugar). By adopting the technical solution, the D-lactic acid fermentation and production process can be performed with high sugar utilization rate and conversion rate, short production period, cheap raw materials and low production costs.

Wherein the starch sugar refers to a sugar prepared from starchy raw materials (grains and potatoes) by using an acid method, an acid enzymatic method or an enzymatic method. The maltose, glucose and high fructose syrup and the like are collectively called starch sugar.

The inventors of the present disclosure have discovered that the *Lactobacillus plantarum* under accession number CGMCC No. 16835 has strong stress resistance in the fermentation process, can tolerate larger range of pH and/or temperature fluctuation, and has loose fermentation conditions. In addition, the *Lactobacillus plantarum* has high utilization and conversion rate of the raw material starch sugar, short production period, is conducive to industrial production and promotion, and is particularly suitable for the method provided by the present disclosure.

Therefore, according to a preferred embodiment of the present disclosure, wherein the *Lactobacillus plantarum* is the *Lactobacillus plantarum* strain having an accession number of CGMCC No. 16835, which has been disclosed in CN109504630A.

According to a preferred embodiment of the present disclosure, wherein the dextrose equivalent (DE) value of the starch sugar is within a range of 95-99%.

According to a preferred embodiment of the present disclosure, in order to fulfill the purpose of fermentative production of D-lactic acid with the lowest raw material cost, the method further comprises the step of preparing starch sugar according to the following processes:

(1) mixing the slurry containing the starchy raw material with amylase for spray liquefaction, and then carrying out flash evaporation, cooling and heat preservation to obtain a liquefied liquid;

(2) blending the liquefied liquid with saccharifying enzyme and subjecting the mixture to saccharification to obtain a saccharified liquid.

According to a preferred embodiment of the present disclosure, the slurry containing the starchy raw material has a dry matter content of 30-50 wt % and a pH of 5.5-6.5. The dry matter content refers to that the test sample is dried at a specified temperature and time, and when the sample is dried to a constant weight, the percentage of the mass of the dried material relative to the mass of the sample before drying is the dry matter content.

Preferably, the starchy raw material may comprise a cereal material and/or a potato material.

More preferably, the starchy raw material is at least one selected from the group consisting of rice, corn, wheat, barley and sorghum.

According to the preferred embodiment of the present disclosure, the used amount of the amylase may be 100-220 U per kilogram of the starchy raw material in terms of dry matter.

More preferably, the amylase is used in an amount of 140-180 U.

According to a preferred embodiment of the present disclosure, the amylase may be any amylase commonly used in the art, as long as the purpose of hydrolyzing starch in a starchy raw material can be achieved.

Preferably, the amylase may include at least one of an alpha-amylase, a beta-amylase, and an isoamylase.

More preferably, wherein the amylase may be a combination of alpha-amylase, beta-amylase and isoamylase, so as to produce a favorable effect of starch hydrolysis.

Further preferably, the weight ratio of the alpha-amylase, beta-amylase and isoamylase may be 1:0.05-0.15:0.1-0.3, particularly preferably 1:0.08-0.12:0.18-0.22.

According to a preferred embodiment of the present disclosure, wherein the conditions of the spray liquefaction may include: the temperature is within a range of 100-120° C., and the time is 1-4 s.

According to a preferred embodiment of the present disclosure, wherein the conditions of the flash evaporation may include: the pressure difference is within a range of (−0.05) to (−0.1) MPa.

According to a preferable embodiment of the present disclosure, the temperature reduction is an operation of naturally reducing the temperature of the sprayed product by 5-10° C. after the flash evaporation so as to make the material reach the heat preservation temperature.

According to a preferred embodiment of the present disclosure, the heat preservation may be performed at 80-100° C. for 30-90 min. It serves to allow the saccharifying enzyme to react at an appropriate temperature.

According to a preferred embodiment of the present disclosure, the saccharifying enzyme is used in an amount of 800-4,000 U per kilogram of starchy raw material on a dry basis.

More preferably, the saccharifying enzyme is used in an amount of 1,000-2,000 U.

According to a preferred embodiment of the present disclosure, wherein the saccharification conditions comprise: the temperature is within a range of 55-65° C., the pH is 3-5, and the time is 20-26 h.

According to a preferred embodiment of the present disclosure, the used amount of starch sugar allows that the carbon content of the fermentation culture medium is within a range of 60-80 g/L.

According to a preferred embodiment of the present disclosure, wherein the nitrogen source in the fermentation culture medium is corn steep liquor. The dry matter content of the corn steep liquor is 5-45 wt %.

According to a preferred embodiment of the present disclosure, the fermentation culture medium may further contain inorganic salt. The inorganic salt may be used in an amount of 0.25-1 g/L.

More preferably, the inorganic salt may include a complex of phosphate, soluble magnesium salt and soluble manganese salt.

According to a preferred embodiment of the present disclosure, the used amount of the nitrogen source (particularly corn steep liquor) in the fermentation culture medium enables that the nitrogen content in the fermentation culture medium is within a range of 2-3.6 g/L.

According to a preferred embodiment of the present disclosure, wherein the lactic acid fermentation conditions may comprise: the temperature is within a range of 37-45° C., the pH is 5.3-6.5, the time is 40-60 h, the stirring speed is 50-150 rpm, and the inoculation amount of the *Lactobacillus plantarum* enables the biomass $OD_{600}$ after inoculation of the *Lactobacillus plantarum* to be 0.3-1 relative to the lactic acid fermentation system.

More preferably, the conditions of the lactic acid fermentation comprise: the temperature is within a range of 37-43° C., the pH is 5.5-6.3, the time is 40-55 h, and the stirring speed is 80-120 rpm. The inoculation amount of the *Lactobacillus plantarum* enables the biomass $OD_{600}$ after inoculation of the *Lactobacillus plantarum* to be 0.3-1 relative to the lactic acid fermentation system.

According to a preferred embodiment of the present disclosure, wherein the pH is adjusted during the fermentation by adding a proper amount of neutralizing agent into the fermentation system.

The inventors of the present disclosure have discovered in the research process that the lime milk has the characteristic of slow-release neutralization, thus the lime milk can be added in an one-off manner when being used as a neutralizing agent for lactic acid fermentation, and the proper acid-base environment of fermentation broth can be maintained without adding for multiple times or continuously feeding in the fermentation process. Therefore, the use of lime milk as a neutralizing agent can further simplify the lactic acid fermentation process.

According to a preferred embodiment of the present disclosure, wherein the neutralizing agent may be lime milk. The added amount of lime milk in terms of $Ca(OH)_2$ is 8-15 wt % (particularly preferably 10.5 wt %) relative to the weight of the lactic acid fermentation broth.

According to a preferred embodiment of the present disclosure, wherein the neutralizing agent may further include: one or more selected from the group consisting of sodium hydroxide, calcium carbonate, ammonia water, potassium citrate and sodium citrate. The addition mode is as follows: during the fermentation, the solution of said neutralizing agent with a concentration of 4-14 wt % is fed batch such that the pH of the fermentation system is maintained within a range of 5.3-6.5.

Preferably, the neutralizing agent is potassium citrate and/or sodium citrate.

The method of the present disclosure is particularly suitable for fermentative production of lactic acid at the medium-scale pilot plant or large-scale pilot production. The method is therefore preferably carried out in a fermentation tank having a volume of more than 50 L (in particular from 50 to 500 L).

In order to achieve the goal of low cost and high conversion rate of lactic acid production based on the huge productivity of cellulose, according to another embodiment of the present disclosure, there is provided a method for preparing lactic acid by fermentation, the method comprising: inoculating *Pediococcus acidilactici* into a fermentation culture medium, then introducing oxygen-containing gas into a fermentation system for pre-fermentation until the concentration of the *Pediococcus acidilactici* in the fermentation system reaches $OD_{600}$=8-13; and subsequently stopping introduction of the oxygen-containing gas, and continuing the fermentation process until the consumption of the five-carbon sugar (pentose) in a fermentation system reaches 45-55 wt %, wherein the fermentation culture medium before inoculation contains 30-100 g/L glucose and 15-45 g/L pentose, and the ventilation amount of the oxygen-containing gas is 0.005-0.05 vvm in terms of oxygen. By adopting the technical solution, the raw material cellulose with low price and huge productivity can be applied in the lactic acid fermentation production, so that the cost of the lactic acid fermentation production is reduced, and the method provided by the present disclosure can realize the lactic acid fermentation with low cost and high conversion in the small-scale pilot test and medium-scale pilot plant, and provides reference for the industrial scale lactic acid production process. The unit "vvm" refers to L/(L·min).

According to a preferred embodiment of the present disclosure, the *Pediococcus acidilactici* may be selected from the *Pediococcus acidilactici* with an accession number of CGMCC No. 16833. The *Pediococcus acidilactici* has been disclosed in CN109536409A.

Besides the ingredient pentose, the fermentation culture medium prior to the inoculation may contain 40-100 g/L glucose.

According to a preferred embodiment of the present disclosure, wherein the carbon source in the fermentation culture medium is provided by a cellulase enzymatic hydrolysate.

Preferably, the added amount of the cellulase enzymatic hydrolysate in the fermentation culture medium is 10-30 vol % based on the fermentation system.

More preferably, the cellulase enzymatic hydrolysate provides the fermentation culture medium with 25-50 g/L of carbon element.

According to a preferred embodiment of the present disclosure, wherein the pentose comprises xylose and/or arabinose. The pentose may be obtained by any conventional means in the art, for example by direct purchase of commercial products or by processing any pentose-containing feedstock.

According to a preferred embodiment of the present disclosure, the pentose is provided by a cellulose enzymatic hydrolysate, which is obtained by sequentially subjecting a cellulose raw material to acid hydrolysis, steam explosion, enzymatic hydrolysis and solid-liquid separation.

According to a preferred embodiment of the present disclosure, the cellulose raw material may be any cellulose raw material commonly used in the art.

Preferably, the cellulose raw material is at least one selected from the group consisting of straws, corn cobs, hardwoods, softwoods, fruit shells, grasses, papers, leaves, cottonseed lint, willow branches and oat hulls.

More preferably, the cellulose raw material is at least one selected from straws and oat hulls.

Wherein the straws may comprise any cellulose-containing crop straw, preferably at least one selected from the group consisting of corn straw, wheat straw, cotton straw, sorghum straw, and rice straw.

According to a preferred embodiment of the present disclosure, the acid hydrolysis method may be any acid hydrolysis method in the art as long as the purpose of loosening the lignocellulose structure and increasing the exposure degree can be achieved.

Preferably, the acid hydrolysis mode is as follows: the crushed cellulose raw material is contacted with a dilute sulfuric acid solution for a period of time, the obtained material is then dehydrated to obtain a wet material.

According to a preferred embodiment of the present disclosure, wherein the particle size of the pulverized cellulose raw material may be within a range of 10-100 mm. The concentration of the dilute sulfuric acid solution is 1-2 wt %. The weight ratio of the pulverized cellulose raw material relative to the dilute sulfuric acid solution is from 0.03-0.08:1. the contact time is more than 0.5 h, preferably 0.6-0.8 h.

According to the preferred embodiment of the present disclosure, the dehydration mode can be any dehydration mode commonly used in the technical field as long as the purpose of removing the moisture in the contacted materials is achieved.

Preferably, the dehydration mode can be extrusion dehydration. Its advantages reside in the simple equipment, reduced energy consumption and thorough one-off dewatering treatment.

According to a preferred embodiment of the present disclosure, wherein the purpose of steam explosion is to perform separation of the components of cellulose, hemicellulose and lignin.

Any steam explosion method commonly used in the art can be applied to the method provided by the present disclosure as long as the above purpose can be achieved.

Preferably, the steam explosion mode is as follows: placing the wet material in a sealed equipment for performing steam explosion treatment to obtain a steam explosion product. The steam explosion conditions include: the temperature of the saturated steam explosion treatment is within a range of 160-170° C., and the time is 40-60 min.

According to a preferred embodiment of the present disclosure, the enzymatic hydrolysis is performed by: contacting the steam explosion product with an enzyme.

Preferably, the enzyme is at least one selected from the group consisting of cellulase, hemicellulase, amylase, protease, glucoamylase and lipase.

More preferably, the amylase may include at least one of an alpha-amylase, a beta-amylase, and an isoamylase.

More preferably, the protease may include at least one of papain, pepsin and trypsin.

Further preferably, in order to ensure the enzymolysis effect, the cellulase may be a complex system consisting of cellobiase, hemicellulase and endoglucanase. The proportion of each enzyme can be adjusted according to the different characteristics of the cellulose raw material. For example, the Cellic CTec3 cellulase from Novozymes (China) Biotechnology Co., Ltd. may be selected as a commercially available enzyme.

Further preferably, in order to ensure the enzymolysis effect, the amylase can be a complex system consisting of alpha-amylase and beta-amylase. The proportion of each enzyme can be adjusted according to the different characteristics of the cellulose raw material. For example, a complex enzyme system prepared by mixing food-grade alpha-amylase and beta-amylase in Ningxia Sunson Industrial Group Co., Ltd. can be selected, and the mixing ratio is 1:0.15-0.25 (weight ratio).

Further preferably, in order to ensure the enzymolysis effect, the protease may be a mixture of papain, pepsin and trypsin. The proportion of each enzyme can be adjusted according to the different characteristics of the cellulose raw material. For example, the commercially available Protamax complex protease from Novozymes (China) Biotechnology Co., Ltd. may be selected.

According to a preferred embodiment of the present disclosure, wherein the solid-liquid separation is performed because the supernatant is used as a raw material of the fermentation culture medium, such that the burden of post-treatment can be alleviated, thereby reducing the post-treatment cost. Any conventional solid-liquid separation mode in the art is suitable for use in the process provided by the present disclosure.

Preferably, the solid-liquid separation mode comprises at least one of plate-and-frame filtration, centrifugal separation or natural sedimentation.

According to a preferred embodiment of the present disclosure, wherein the nitrogen source in the fermentation culture medium is provided by corn steep liquor.

Preferably, the corn steep liquor is added in an amount of 3-8 vol % based on the total volume of the fermentation culture medium.

More preferably, the corn steep liquor provides the fermentation culture medium with 0.8-2.3 g/L of nitrogen.

According to a preferred embodiment of the present disclosure, the fermentation culture medium may be further added with an inorganic salt as required. The inorganic salt serves to maintain osmotic pressure, and acts as an activating substance and the like for the functional protease.

Preferably, the inorganic salt may comprise phosphate, soluble magnesium salt and soluble manganese salt. The examples may be $KH_2PO_4$, $NaH_2PO_4$, $MgSO_4$, $MgCl_2$, $MnSO_4$, $MnCl_2$, and the like.

More preferably, the inorganic salt is added in an amount of 0.25-1 g/L.

According to a preferred embodiment of the present disclosure, the inoculation method of Pediococcus acidilactici may comprise: the Pediococcus acidilactici is prepared into a seed solution and then inoculated the seed solution into a culture medium.

Preferably, the preparation method of the seed solution comprises the following steps: inoculating the Pediococcus acidilactici strain frozen at low temperature into an activation culture medium for activation culture, and preparing a fresh seed solution after overnight cultivation. Wherein, the activation culture medium can be any culture medium which can recover the Pediococcus acidilactici strain frozen at low temperature. For example, it may be any one of MRS liquid culture medium and M17 culture medium. The conditions of the activation culture may include: the temperature is within a range of 33-48° C., and the rotation speed is 150-200 rpm.

More preferably, the concentration of Pediococcus acidilactici in the seed solution is $OD_{600}$=7-12.

Further preferably, the inoculation amount of the seed solution is 1-10 vol % based on the volume of the culture medium.

The inventors of the present disclosure have discovered that a proper amount of oxygen is introduced in the process of pre-fermentation, so that the amplification speed of the strain number can be accelerated, and the lactic acid fermentation period can be shortened.

According to a preferred embodiment of the present disclosure, the oxygen-containing gas may be any gas containing oxygen.

Preferably, for the sake of reducing costs and facilitating operation, the oxygen-containing gas is air.

More preferably, the introduced amount of the oxygen-containing gas is within a range of 0.005-0.05 vvm in terms of oxygen.

According to a preferred embodiment of the present disclosure, wherein the conditions of the pre-fermentation comprise: the temperature is within a range of 35-48° C., the pH is 5.3-6.5, the time is 10-30 h, and the stirring speed is 50-200 rpm.

More preferably, the conditions of the pre-fermentation comprise: the temperature is within a range of 37-45° C., the pH is 5.5-6.2, the time is 15-25 h, and the stirring speed is 70-150 rpm.

The inventors of the present disclosure have found during the research process that the yield of lactic acid in a certain period is maximized when the consumption of pentose in the culture medium reaches a specific range, the yield and production intensity of lactic acid are not improved by means of continuing the fermentation process. Therefore, in order to avoid the meaningless extension of the fermentation time, the fermentation process may be stopped when the consumption amount of pentose in the medium reaches a specific range, thereby shortening the fermentation period and improving the production efficiency.

According to a preferred embodiment of the present disclosure, the detection mode of the content of pentose in the fermentation culture medium is high performance liquid chromatography.

According to a preferred embodiment of the present disclosure, when the consumption amount of pentose in the fermentation system is within a range of 45-55 wt %, the lactic acid fermentation yield reaches the maximum, and the fermentation process may be stopped.

According to a preferred embodiment of the present disclosure, the conditions for the continuous fermentation and the conditions for the pre-fermentation may be the same or different. The conditions for continuous fermentation comprise: the temperature is within a range of 37-45° C., the pH is 5.3-6.5, the time is 30-50 h, and the stirring speed is 50-200 rpm.

More preferably, the conditions for continuous fermentation comprise: the temperature is within a range of 37-45° C., the pH is 5.7-6.2, the time is 35-45 h, and the stirring speed is 70-150 rpm.

According to a preferred embodiment of the present disclosure, wherein the pH during the pre-fermentation and/or fermentation process is adjusted by means of adding a neutralizing agent. According to a preferred embodiment of the present disclosure, the neutralizing agent comprises at least one selected from the group consisting of lime milk, sodium hydroxide, calcium carbonate, ammonia water, potassium citrate and sodium citrate.

Preferably, the neutralizing agent is potassium citrate and/or sodium citrate. The inventors of the present disclosure have discovered during the research process that when potassium citrate and/or sodium citrate is used as a neutralizing agent, it has the advantages of adjusting the pH and supplementing a carbon source, such that the yield of lactic acid can be further improved.

According to a preferred embodiment of the present disclosure, wherein for the sake of maximizing cost reduction and improving sugar acid conversion rate, the method may comprise: inoculating *Pediococcus acidilactici* into a fermentation culture medium, then introducing oxygen-containing gas into a fermentation system for pre-fermentation until the concentration of the *Pediococcus acidilactici* in the fermentation system reaches $OD_{600}$=10-13; subsequently stopping introduction of the oxygen-containing gas, and continuing the fermentation process until the consumption amount of the pentose in the fermentation system reaches 48-53 wt %. Wherein the fermentation culture medium before inoculation contains 60-80 g/L glucose and 25-35 g/L pentose, and the aeration amount of the oxygen-containing gas is 0.008-0.05 vvm in terms of oxygen.

According to a preferred embodiment of the present disclosure, the method can achieve a glucose-lactic acid conversion rate of 80% or more at a medium-scale pilot test level. Wherein the medium-scale pilot test level is the level of lactic acid produced by fermentation with a fermentation tank of more than 100 L.

Preferably, the fermentation tank has characteristics of low shear, high mass transfer and high mixing.

Separation of Lactic Acid

The lactic acid can be separated from the fermentation broth by adopting the existing method, the method specifically comprises the steps of subjecting the fermentation broth to solid-liquid separation, decoloration and desalination treatment, and evaporation concentration on the fermentation broth, so as to produce a lactic acid product with a high purity and high optical purity.

The solid-liquid separation method includes but is not limited to centrifugation, plate-and-frame filtration, membrane filtration, and other separation methods, preferably the plate-and-frame filtration method, which is characterized in that a filter cake after filtration is treated by using a gas cap water washing method, a fermentation broth in the filter cake is top-blown by using a compressed air cap, and after the air top-blowing is finished, the filter cake is washed with purified water, so that residual lactic acid in the bacterial cells is washed out by leaching.

The decolorization method generally comprises but is not limited to decolorization by using one or two of activated carbon and diatomaceous earth.

The desalination method typically comprises the following steps: (1) passing the centrifugally decolorized feed liquid through an alkaline resin to remove most of anions in the feed liquid so as to obtain a feed liquid I; (2) passing the feed liquid I obtained in the step (1) through an acidic resin to remove most of cations and amino acids in the feed liquid.

The evaporation concentration method generally comprises two-step evaporation: (1) distilling under reduced pressure to remove most of water to obtain a feed liquid II; (2) performing molecular distillation on the feed liquid II to obtain a distillate, which is exactly the refined lactic acid.

It shall be noted that if lactic acid in the fermentation broth is present in the form of calcium lactate, the fermentation broth is initially acidified to convert calcium lactate into lactic acid, then the solid-liquid separation is performed to remove the thallus; if the lactic acid in the fermentation broth is presented in the form of ammonium lactate and/or sodium lactate, the solid-liquid separation can be directly performed, followed by acidification.

In order to overcome the problems that the process for separating the lactic acid is complex and the prepared lactic acid has low purity, the present disclosure provides a method for separating the lactic acid, the method comprises the following steps:

(1) subjecting a lactic acid-containing solution (such as a lactic acid-containing fermentation broth) to an ion exchange to obtain a lactic acid solution;

(2) carrying out vacuum concentration in regard to the lactic acid solution to obtain a lactic acid concentrated solution;

(3) performing molecular distillation of the lactic acid concentrated solution so as to prepare a refined lactic acid;

wherein the content of lactic acid in the lactic acid-containing solution is within a range of 5-30 wt %. Through the aforementioned technical solution, the present disclosure effectively combines ion exchange, vacuum concentration and molecular distillation in order to obtain a refined lactic acid from the lactic acid-containing solution; particularly, the molecular distillation is carried out by adopting a wiped film evaporator, so that the content of the lactic acid in the obtained refined lactic acid reaches 99 wt %, and the purity of the lactic acid is effectively improved. In addition, the method for separating the lactic acid provided by the present disclosure may simplify the process flow and is conducive to the industrial production.

In the present disclosure, the lactic acid-containing solution may be selected from a wide range, as long as the lactic acid content in the lactic acid-containing solution is 5-30 wt %. Preferably, the lactic acid-containing solution is a lactic acid fermentation broth. In general, the lactic acid fermentation broth is obtained by performing fermentation using the lactic acid fermentation strains.

As described above, it is preferable that the lactic acid fermentation strain is at least one selected from the group consisting of *Lactococcus*, *Lactobacillus*, *Bacillus* and *Rhizopus*, preferably *Lactobacillus*. Further preferably, the *Lactobacillus* is at least one selected from the group consisting of *Lactobacillus rhamnosus*, *Lactobacillus plantarum* and *Pediococcus acidilactici*, preferably *Lactobacillus rhamnosus*.

According to a preferred embodiment of the present disclosure, the lactic acid solution is the *Lactobacillus rhamnosus* fermentation broth, which has a lactic acid content of 5-30 wt % and an impurity content of 7.5-14.4 wt %, wherein the *Lactobacillus rhamnosus* is the *Lactobacillus rhamnosus* under accession number CGMCC No. 16834 (CN109628339A).

According to the present disclosure, it is preferable that the ion exchange is performed in an ion exchange system filled with ion exchange resin, wherein the ion exchange system is a conventional technical means in the art, and the details are not described in the present disclosure.

According to the present disclosure, the volume ratio of the lactic acid-containing solution to the ion exchange resin is 1: 1-10, preferably 1: 2-5. A use of the preferred volume ratio is more favorable for removing the content of impurities such as anions, cations, amino acids in the lactic acid-containing solution, such that the content of the impurities in the lactic acid solution is within a range of 3-7.5 wt %.

Preferably, the ion exchange resin is selected from an anion exchange resin and/or a cation exchange resin.

In the present disclosure, the types and sources of the anion exchange resin and the cation exchange resin can be selected from wide ranges, the anion exchange resin and the cation exchange resin are commercially available or can be produced by self; among them, the anion exchange resins are commercially available, for example, at least one of LSD296, LSA-700B, and D303; the cation exchange resins are commercially available, for example, at least one of LX-160, LX-732 resin, LX-D001 and LX-D151.

According to a preferred embodiment of the present disclosure, a fermentation broth of *Lactobacillus rhamnosus* (with a lactic acid content of 14.46 wt. %) is subjected to ion exchange with an anion exchange resin (concentration) in a volume ratio of 1:1-10 so as to obtain lactic acid solution with a content of impurities of 3-7.5 wt %.

According to a preferred embodiment of the present disclosure, a fermentation broth of *Lactobacillus rhamnosus* (with a lactic acid content of 11.75 wt. %) is subjected to ion exchange with a cation exchange resin (concentration) in a volume ratio of 1:1-10 to obtain lactic acid solution with a content of impurities of 3-7.5 wt %.

In the present disclosure, the method of vacuum concentration can be selected from a wide range, as long as most of water in the lactic acid solution is removed in order to obtain a lactic acid concentrated solution having a water content of 10-40 wt %. Preferably, the vacuum concentration is carried out in a rotary evaporator, a rising-film evaporator or a falling-film evaporator, preferably in a rotary evaporator.

According to the present disclosure, the content of lactic acid in the lactic acid concentrated solution in the step (2) is preferably 60-90 wt %, and more preferably 80-85 wt %; the content of water is preferably 10-40 wt %, and more preferably 15-20 wt %.

In the present disclosure, there is a wide selection range of the conditions for the vacuum concentration, the conditions for the vacuum concentration include: the temperature is within a range of 30-80° C., preferably 40-70° C., and the vacuum degree is 0.1-1 mbar, preferably 0.6-0.9 mbar. The adoption of preferable condition of vacuum concentration is more conducive to improving the content of lactic acid in the lactic acid concentrated solution.

In the present disclosure, the mode of molecular distillation can be selected from a wide range, as long as the lactic acid concentrated solution may be distilled to obtain a purified lactic acid with high-concentration. Preferably, the molecular distillation is carried out in a thin film evaporator, which is a wiped film evaporator. In the examples of the present disclosure, the molecular distillation was carried out in a wiped film evaporator, but the present disclosure is not limited thereto.

In the present disclosure, there is a wide selection of the conditions of the wiped film evaporator, and the conditions of the wiped film evaporator preferably comprise: the rotation speed of a scraper is within a range of 20-150 r/min, preferably 50-120 r/min; the internal temperature of the steam clamp ferrule is 80-200° C., preferably 100-180° C.; the vacuum degree is 0-1 mbar, preferably 0.01-0.5 mbar. If the preferable condition of the wiped film evaporator is adopted, it is more conducive to improving the content of the lactic acid in the refined lactic acid.

Unless otherwise specified in the present disclosure, the wiped film evaporator comprises a heating clamp ferrule, a built-in cold end material collector and a film scraper; preferably, an outlet of the heating medium is arranged on the outer side of the heating clamp ferrule, and an inlet of the heating medium is disposed at the outer side wall of the heating clamp ferrule; preferably, the top of the heating clamp ferrule is provided with an inlet of the lactic acid concentrated solution; preferably, the lactic acid concentrated solution enters the heating clamp ferrule for molecular distillation, and then flows downwards along the inner side wall of the heating clamp ferrule to enter a material collector, so as to obtain the refined lactic acid.

According to the present disclosure, the content of lactic acid in the refined lactic acid in the step (3) is preferably larger than 90 wt %, and more preferably 95-99 wt %.

According to the present disclosure, when the lactic acid-containing solution is a lactic acid fermentation broth, it is preferable that the method further comprises: the lactic acid fermentation broth is pretreated before the step (1), wherein the purpose of the pretreatment is to remove thalli and pigments in the lactic acid fermentation broth so as to increase the content of lactic acid in the refined lactic acid.

Preferably, the pre-treatment comprises: sequentially carrying out solid-liquid separation and decolorization in regard to the lactic acid fermentation broth, wherein the solid-liquid separation is preferably filtration, and the decolorization is to contact the lactic acid fermentation broth with a decolorizing agent.

According to a preferred embodiment of the present disclosure, the method further comprises: before the ion exchange of the lactic acid fermentation broth, the lactic acid fermentation broth is subjected to solid-liquid separation and decoloration sequentially, it is conducive to improving purity of the lactic acid and reducing the impurities.

According to the present disclosure, it is preferable that the decolorizing agent is selected from the group consisting of an oxidation decolorizing agent and/or an adsorption decolorizing agent, preferably an adsorption decolorizing agent; further preferably, the adsorption decolorizing agent is selected from activated carbon and/or diatomaceous earth, preferably activated carbon.

In order to solve the problems during the process of separating the thallus cells of the lactate fermentation broth with respect to serious waste and lower yield of lactate in the existing method for separating the thallus cells and the lactate, the present disclosure further provides a method for separating the lactate, the method comprises the following steps:

(A) subjecting the lactate fermentation broth and a filter aid to mixing and solid-liquid separation sequentially to obtain a first feed liquid and a filter cake;

(B) carrying out gas cap washing treatment in regard to the filter cake to obtain a second feed liquid;

(C) performing downstream treatment in regard to the mixed solution of the first feed liquid and the second feed liquid so as to prepare the lactic acid;

wherein the lactate is selected from ammonium lactate and/or sodium lactate. The method adopts the gas cap washing treatment, can greatly reduce the loss of the lactate in the solid-liquid separation process of the lactate fermentation broth, and improve yield of the lactate; the system for separating the lactate provided by the present disclosure is simple and practical, it does not need to increase equipment investment and reagent consumption, can reduce the operation difficulty and unit cost in the lactate production process; as compared with the prior art, the yield of the lactate is more than or equal to 90%.

In the present disclosure, the lactate fermentation broth can be selected from a wide range, as long as the lactate content of the lactate fermentation broth is between 50 and 300 g/L. Preferably, the lactate fermentation broth is obtained by fermentation using lactic acid fermentation strains, wherein the lactic acid fermentation strains are at least one selected from the group consisting of *Lactococcus lactis, Lactobacillus, Bacillus* and *Rhizopus*, preferably *Lactobacillus*.

Preferably, the *Lactobacillus* is at least one selected from the group consisting of *Lactobacillus rhamnosus, Lactobacillus plantarum* and *Pediococcus acidilactici*, preferably *Lactobacillus rhamnosus*.

According to a preferable embodiment of the present disclosure, the lactate fermentation broth is fermentation broth of *Lactobacillus rhamnosus*, the content of lactate is 50-300 g/L, wherein the *Lactobacillus rhamnosus* is the *Lactobacillus rhamnosus* under accession number CGMCC No. 16834 (CN109628339A).

In the present disclosure, for the sake of promoting solid-liquid separation of bacterial cells in the lactate fermentation broth, the lactate fermentation broth is mixed with a filter aid, the filter aid is at least one selected from the group consisting of diatomaceous earth, activated carbon and perlite, preferably perlite.

According to the present disclosure, it is preferable that the solid-to-liquid ratio of the filter aid to the lactate fermentation broth is (0.1-10): 100 g/L, wherein the solid-to-liquid ratio refers to the dosage of the filter aid is 0.1-10 g relative to 100 L of lactate fermentation broth. For example, the solid-to-liquid ratio may be 0.1:100 g/L, 0.3:100 g/L, 0.5:100 g/L, 1:100 g/L, 2:100 g/L, 3:100 g/L, 4:100 g/L, 5:100 g/L, 6:100 g/L, 8:100 g/L, 10:100 g/L and any intermediate value therebetween, further preferably (0.5-5): 100 g/L, more preferably (0.5-3): 100 g/L. The preferable solid-liquid ratio is adopted, so as to reduce loss amount of the lactate in the solid-liquid separation process of the thallus cells in the lactate fermentation broth, and increase yield of the lactate in the separation process.

In the present disclosure, there is a wide range of options for the mixing mode, as long as the lactate fermentation broth is mixed uniformly with the filter aid. Preferably, the mixing is performed in a manner selected from the paddle stirring and/or the frame stirring, and more preferably frame stirring.

Preferably, the mixing conditions comprise: the temperature is within a range of 0-40° C., further preferably 10-30° C., more preferably 15-25° C.; the rotation speed is within a range of 10-100 rpm, further preferably 30-80 rpm, and more preferably 40-60 rpm. The loss amount of the lactate in the solid-liquid separation process of the thallus cells in the lactate fermentation broth can be effectively reduced by adopting the preferable mixing conditions.

According to the present disclosure, it is preferable that the solid-liquid separation is filtration, and the present disclosure provides a wide selection range for the filtration mode, as long as a mixture of the lactate fermentation broth and a filter aid is subjected to solid-liquid separation to obtain a first feed liquid and a filter cake. In order to avoid loss of lactate in the mixture of lactate fermentation broth and filter aid in the thallus separation, it is preferred that the filtration is carried out in a plate-and-frame filter.

According to a preferred embodiment of the present disclosure, the filtration mode is to perform filtration along with stirring, i.e., the stirring is not interrupted during the filtration process. By adopting the filtering mode, the dissolution of the lactate in thalli of the lactate fermentation broth can be effectively promoted, thereby reducing the loss of the lactate.

Preferably, the filtration pressure is within a range of 0.05-0.5 MPa, for example, the filtration pressure may be 0.05 MPa, 0.1 MPa, 0.15 MPa, 0.2 MPa, 0.25 MPa, 0.3 MPa, 0.35 MPa, 0.4 MPa, 0.45 MPa, 0.5 MPa, and any intermediate value therebetween, further preferably 0.1-0.4 MPa, and more preferably 0.15-0.25 MPa.

According to the present disclosure, it is preferable that the gas cap water washing treatment process comprises: sequentially carrying out a first top blowing, a water washing and a second top blowing in regard to the filter cake, wherein the first top blowing is to carry out a first top blowing on the filter cake by using compressed air to obtain lactate permeate; the step of water washing is to soak and wash the filter cake after subjecting to the first top blowing with water to obtain lactate residual liquid; the second top blowing is to carry out the second top blowing on the filter cake after the water washing process by using compressed air to obtain a rinsing solution.

Unless otherwise specified in the present disclosure, the second feed liquid includes the lactate permeate, the lactate residual solution, and a rinsing solution; the lactate permeate is obtained by carrying out the first top blowing and blowing out lactate in the filter cake by using compressed air; the lactate residual liquid refers to the residual liquid of lactate in the thallus cells, which is obtained by soaking and washing the filter cake after finishing the first top blowing by using water; and the rinsing solution refers to an aqueous solution which is obtained by second top blowing out the lactate in the filter cake by using compressed air after the water washing process is finished.

In the present disclosure, the filter cake obtained by filtering the lactate fermentation broth is subjected to gas top blowing and water washing treatments, so as to avoid the problems that the filtering speed is reduced during the filtering process due to thalli accumulating on the surface of filter cloth, and the lactate yield is low because that the lactate is remained in liquid among thalli cells and in the liquid, and the lactate is lost along with the abandonment of the thalli cells.

According to the present disclosure, the pressure of the compressed gas is within a range of 0.05-0.3 MPa, preferably 0.1-0.3 MPa, more preferably 0.12-0.2 MPa.

Preferably, the time for water washing is within a range of 10-120 min, further preferably 30-90 min, and more preferably 40-80 min.

Unless otherwise specified in the present disclosure, the downstream treatment refers to concentration of a mixed solution of the first feed liquid and the second feed liquid, and it specifically refers to that the cations and anions are initially removed by ion exchange, and the moisture is then removed by molecular distillation, wherein the ion exchange and the molecular distillation are conventional technical means in the field, the present disclosure does not impose limitation thereto. It is understandable by those skilled in the art that the downstream treatment also includes performing acid treatment to convert lactate into lactic acid.

In the present disclosure, the above-mentioned separation method is performed such that the yield of obtained lactate is 90% or more, preferably 94% or more.

The present disclosure also provides a system for separating lactate, the system comprising: a filter unit, a gas top blowing and water washing unit, and a downstream treatment unit, which are sequentially communicated with each other;

the filtering unit comprises a mixing tank provided with a stirring device, a liquid booster pump, a plate-and-frame filter and a filtrate receiving tank;

the gas top blowing and water washing unit comprises an air compressor, a compressed air storage tank, a water storage tank and a water delivery pump.

According to the present disclosure, it is preferable that the filter cloth in the plate-and-frame filter is an acid-resistant filter cloth, further preferably, the mesh number of the filter cloth is within a range of 200-1,000 meshes, preferably 300-800 meshes, and more preferably 400-600 meshes.

In the present disclosure, the gas top blowing and water washing unit is adopted, so as to avoid the slow reduction of the filtering speed caused by the accumulation of the filter cake on the filter cloth during the filtering process of the lactate fermentation broth, in addition, it can avoid the reduced yield of lactate due to the liquid among thallus cells in the filter cake and the residual lactate in the thallus.

Preparation of Lactide and Polylactic Acid

Based on a lactic acid raw material, the raw material is fed in a non-contact oxygen-insulating manner, and the lactic acid is subjected to the processes such as condensation polymerization reaction, purification of lactide to obtain a polymer-grade lactide, which is then polymerized to obtain the polylactic acid.

The (polymer grade) lactide synthesized by using lactic acid as a raw material in the present disclosure preferably comprises:
 (1) under a first polymerization condition, carrying out a pre-condensation polymerization reaction in regard to lactic acid to obtain a lactic acid prepolymer with a polymerization degree less than 5 (it may be 2, 3 or 4) and a gas phase containing lactic acid;
 (2) subjecting the lactic acid prepolymer to a condensation polymerization reaction in a falling film reactor under a second polymerization condition to obtain a lactic acid oligomer with a polymerization degree less than 10 (it may be 5, 6, 7, 8, 9 or 10);
 (3) depolymerizing the lactic acid oligomer under the action of a catalyst to obtain a lactide-containing product.

In order to prepare polylactic acid through a polymerization reaction, as shown in FIG. 2, the present disclosure provides a continuous feeding system for synthesizing polylactic acid from lactide in an air-isolated manner, the continuous feeding system comprises a raw material bag/box (a raw material donor) 1b, and a raw material collector 6b for collecting and outputting lactide, wherein the raw material bag/box 1b is connected with an inert gas input pipeline A, and a discharge pipe is movably inserted into the raw material bag/box 1b, a cyclone separator 3b is connected with the downstream part of the discharge pipe, and a solid matter outlet of the cyclone separator 3b is connected with the raw material collector 6b. For convenience of movement, the inert gas input pipeline A and the discharge pipeline can adopt a connection hose 2b, and the connection hose can be selected in practical application according to requirements. That is, the dry inert gas is introduced into a closed space of a raw material bag/box 1b containing a lactide raw material through an inert gas input pipeline A in the present disclosure, such that the lactide raw material and the dry inert gas form a gas-solid mixture, the lactide raw material is pneumatically output by the inert gas, the output gas-solid mixture is subjected to gas-solid separation by a cyclone separator 3b, and the separated lactide raw material is collected in a raw material collector 6b. According to the above content in the present disclosure, the raw materials are continuously fed under the condition of isolating air and moisture, the inert gas is used as the propelling power and the protective agent, the reaction conversion rate and the purity of the final product are high, the loss is less, and the manpower and material resources are saved. The nitrogen is usually used as the inert gas in practical applications.

In order to reduce the loss of lactide raw material, a small amount of solid matter mixed in the gaseous matter separated by the cyclone separator 3b is further separated and collected, the gaseous matter outlet of the cyclone separator 3b is connected with a filter 4b, and the solid matter outlet of the filter 4b is connected with the raw material collector 6b. For the sake of facilitate collection of the gaseous substances separated from the cyclone separator 3b, the filter 4b in the embodiment is a cloth bag filter, the shape and structure of the filter 4b can be selected according to requirements in practical applications. In order to keep the lactide raw material in a state of isolation from air and moisture all the time, the inert gas input pipeline A is directly connected with the filter 4b so as to conveniently purge the materials in the filter 4b.

In order to recycle the gas used as the conveying power in the continuous feeding system for synthesizing polylactic acid from air-insulated lactide and improve the fluidity of the gas in the circulation process, the gaseous substance outlet of the filter 4b is provided with a blower 5b, and the outlet of the blower 5b comprises two branches, wherein one branch is connected with the inert gas input pipeline A, and the other branch is connected with an air separation station B arranged outside the continuous feeding system for synthesizing polylactic acid from air-insulated lactide. That is, the gas output after gas-solid separation in the cyclone separator 3b is introduced into the filter 4b and subjected to filtering, and the filtered lactide raw material solid is collected in the raw material collector 6b; a part of inert gas in the filtered gas is returned to the inert gas input pipeline A, and the part of inert gas is conveyed to the raw material bag/box 1b again to form the recycling of the inert gas in the continuous feeding system for synthesizing the polylactic acid from the air-insulated lactide; and the other part of the inert gas is output for further recovery treatment, for example, in an example of the present disclosure, the other part of the inert gas is output to the air separation station B for recycling treatment, and the two parts of the inert gas are distributed according to a certain proportion.

In order to prevent the lactide raw material collected in the raw material collector 6b from gathering and adhering to form blocks, the raw material collector 6b is provided with a gas distributor 7b for loosening solid substances contained in the raw material collector, the gas distributor 7b is directly connected with an inert gas input pipeline A, and the collected lactide is loosened by using the inert gas.

For the sake of facilitating transportation, the outlet of the raw material collector 6b is connected with a spiral conveyor 8b, and the outlet of the spiral conveyor 8b is connected with a reaction system C arranged outside of the continuous feeding system for synthesizing polylactic acid from air-insulated lactide.

Typically, the inert gas may be nitrogen, argon or helium. In view of reducing cost and facilitating operation, nitrogen is used in the embodiment.

In addition, the structure of the raw material bag/box 1b may be fabricated with various forms as required, such as it may be a closed box body or a bag body, and a closed box body is adopted in the embodiment. Because the lactide raw materials maybe packed with boxes or bags, thus the nitrogen pipeline and lactide discharge conveying pipeline can be connected by the hose, in view of the coupling hose is more conducive to removal, regardless of what kind of structural form of the packing, the pneumatic conveying of the lactide raw materials can be performed by means of inserting the hose into the packing box or packing bag. Furthermore, in order to prevent the raw material package of the lactide raw material from being affected by the agglomeration due to moisture, a vibration and extrusion crusher 9b can be arranged outside the raw material bag/box 1b, the agglomerated lactide raw material due to moisture is sufficiently subjected to material extrusion and vibration before start of the feeding process, and the lactide raw material agglomerated in the raw material package is sufficiently broken up.

As shown in FIG. 2, The present disclosure also provides a feeding method of the continuous feeding system for synthesizing the polylactic acid from the air-insulated lactide, the method comprises the following steps:

Step 100: introducing dry inert gas into a closed space containing lactide raw materials, such that the lactide raw materials and the dry inert gas form a gas-solid mixture, wherein the lactide raw materials are pneumatically output by virtue of the inert gas;

Step 200: subjecting the output gas-solid mixture to a gas-solid separation, collecting the separated lactide raw material and outputting it to a reaction system arranged outside.

The moisture content in the dry inert gas in Step 100 is less than 15 ppm (v/v), and the oxygen content is less than 50 ppm (v/v).

In order to ensure that the lactide raw material is always in a state of insulation from air and moisture, the step 100 is preceded by: when the continuous feeding system for synthesizing the polylactic acid from the lactide in the air isolation manner is used for the first time, the dry inert gas is initially adopted to purge and replace the residual air in the whole feeding system until the content of the inert gas in the feeding system exceeds 99% (V).

In order to prevent the feeding from being affected by the agglomeration of the lactide raw material in the raw material package due to moisture, the step 100 preceded by: subjecting the lactide raw material to sufficient extrusion and vibration, such that the lactide raw material agglomerated in the raw material package is sufficiently broken up. The processing time of the material extrusion and vibration is within a range of 5-30 min, preferably 5-20 min.

In order to save energy and enable the inert gas to be repeatedly used in the whole feeding system, and form the circulation of the inert gas in the continuous feeding system for synthesizing the polylactic acid from the air-insulated lactide, in particular, the Step 200 further comprises the following processes: filtering the gas output after the gas-solid separation, and collecting the filtered lactide raw material solid; returning a part of inert gas in the filtered gas to the closed space containing the lactide raw material in the Step 100 so as to form the recycling of the inert gas in a continuous feeding system for synthesizing the polylactic acid from the lactide in an air-insulated manner; and the outputting other part of the inert gas for further recycling and treatment, for example, it can be output to an air separation station for recycling and treatment. More specifically, the distribution ratio of the part of the inert gas recycled and the other part of the inert gas output to the air separation station for recycling and treatment is within a range of 5:1-1:2, preferably 4:1-1:1.

It is required to periodically purge the collected lactide raw material with an inert gas; the periodic purging with the inert gas is performed once after completing each batch of feeding; the batch is defined as follows: when the feeding of 4-6 sealed packages of the lactic raw material is completed, it forms a batch.

Moreover, in order to prevent the collected lactide raw material from agglomeration thereby affect the solid material transportation, the Step 200 further comprises: carrying out inert gas blowing and loosening treatment in regard to the collected lactide raw material solid, wherein the time of blowing and loosening is within a range of 5-30 min, preferably 5-20 min.

Under the condition of ensuring complete isolation of air and moisture, the environmental temperature of the continuous feeding system for synthesizing the polylactic acid from the air-isolated lactide is within a range of 20-35° C.

Based on the above content, the present disclosure provides a continuous feeding system for synthesizing polylactic acid from air-insulated lactide, which uses an inert gas (e.g., nitrogen gas) as the propulsion power of lactide raw material transportation and the protective agent in the transfer process, the inert gas can isolate air and moisture from entering the system, ensure the purity of lactide, thereby improving the conversion rate of reaction and the purity of final products, and can avoid the loss of raw materials, reduce the generation of useless waste materials in the system, reduce manual operation and save manpower and material resources.

As illustrated in FIG. 2, the specific working process of the continuous feeding system for synthesizing polylactic acid from air-insulated lactide provided by the present disclosure is as follows:

The raw material bag/box 1b, which is hermetically packed with raw material lactide, is transferred to a raw material processing table and fixed, and in the embodiment shown in FIG. 2, the vibration and extrusion crusher 9b mainly includes a vibration mechanism, which may be generally selected as a vibration spring, provided at the raw material processing table. The raw material processing table is driven by a driving mechanism such as a motor to vibrate up and down, left and right in a unidirectional manner, or up and down, left and right in a combined manner, such that the agglomerated lactide raw material in the raw material package is fully broken up. Typically, the vibration and extrusion crusher 9b performs sufficient material extrusion and vibration on the lactide raw material for 5-30 min, preferably 5-20 min, for instance, the material in this example is extruded and vibrated for 10 min so as to sufficiently break up the agglomerated lactide raw material in the material package. The inert gas output from the inert gas input pipeline A is inserted into the bottom of the raw material bag/box 1b and communicated with the inside thereof through a movable inert gas input pipeline connected with a connection hose 2b, the inert gas adopted in the embodiment is nitrogen, meanwhile, one end of a movable raw material discharge pipe of the other connection hose is also inserted into the raw material bag/box 1b and communicated with the inside thereof, the other end of the raw material discharge pipe is communicated with the inside of the cyclone separator 3b, and a control valve for controlling the opening and closing of the pipeline is arranged on the raw material discharge pipe. In general, the input nitrogen gas is dry nitrogen gas having a moisture content of 15 ppm (v/v) or less and an oxygen content of 50 ppm (v/v) or less, and in this example, the moisture content is 10 ppm (v/v) and the oxygen content is 40 ppm (v/v).

It should be noted that, when the system is opened for the first time, the air in the whole system needs to be purged and replaced with fresh and dry nitrogen, and when the nitrogen content in the system exceeds 99% (V), the nitrogen pipe and the discharge pipe are inserted into the raw material bag/box 1b, and the blower 5b is simultaneously opened to pneumatically convey the lactide raw material.

Opening a nitrogen feeding valve on the nitrogen pipe, the nitrogen drives lactide to be conveyed to the cyclone separator 3b through the discharge pipe, separating the lactide and the nitrogen in the cyclone separator 3b, enabling the lactide to fall onto the bottom of the cyclone separator 3b, and the nitrogen flows from the top of the cyclone separator 3b to the filter 4b.

The lactide raw material falling onto the cyclone separator 3b enters a raw material collector 6b through a bottom discharge port, and is then is delivered to the reaction system C by a spiral conveyor 8b. The bottom of the raw material collector 6b is provided with a gas distributor 7b, nitrogen can be introduced to loosen the lactide raw material when the lactide raw material is blocked, so as to ensure smooth conveying of the raw material, the time of each loosening process is within a range of 5-30 min, preferably 5-20 min, for instance, the air supply and loosening process is 10 min in the embodiment. In addition, it is required to perform periodic purging with an inert gas on the lactide raw material collected in the raw material collector 6b, wherein the frequency of the periodic purging with an inert gas is performed once after completing each batch of feeding; wherein a batch is formed when the feeding of 4-6 sealed packages of the lactic raw material is completed, and the purging frequency can be selected according to the requirement in the practical operation process. In this example, the regular purging with nitrogen in regard to the lactide feedstock collected in the feedstock collector 6b is also performed by means of the gas distributor 7b.

The gas output after the gas-solid separation is filtered by a filter 4b, and the filtered lactide raw material solid is collected in a raw material collector 6b; a part of the filtered nitrogen returns to the raw material bag/box 1b to form the recycling of the nitrogen in the continuous feeding system for synthesizing the polylactic acid from the air-isolated lactide; and the other part of nitrogen is output to the air separation station B for recycling treatment. In general, the distribution ratio of one part of nitrogen gas relative to the other part of nitrogen gas is within a range of 5:1-1:2, preferably: 4:1-1:1. In the embodiment, the lactide raw material carried by nitrogen entering the filter 4b is collected in the filter 4B, after the nitrogen is pumped out by the blower 5b, 80% (V) of the nitrogen is returned to the nitrogen pipeline at the raw material bag/box 1b to replace fresh nitrogen for pneumatic conveying of lactide raw material, and the remaining 20% (V) of the nitrogen is sent to the air separation station B for performing regeneration treatment. That is, the distribution ratio of a part of nitrogen gas to another part of nitrogen gas in the embodiment is 4:1.

In the above feeding process, the ambient temperature of the continuous feeding system for synthesizing the polylactic acid from the air-isolated lactide is within a range of 20-35° C., for instance, the ambient temperature is 25° C. in the example.

According to the specific working process of the continuous feeding system for synthesizing polylactic acid from air-insulated lactide provided by the present disclosure, in the example shown in FIG. 2, only a small part of fresh nitrogen needs to be supplemented in each operation process of the whole system, and most of the nitrogen can be recycled, so as to save the energy consumption. In addition, the whole system is sealed without contact with air, so that the purity of the lactide raw material can be ensured, and the loss of raw material is avoided.

After the feeding system, the polylactic acid is synthesized by using lactide as a raw material and applying the following process, and the whole reaction process for synthesizing the polylactic acid is carried out under the protection of high vacuum or nitrogen, the process specifically comprises the following steps:

(a) conveying lactide into a lactide melting tank through a screw feeder under the protection of nitrogen and carry out melting treatment so as to obtain the molten lactide, wherein the melting temperature is within a range of 90-110° C., and the reaction time is 1-1.2 h;

(b) In the presence of a catalyst and an initiator, subjecting the molten lactide and the composite stabilizer to a first polymerization reaction in a first polymerization reaction device to obtain a first melt, wherein the reaction temperature is within a range of 140-160° C.; the pressure is 50-53 kPa, and the reaction time is 3-3.2 h;

(c) introducing the first melt into a second polymerization reaction device to carry out a second polymerization reaction so as to obtain a second melt; the reaction temperature is within a range of 170-200° C., the pressure is 6-6.5 MPa, and the reaction time is 1-1.2 h;

(d) introducing the second melt into a demonomerization reactor for carrying out the demonomerization reaction; the temperature is within a range of 210-215° C., the pressure is 1-1.5 kPa, and the reaction time is 0.5-0.6 h; the stirring speed is 5-30 rpm;

(e) carrying out water-cooling pelletizing, dehydration, crystallization and drying treatment in regard to the polylactic acid melt obtained after the step (d) to finally prepare the polylactic acid resin, wherein the temperature of a pelletizer is 210° C.

The reaction conversion rate of the polylactic acid produced with the feeding system and the method provided by the present disclosure through the actual industrial production is high, and it can reach 97% or more; the obtained polylactic acid product has desirable color and luster, and the weight-average molecular weight is within a range of 130,000-250,000; the content of lactide monomer in the obtained polylactic acid is 0.7-2.0%; the melt index of the polylactic acid at 190° C. under a load of 2.16 kg is 6-27 g/10 min. Compared with the conditions of about 95% of reaction conversion rate and 2-5% of monomer content in the prior art, the method utilizes an inert gas as the propelling power and the protective agent, the inert gas can isolate air and moisture from entering a system, avoid deterioration of the lactide raw materials caused by moisture absorption and oxidation, and may improve the reaction conversion rate and the purity of final products, and achieve the reaction conversion rate 97%, and the monomer content in the final products can be reduced to 0.7-2.0%; moreover, the present disclosure may avoid the loss of raw materials, reduce the generation of useless waste materials in the system, reduce manpower and material resources due to simple operation, and is an industrialized continuous feeding mode.

Through above technical solution, the continuous feeding is carried out under the condition of isolating air and moisture, and nitrogen is used as a propelling power and a protective agent, so that the deterioration of the lactide raw material caused by moisture absorption and oxidation is avoided, the reaction conversion rate and the purity of a final product are improved, the reaction conversion rate can reach 97%, and the monomer content in the final product can be reduced to 0.7-2.0%; the method is simple to operate, saves manpower and material resources, and pertains to an industrialized continuous feeding mode.

The present disclosure relates to a polylactic acid polymerization reaction device, the device comprises a polymerization reactor 110 and a stirring component 120 arranged in a flow channel of the polymerization reactor 110, wherein the stirring component 120 comprises an electromagnetic winding mechanism and a magnetic induction element 121, the electromagnetic winding mechanism is arranged along the inner wall of the polymerization reactor 110 in a surrounding manner, the electromagnetic winding mechanism is arranged around the magnetic induction element 121, a gap is formed between the electromagnetic winding mechanism and the magnetic induction element 121, so that the magnetic induction element 121 and the electromagnetic winding mechanism can generate electromagnetic induction, the magnetic induction element 121 can rotate around its axis, and a thread groove is formed on the magnetic induction element 121.

Under the dynamic action of the pump element, the melt may enter the polymerization reactor 110 and is finally output from the polymerization reactor 110, a polymerization reaction is carried out under the conditions of temperature and pressure in the polymerization reactor, the stirring component 120 of the present application is arranged in the flow channel of the polymerization reactor 110, an electromagnetic induction can occur between the magnetic induction element 121 and the electromagnetic winding mechanism, such that the magnetic induction element 121 can be arranged between the electromagnetic windings; under the power-on state and the power-off state of the electromagnetic winding mechanism, the magnetic induction element 121 can rotate around its axis, because the melt needs to pass through the gap between the magnetic induction element 121 and the electromagnetic winding mechanism, and the surface of the magnetic induction element 121 is provided with a thread groove, the melt can be stirred by the magnetic induction element, and the melt can perform periodic axial pulsation in coordination with the flow pressure of the melt per se, thereby realizing periodic volume pulsation deformation transportation of the melt, the molecular weight uniformity is ensured, the residence time of the polylactic acid melt is shortened during the pulsating deformation extrusion process, and the material is not prone to decompose, so as to improve the effect of polymerization reaction and increase the conversion rate of the product.

Figure 3:
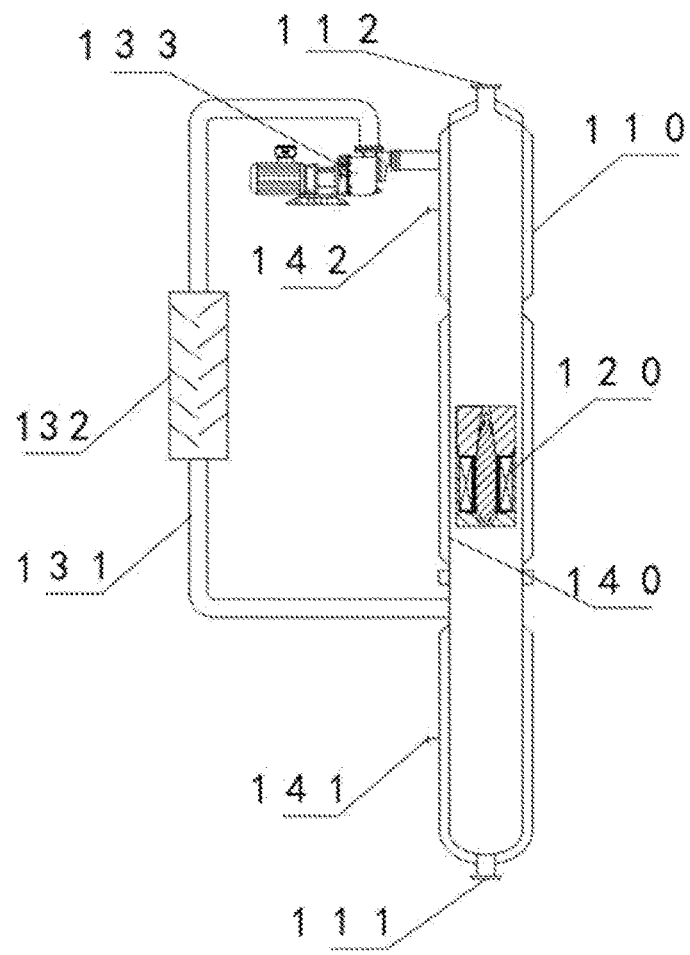
FIG. 3 illustrates a schematic view of a polylactic acid polymerization reaction device provided in accordance with a preferred embodiment of the present disclosure.

Wherein, as shown in FIG. 3, the polymerization reactor 110 is cylindrical and arranged along the vertical direction, an axis of the magnetic induction element 121 and an axis of the polymerization reactor 110 are collinear, the bottom of the polymerization reaction device is provided with a melt feed inlet 111, and the bottom of the melt feed inlet 111 is provided with a melt discharge port 112, in a preferred embodiment, the stirring component 120 is arranged at a position closer to the melt feed inlet 111 at the bottom, for example, the distance between the center of the stirring component 120 and the melt feed inlet 111 is set to be one third of the total length of the polymerization reactor 110.

A main shaft rod is arranged inside the polymerization reactor 110, the main shaft rod extends along the vertical direction, and the magnetic induction element 121 is sleeved on the main shaft rod. In a preferred embodiment, the magnetic induction element 121 is sleeved on the main shaft rod through a bearing, an inner ring of the bearing and the main shaft rod are formed with a connection form fixed by, for example, a bolt, an outer ring of the bearing can support the magnetic induction element 121, so that the magnetic induction element 121 is held in the annular electromagnetic winding mechanism; when the magnetic induction element 121 rotates, the magnetic induction element can rotate relative to the main shaft rod, that is, the magnetic induction element rotates while the main shaft rod does not move; in another preferred embodiment, a main shaft rod is rotatably disposed in the polymerization reactor 110, and the magnetic induction element 121 is fixedly disposed on the main shaft rod, such that the magnetic induction element 121 and the main shaft rod rotate together when the magnetic induction element 121 rotates.

Figure 4:
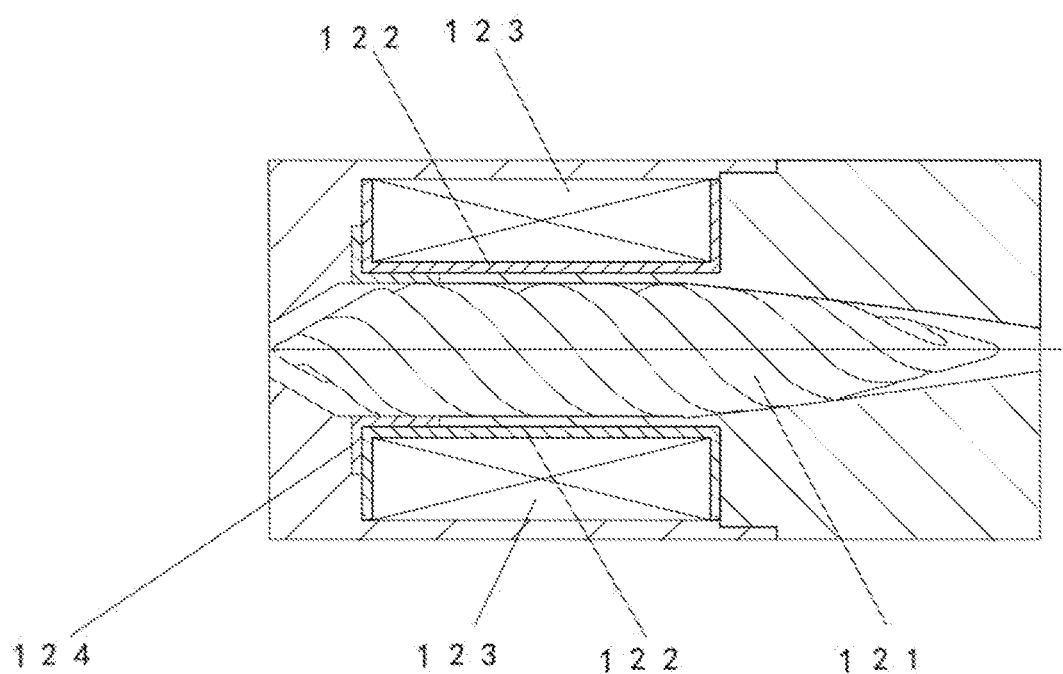
FIG. 4 illustrates a partial schematic view of the polylactic acid polymerization reaction device of FIG. 3, it shows the structure of a stirring component.
Figure 5:
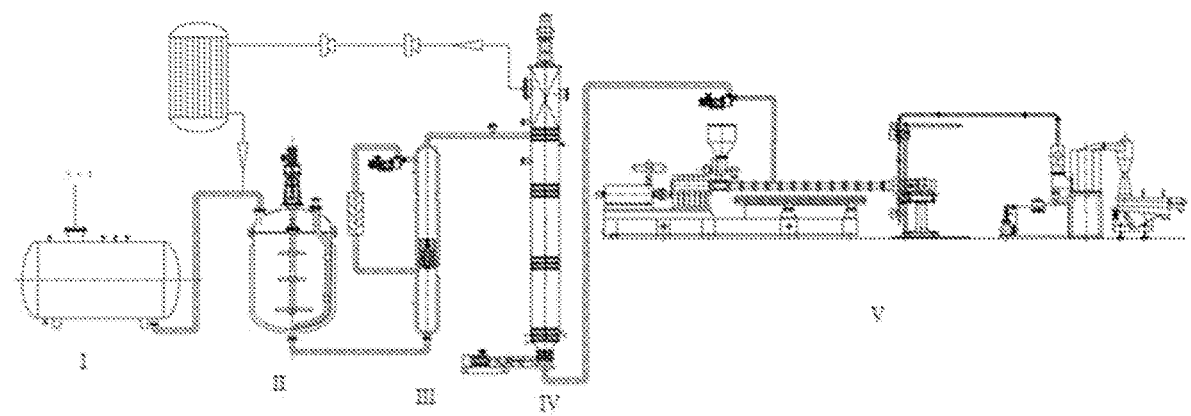
FIG. 5 illustrates a schematic view of an apparatus for producing polylactic acid according to the present disclosure.

As shown in FIG. 4, the electromagnetic winding mechanism includes a coil rack 122 and an electromagnetic coil 123 wound on the coil rack 122, wherein the coil rack 122 has a circular ring shape matched with the inner diameter of the polymerization reactor 110 and can be fixed on the inner wall of the polymerization reactor by means of bolt connection, screw fastening or an adhesive. The magnetic induction element 121 includes a main body portion and a tip portion that are sequentially arranged along the flow direction of the melt, the main body portion is cylindrical, the tip portion is tapered, the diameter of the tip portion along the flow direction of the solution is gradually reduced, and the tip portion is disposed to protrude from the electromagnetic winding mechanism. Wherein the cylindrical main body part enables the magnetic induction element 121 to sufficiently stir the melt passing through the gap when rotating, and the tip part protruding from the coil rack 122 can ensure the fluidity of the melt after being discharged from the gap. The magnetic induction element 121 is an integral part and made of an alloy material 38CrMoAl, and the magnetic induction element is a solid part.

An electric controller is arranged outside the polymerization reactor, the electric controller supplies power to the electromagnetic coil through electric wires and can control connection and disconnection of the electric circuit, the electric wires can penetrate through the shell of the polymerization reactor so as to be electrically connected with the electromagnetic coil; a conductive bolt can be arranged on the shell of the polymerization reactor and is used for supplying power to the electromagnetic coil in the polymerization reactor.

In addition, in order to avoid short circuit caused by direct contact between the magnetic induction element and the electromagnetic coil, a magnetic isolation sleeve 124 is further arranged on the outer side of the electromagnetic winding mechanism, the magnetic isolation sleeve 124 is located between the magnetic induction element 121 and the electromagnetic coil 123, the magnetic isolation sleeve is made of a high-permeability material having a magnetic permeability within a range of 80,000-350,000, and the magnetic isolation sleeve can be directly sleeved on the electromagnetic winding mechanism.

In order to ensure the heat exchange effect of the polymerization reactor, as shown in FIG. 3, the polymerization reactor 110 includes an outer shell and an inner shell, a heat exchange liquid circulation cavity 140 is formed between the outer shell and the inner shell, a heat exchange liquid inlet 141 and a heat exchange liquid outlet 142, which are communicated with the heat exchange liquid circulation cavity 140, are formed on the outer shell, and the stirring component 120 is disposed in the inner shell. Heat-exchange liquid can be introduced into the heat exchange liquid circulation cavity 140 through the heat exchange liquid inlet 141 and the heat exchange liquid outlet 142, so that the heat-exchange liquid can exchange heat with the melt in the inner shell, such that the temperature of the melt is increased.

More preferably, as shown in FIG. 3, the polylactic acid polymerization reaction device provided by the present application further comprises a circulation pipe fitting 131, and a static mixer 132 and a circulation pump 133 disposed on the circulation pipe fitting 131, wherein both ends of the circulation pipe fitting 131 are respectively in fluid communication with portions of the polymerization reactor 110 located at both sides of the stirring component 120. After a batch of melt enters the polymerization reactor 110 from the melt feed inlet 111, the melt feed inlet 111 is closed and the melt discharge outlet 112 is kept closed, in the meanwhile, under the action of the circulation pump 133, the melt can circularly flow between the polymerization reactor 110 and the circulating pipe fitting 131, and each circulation will pass through a static mixer 132, the inside of the static mixer is provided with a plurality of rectangular baffles which are alternately arranged, each rectangular baffle is provided with one or more through holes, for example, a circular hole with the diameter of 10 cm, so as to properly block the melt, and ensure the uniform mixing of the auxiliary agent and the melt, so that the mixing efficiency of the melt and the auxiliary agent is improved, and the polymerization effect is further enhanced.

The melt can flow on the polymerization reactor 110 and the circulating pipe fitting 131 in a plurality of circulations, the rotation direction of the magnetic induction element 121 can be controlled by controlling whether the electromagnetic winding mechanism of the stirring component is powered on, the rotation direction of the magnetic induction element 121 is just opposite under the power-on state and power-off state of the electromagnetic winding mechanism, and in use, the electromagnetic winding mechanism can be kept in a power-on state for a period of time and then kept a power-off state for a period of time, so that the melt can be stirred in different directions, so as to improve the polymerization reaction effect.

The molten lactide, a catalyst, an initiator and a high-efficiency composite stabilizer are introduced into the polymerization reactor, under the conditions consisting of a pressure of 6 MPa and a temperature of 190-200° C., for example, the reaction time of the melt between the polymerization reactor 110 and the circulating pipe fitting 131 is 3 hours, the current introduced to the stirring component in the energized state is 20-30A, the results in The table I is obtained by taking the times of power-on state and power-off state of the stirring component as the variables.

TABLE 1

| Current (I) | Power-on time (t) | Power-off time (t) | Polydispersity index (PDI) | Conversion rate (%) |
|---|---|---|---|---|
| 0A | 0 h | 3 h | 1.47 | 94.5 |
| 20A | 3 h | 0 h | 1.35 | 95 |
| 22A | 2.5 h | 0.5 h | 1.15 | 96.2 |
| 24A | 2 h | 1 h | 1.29 | 95.7 |
| 26A | 1.5 h | 1.5 h | 1.32 | 95.8 |
| 28A | 1 h | 2 h | 1.39 | 95.3 |
| 30A | 0.5 h | 2.5 h | 1.32 | 94.8 |
| Polylactic acid resin prepared with the conventional polymerization process | | | 1.56 | 93.6 |

As can be seen from Table I, the polydispersity index (PDI) of polylactic aid (PLA) slices produced using the polylactic acid polymerization reaction device provided by the present disclosure has a minimum of 1.15, while the PLA slices prepared with the conventional polymerization process has a PDI of 1.56.

The application also provides a polylactic acid polymerization reaction system, wherein the polylactic acid polymerization reaction system may carry out two polymerization reaction processes, the polylactic acid polymerization reaction device provided by the present application is used for the second polymerization reaction process of the system, wherein the melt obtained after the first polymerization reaction can enter the polymerization reactor 110 from the melt feed inlet 111, and is subjected to stirring treatment by the stirring component 120, and then output through the melt discharge outlet 112 and enters the downstream process to continuously carry out the demonomerization process and the granulation process. The polylactic acid polymerization reaction system provided by the present application can improve the effect of polymerization reaction, such that the conversion rate of a product is increased.

Through above technical solution, by utilizing the polylactic acid polymerization reaction device provided by the present application, under the power action of the pump element, the melt may enter the polymerization reactor and is finally output from the polymerization reactor, a polymerization reaction is carried out under the conditions of temperature and pressure in the polymerization reactor, the stirring component is arranged in the flow channel of the polymerization reactor, an electromagnetic induction can occur between the magnetic induction element and the electromagnetic winding mechanism, such that the magnetic induction element can be arranged between the electromagnetic windings; under the power-on state and the power-off state of the electromagnetic winding mechanism, the magnetic induction element can rotate around its axis, because the melt needs to pass through the gap between the magnetic induction element and the electromagnetic winding mechanism, and the surface of the magnetic induction element is provided with a thread groove, the melt can be stirred by the magnetic induction element, and the melt can perform periodic axial pulsation in coordination with the flow pressure of the melt per se, thereby realizing periodic volume pulsation deformation transportation of the melt, the molecular weight uniformity is ensured, the residence time of the polylactic acid melt is shortened during the pulsating deformation extrusion process, and the material is not prone to decompose, so as to improve the effect of polymerization reaction and increase the conversion rate of the product.

In order to prepare polylactic acid through a polymerization reaction, the present disclosure provides a device for producing polylactic acid, wherein the device comprises a lactide melting tank I, a first polymerization reactor II, a second polymerization reactor III and a demonomerization reactor IV which are connected in sequence; wherein the demonomerization reactor IV comprises an electromagnetic vibration exciter 4-1, a stirring drive motor 4-2 and a stirring driving device 4-7, the stirring drive motor 4-2 is connected with the stirring driving device 4-7 to regulate and control the stirring frequency of the stirring shaft 4-7-1, and the electromagnetic vibration exciter 4-1 is connected with the stirring drive motor 4-2 via a vibration transmission disc to enable the stirring drive motor 4-2 to vibrate axially.

Figure 7:
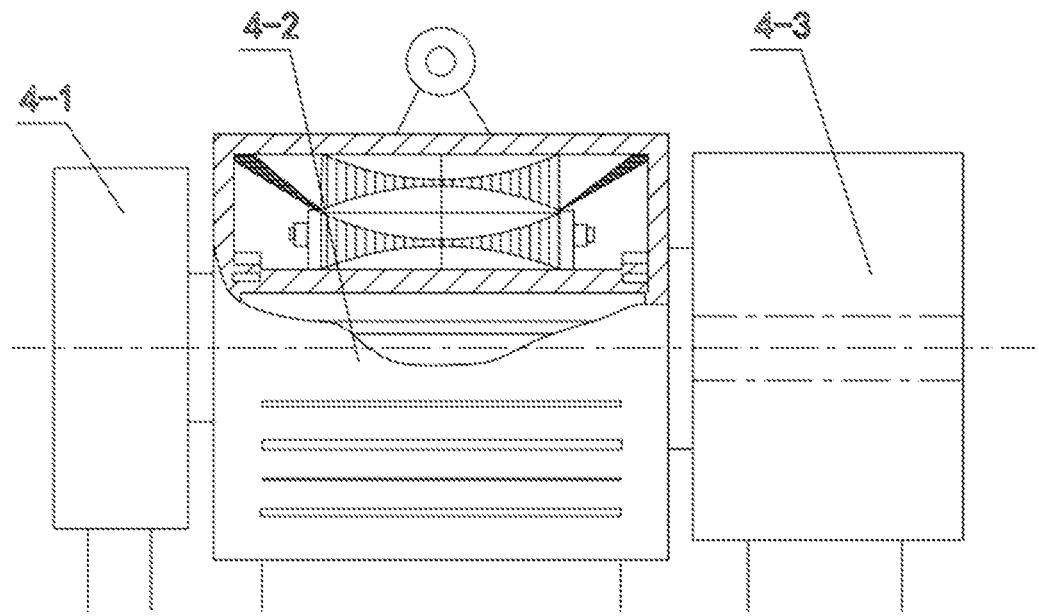
FIG. 7 illustrates a schematic view of the actuator in the demonomerization reactor IV of the present disclosure.

In the present disclosure, FIG. 7 illustrates a schematic diagram of a transmission device in a demonomerization reactor IV of the present disclosure, as shown in FIG. 7, in the demonomerization reactor IV, the electromagnetic vibration exciter 4-1 is sequentially connected with the stirring drive motor 4-2 and the connecting shaft 4-3, the electromagnetic vibration exciter 4-1 is connected with the stirring shaft 4-7-1 via a vibration transmission disc to axially vibrate the stirring shaft 4-7-1, the scraper 4-7-2 on the stirring shaft 4-7-1 also periodically changes along with the vibration of the stirring shaft 4-7-1, so as to introduce a vibration force field into a melt (for example, a second melt obtained after a second polymerization reaction) in the demonomerization reactor IV, furthermore, the shear rate of the melt also periodically varies along with the vibration force field, and the introduction of the vibration force field can improve the shear rate of the melt, so that the melt interface is stretched and compressed to generate the corresponding oscillation.

Figure 6:
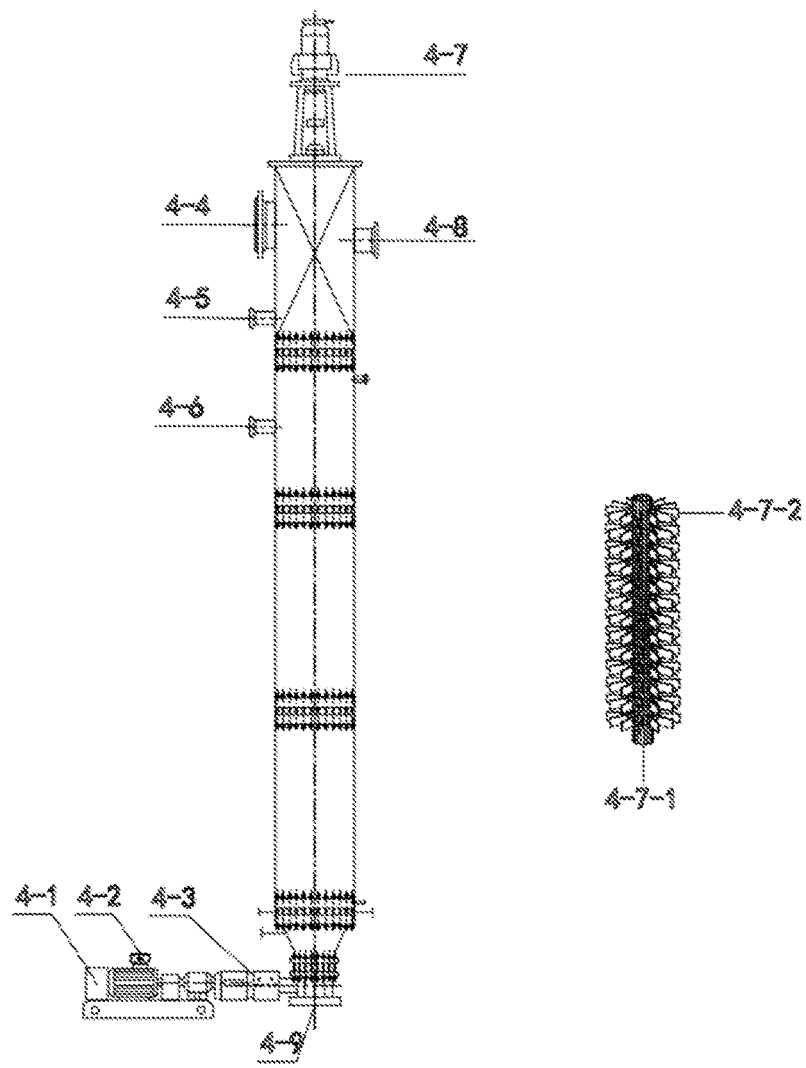
FIG. 6 illustrates a schematic view of a demonomerization reactor IV of the present disclosure.

FIG. 6 is a schematic view of a demonomerization reactor IV of the present disclosure, as shown in FIG. 6, the stirring shaft 4-7-1 is provided with a plurality of scrapers 4-7-2; preferably, the plurality of scrapers 4-7-2 are separately arranged with an angular interval of 36°-180° along the circumferential direction of said stirring shaft 4-7-1 on a horizontal plane centered on any point on said stirring shaft 4-7-1, specifically, the plurality of scrapers 4-7-2 maybe separately arranged with an angular interval of 36°, 72°, 108°, 144°, 180° along the circumferential direction of said stirring shaft 4-7-1; preferably, the plurality of said scrapers 4-7-2 are arranged in a stacked manner at an interval of 5-8 cm, preferably 5-6 cm, in the axial direction of said stirring shaft 4-7-1 on a vertical plane centered on said stirring shaft 4-7-1; the stirring shaft 4-7-1 is disposed in the demonomerization reactor IV, and in the monomer removing process, a new material is promoted to cover an old material on the surface through the rotation effect, so that the monomer in the main body of the polymer stays in a limited time, the overheating is prevented, and the repolymerization is avoided.

In addition, the distance between the outer edge of the scrapers 4-7-2 and the inner wall of the demonomerization reactor IV is preferably within a range of 1-3 cm, preferably 1-2 cm. In the present disclosure, the high viscosity melt of polylactic acid forms an uniform, ultra-thin film structure on the inner wall by means of the scrapers, the film structure provides a large enough surface area to fully volatilize the residual lactide monomer. In addition, it should be noted in the present disclosure that each of the scrapers 4-7-2 has two long sides and two short sides, one of the short sides is in contact with the stirring shaft 4-7-1, and the edge of the other short side is the "outer edge" of the scraper 4-7-2.

According to the present disclosure, the demonomerization reactor IV is further provided with a polylactic acid melt inlet 4-4, a heat conduction oil inlet 4-5, a heat conduction oil outlet 4-6, a lactide monomer outlet 4-8 and a polylactic acid finished product outlet 4-9.

According to the present disclosure, the second polymerization reactor III is internally provided with a stirring component 120.

Preferably, the stirring component 120 is an integrated structure consisting of a torpedo body with a spiral groove, a coil rack and an electromagnetic winding.

According to the present disclosure, FIG. 3 is a schematic view of a second polymerization reactor III of the present disclosure, as shown in FIG. 3, the second polymerization reactor III is further provided with a static mixer 132 and a circulation pump 133 connected with the static mixer 132, and the static mixer 132 is arranged to improve the mixing efficiency of the polymer melt and the auxiliary agent; in the present disclosure, the second polymerization reactor III is further provided with a melt feed inlet 111, a melt discharge outlet 112, a heat exchange liquid inlet 141 and a heat exchange liquid outlet 142.

According to the present disclosure, the first polymerization reactor II is internally provided with a stirring device, and the first polymerization reactor II is externally provided with a clamp ferrule.

According to the present disclosure, the device also comprises a twin-screw extruder V arranged in connection with the demonomerization reactor IV.

The present disclosure further provides a method for preparing polylactic acid from lactide, wherein the method is carried out in a device for preparing the polylactic acid, and comprises the following steps:

(a) carrying out melting treatment on lactide in a lactide melting tank I to obtain molten lactide;

(b) subjecting the molten lactide and the composite stabilizer to a first polymerization reaction in a first polymerization reactor II in the presence of a catalyst and an initiator, so as to obtain a first melt;

(c) introducing the first melt into a second polymerization reactor III to carry out a second polymerization reaction to obtain a second melt;

(d) introducing the second melt into a demonomerization reactor IV under the combined action of stirring conditions and exciting forces, so as to carry out the demonomerization reaction;

wherein the device is the aforementioned device.

FIG. 5 is a schematic view of an apparatus for preparing polylactic acid according to the present disclosure, and as shown in FIG. 5, the apparatus for preparing polylactic acid comprises a lactide melting tank I, a first polymerization reactor II, a second polymerization reactor III and a demonomerization reactor IV which are sequentially connected.

According to the present disclosure, the conditions of the melt processing in step (a) comprise: the temperature is within a range of 90-100° C., and the time is 1-1.2 h; preferably, the temperature is within a range of 90-95° C. and the time is 1-1.1 h. It is preferable in the present disclosure that the lactide is added to the lactide melting tank I under continuous protection of nitrogen; the lactide may be a racemic lactide, a meso-lactide, a levo-lactide or a dextro-lactide, in the present disclosure, the lactide is purchased from Total Corbion PLA (Thailand) Ltd., with a trade name Lumilact®L, a net weight 600 kg, a model number L85 and a purity of 99.5%.

According to the present disclosure, the catalyst in step (b) is stannous octoate. In the present disclosure, the catalyst defined by the present disclosure is selected, as the catalyst has the advantages of high conversion rate, less racemization phenomenon and high polymer molecular weight under the condition of higher monomer-catalyst ratio.

According to the present disclosure, the initiator is polyethylene glycol and/or isooctanol, preferably polyethylene glycol. In the present disclosure, the advantage of selecting the initiator polyethylene glycol defined in the present disclosure is that the polymerization of lactide starts from the terminal hydroxyl group of polyethylene glycol to produce the polyethylene glycol-polylactic acid two-block polymer, the polyethylene glycol produces shorter molecular chain during polymerization, low initiator content produces high polymer molecular weight, thereby obtaining a higher polymerization degree.

According to the present disclosure, in the first polymerization reaction, the inventors of the present disclosure have discovered that during the polymerization of polylactic acid, the polymerization is inevitably effects by factors such as heat, oxygen, mechanical shear during the polymerization process of PLA, a thermal degradation will occur, so that the melt viscosity is lowered, causing a reduction in the physical properties of the final product. In addition, an oxidative degradation is also generated in the polymerization process, the oxidative degradation is an auto-oxidative chain reaction with the processes of chain initiation, chain growth and chain termination, the elimination of free radicals and the decomposition of hydroperoxide are basic ways for inhibiting the oxidative degradation of the polymer. The inventors of the present disclosure have further discovered that the polylactic acid slices obtained are yellowish because of the side reactions such as thermal aging and thermo-oxidative aging of lactide; by adding the composite stabilizer, hydroperoxide can be decomposed into inactive products, the autocatalytic oxidation process is inhibited, and furthermore, the addition of 1-3%, preferably 2% of the composite stabilizer into the polymerization process of polylactic acid may desirably improve the color and lustre of the prepared polylactic acid slice, it can especially reduce the b value in the color and lustre of the slice by 78.0% as compared with the conventional polylactic acid slice in the prior art.

In the present disclosure, in terms of the selection of the composite stabilizer, the inventors of the present disclosure have found that the antioxidants widely used at present are mainly two types, namely hindered phenols and phosphite esters. In the anti-oxidation process, the hindered phenol captures peroxide free Radicals (ROO) of the polymer and then becomes hydroperoxide (ROOH), the hydroperoxide has the autocatalysis effect on an oxidative degradation, and the hindered phenol per se cannot decompose the hydroperoxide, so that it is difficult to produce ideal anti-oxidation effect when the hindered phenol is used alone. The antioxidant action of the phosphite ester, which occurs on the phosphorus atom, is capable of decomposing hydroperoxides from trivalent phosphorus to stable pentavalent phosphorus, but the phosphite ester is incapable of capturing the free radicals, its use alone cannot generate the satisfactory effect. The two components are mixed for use as a compound stabilizer, so that the effects of the two components are mutually complemented, the synergistic effect of the two components enables the effects of anti-oxidation and other aspects to be brought into full play, and the performance of the compound stabilizer is superior to an antioxidant with any single component.

In the screening of the antioxidant, the compounding of the main antioxidant and the auxiliary antioxidant is selected when considering from the three aspects of processing stability, long-acting stability, and color and lustre stability.

The main antioxidant is a hindered phenol antioxidant, and the hindered phenol antioxidant is tetra-[beta-(3,5-di-tert-butyl-4-hydroxyphenyl) propionic acid] pentaerythritol tetra (alcohol) ester (AT-10) and/or beta-(3,5-di-tert-butyl-4-hydroxyphenyl) octadecyl propionate (AT-76).

The auxiliary antioxidant is a phosphite ester antioxidant, and the phosphite ester antioxidant is tri-(2,4-di-tert-butylphenyl) phosphite (AT-168) and/or bi-(2,4-di-tert-butylphenyl) pentaerythritol diphosphite (AT-626).

Preferably, the weight ratio of the hindered phenol antioxidant to the phosphite antioxidant is 1:(0.1-3), more preferably 1:(0.5-2), and more further preferably 1:(1-2). According to the present disclosure, the hindered phenol antioxidant and the phosphite ester antioxidant are compounded according to the range previously defined in the description, so that the color and lustre of the prepared polylactic acid slice can be improved in a favorable manner, and especially the b value in the color and lustre of the slice can be desirably reduced.

According to the present disclosure, most preferably, the hindered phenol antioxidant and the phosphite ester antioxidant are specifically compounded as follows:

(1) compounding AT-10 and AT-168 according to the mass ratio of 1:1 to form a composite stabilizer which is marked as CS-1;

(2) compounding AT-10 and AT-626 according to the mass ratio of 1:1 to form a composite stabilizer which is marked as CS-2;

(3) compounding AT-76 and AT-168 according to the mass ratio of 1:1 to form a composite stabilizer which is marked as CS-3;

(4) compounding AT-76 and AT-626 according to the mass ratio of 1:1 to form a composite stabilizer which is marked as CS-4;

(5) compounding AT-10 and AT-168 according to the mass ratio of 1:2 to form a composite stabilizer which is marked as CS-5;

(6) compounding AT-10 and AT-626 according to the mass ratio of 1:2 to form a composite stabilizer which is marked as CS-6;

(7) compounding AT-76 and AT-168 according to the mass ratio of 1:2 to form a composite stabilizer which is marked as CS-7;

(8) compounding AT-76 and AT-626 according to the mass ratio of 1:2 to form a composite stabilizer which is marked as CS-8;

(9) compounding AT-10 and AT-168 according to the mass ratio of 2:1 to form a composite stabilizer which is marked as CS-9;

(10) compounding AT-10 and AT-626 according to the mass ratio of 2:1 to form a composite stabilizer which is marked as CS-10;

(11) compounding AT-76 and AT-168 according to the mass ratio of 2:1 to form a composite stabilizer which is marked as CS-11;

(12) compounding AT-76 and AT-626 according to the mass ratio of 2:1 to form a composite stabilizer which is marked as CS-12.

According to the present disclosure, the hindered phenol antioxidant and the phosphite ester antioxidant are compounded according to the above definition, so that the color and lustre of the polylactic acid slice can be significantly improved, and the b value in the color values is 4.19 at the lowest, which is reduced by 78.0% compared with the conventional polylactic acid slice.

According to the present disclosure, the weight ratio of the used amounts of the lactide, the catalyst, the composite stabilizer and the initiator is 1:(0.002-0.005):0.001-0.002):(0.008-0.01); preferably 1:(0.002-0.004):(0.001-0.015):(0.008-0.009). In the present disclosure, it is further preferable that the weight ratio of the used amounts of the lactide, the catalyst, the composite stabilizer and the initiator is 1:0.002:0.0015:0.008, such that the polylactic acid melt with desirable cost and performance can be obtained.

According to the present disclosure, the conditions of the first polymerization reaction in the step (b) comprise: the temperature is within a range of 150-160° C., the pressure is 50-53 KPa, and the reaction time is 3-3.2 h; preferably, the temperature is within a range of 155-160° C., the pressure is 50-52 kPa, and the reaction time is 3-3.1 h.

In the present disclosure, the conversion rate of the first melt obtained after the first polymerization reaction is as high as 50-55%.

According to the present disclosure, the conditions of the second polymerization reaction in the step (c) comprise: the temperature is within a range of 190-200° C., the pressure is 6-6.5 MPa, and the reaction time is 1-1.2 h; preferably, the temperature is within a range of 195-200° C., the pressure is 6-6.2 MPa, and the reaction time is 1-1.1 h.

In the present disclosure, the conversion rate of the second melt obtained after the second polymerization reaction is as high as 95-97%.

In addition, it should be noted that in the second polymerization reaction, the conversion rate is increased due to the interaction of the melt pulsation deformation device and the static mixer.

According to the present disclosure, the conditions of the demonomerization reaction in step (d) comprise: adding a terminator into the melt after the second polymerization reaction for terminating the reaction, wherein the terminator is phosphorous acid and/or 2-ethyl octanoic acid; preferably, the mass ratio of used amounts of the lactide to the terminator is 1:(0.002-0.005), preferably 1:(0.002-0.003).

The temperature is within a range of 210-215° C., the pressure is 1-1.2 kPa, and the reaction time is 0.5-0.6 h; the stirring speed is 10-30 rpm; the amplitude is 0.15-0.3 mm, and the vibration frequency is 20-45 Hz. In the demonomerization reaction process of the present disclosure, the electromagnetic vibration exciter 4-1 in the demonomerization reactor IV is connected with a stirring drive motor 4-2 through the vibration transmission disc to enable the stirring drive motor 4-2 to vibrate axially, so that the content of the lactide remained in the second melt can be effectively reduced, and the lactide content in the obtained polylactic acid slice can be desirably reduced. In addition, the stirring shaft 4-7-1 axially vibrates along with the action of the exciting force of the electromagnetic vibration exciter 4-1, the scraper 4-7-2 on the stirring shaft 4-7-1 also generates periodic change along with the vibration of the stirring shaft 4-7-1, a vibration force field is introduced into the polylactic acid melt, the polylactic acid high-viscosity melt forms an uniform, ultra-thin film structure on the inner wall through the vibration scraper, the film structure can provide a large enough surface area, and in the production process, the combination of a large film-forming area and a quick surface updating can be realized by using the demonomerization reactor IV, it is conducive to improving the dispersion and mixing of the melt, increasing the volatilization amount of lactide monomers, meeting the requirement of quickly removing the monomers, and controlling the content of the lactide monomers in the residual polylactic acid melt to the minimum degree.

According to the present disclosure, the method further comprises the steps of carrying out water-cooling pelletizing, dehydration, crystallization and drying treatment in regard to the polylactic acid melt obtained in the step (d); in the present disclosure, the polylactic acid melt after the step (d) is introduced into a twin-screw extruder V through a melt pipeline and a material discharge pump, and the polylactic acid resin is finally obtained through water-cooling pelletizing, dehydration, screening, crystallization, dehumidification and drying, wherein the temperature of a pelletizer is within a range of 205-210° C.

Wherein the rotation speed of the water-cooling pelletizing process is within a range of 1,500-3,000 rpm, the dehydration rotation speed is 800-1,000 rpm, the crystallization temperature is 90-95° C., the time is 35-45 min, the temperature of dehumidification and drying is 90-98° C., and the time is 1-2 h; preferably, the crystallization temperature is 95° C. and the time is 40 min, the temperature of dehumidification and drying is 95° C. and the time is 1.5 h.

The present disclosure also provides polylactic acid prepared with the aforementioned method.

According to the present disclosure, the weight average molecular weight of the polylactic acid is within a range of 80,000-250,000, the content of lactide monomer in the polylactic acid is 0.8-1.0 wt %, and the melt index of the polylactic acid at 190° C. under a load of 2.16 kg is within a range of 6-27 g/10 min; preferably, the weight average molecular weight of the polylactic acid is within a range of 100,000-250,000, the content of lactide monomer in the polylactic acid is 0.8-0.9 wt %, and the melt index of the polylactic acid at 190° C. under a load of 2.16 kg is within a range of 8-27 g/10 min.

Through above technical solution, the polylactic acid is prepared by adopting the device and the method of the present disclosure, particularly, the composite stabilizer is added in the lactide polymerization process, the color defect of the polylactic acid slice can be well improved, and the b value in the color value of a final product is 4.19, which is reduced by 78% compared with the conventional polylactic acid slice; in the demonomerization reaction process, a rotating shaft of the monomer removing device adopts an electromagnetic vibration exciter to carry out axial vibration, such that the content of the residual lactide monomer in the polylactic acid melt can be effectively reduced, and the content of the lactide monomer in the finally obtained polylactic acid slice is 0.8%, which is reduced by 80.5% compared with the PLA slice produced with the conventional process. In addition, the polylactic acid slices prepared with the device and the method have low yellowness index and high devolatilization efficiency, and the industrial production of high-quality PLA slices is realized.

The polylactic acid (solution) obtained by the present disclosure can be further prepared into a modified polylactic acid material, therefore, the present disclosure provides a device for preparing the modified polylactic acid material on line from a melt, wherein the device comprises a twin-screw extruder, a first solid modifier hopper 8c, a polylactic acid melt pipeline 14c and a polylactic acid melt feeding and metering pump 10c, the first solid modifier hopper 8c is connected with zone I 2c of the twin-screw extruder, and the polylactic acid melt pipeline 14c is connected with zones IV 4c of the twin-screw extruder.

In the present disclosure, it shall be noted that the polylactic acid melt is prepared by COFCO Biochemistry Co., Ltd., and the preparation method comprises the following steps: subjecting lactide to polymerization and devolatilization to obtain a polylactic acid melt; the lactide is purchased from Total Corbion PLA (Thailand) Ltd., with a trade name Lumilact®L, a net weight 600 kg, a model number L85 and a purity of 99.5%.

According to the present disclosure, the apparatus further comprises a second solid modifier hopper 9c and a second auxiliary material hopper 13c, wherein the second solid modifier hopper 9c is connected with a zone I 2c of the twin-screw extruder; the second auxiliary material hopper 13c is connected with a zone V 5c of the twin-screw extruder.

According to the present disclosure, the apparatus also comprises a first auxiliary material hopper 11c, the first auxiliary material hopper 11c is connected to a zone I 2c of the twin-screw extruder, and is used for feeding the powder auxiliary materials.

According to the present disclosure, the twin-screw extruder further comprises a liquid feedstock metering pump 12c, and the liquid feedstock metering pump 12c is connected with the zone II 3c of the twin-screw extruder.

Figure 8:
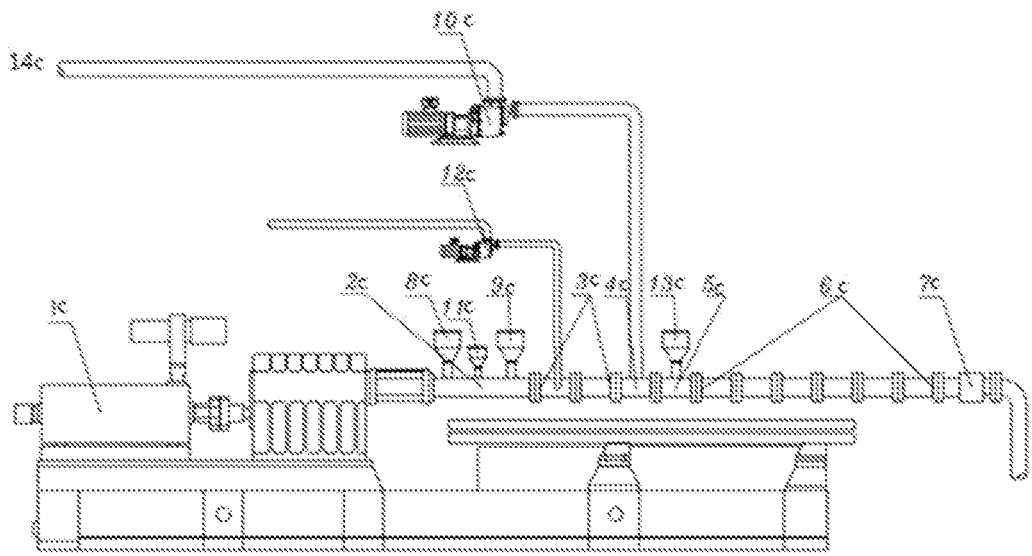
FIG. 8 shows a schematic view of an apparatus for online preparation of a modified polylactic acid material according to the present disclosure.

According to the present disclosure, FIG. 8 is a schematic diagram of an apparatus for online preparation of a modified polylactic acid material according to the present disclosure, the twin-screw extruder further comprises a motor 1c and a twin-screw extruder headpiece 7c; in addition, a zone I 2c of the twin-screw extruder, zones II to III 3c of the twin-screw extruder, a zone IV 4c of the twin-screw extruder, a zone V 5c of the twin-screw extruder, and zones VI to XI 6c of the twin-screw extruder are shown in FIG. 8.

The present disclosure also provides a method for online preparation of a modified polylactic acid material, wherein the method is performed in a device for online preparation of a modified polylactic acid material, the method comprises the following steps:

(a) feeding the polylactic acid melt into a zone IV 4c of a twin-screw extruder through a polylactic acid melt pipeline 14c;

(b) adding a first solid modifier into a zone I 2c of the twin-screw extruder via a first solid modifier hopper 8c;

(c) feeding a liquid modifier into a zone II 3c of the twin-screw extruder through a liquid feedstock metering pump 12c;

(d) contacting the polylactic acid melt, the first solid modifier and the liquid modifier in zones V 5c of the twin-screw extruder to zone XI 6c of the twin-screw extruder, and extruding and granulating the obtained modified polylactic acid polymeric melt;

wherein the device for online preparation of a modified polylactic acid material is the aforementioned device.

According to the present disclosure, the liquid modifier is one or more selected from the group consisting of epoxidized soybean oil, tributyl citrate and adipic acid diethylene glycol monobutylether ester.

Wherein the epoxidized soybean oil (ESO) is a light yellow viscous oily liquid under the normal temperature, the molecular formula is $C_{57}H_{106}O_{10}$, the molecular weight is 950, the epoxy value is greater than or equal to 6.60, the iodine value is less than or equal to 3.0, the higher is the epoxy value of the ESO, the better is the heat resistance, the lower is the iodine value, the better is the compatibility with polyvinyl chloride (PVC), the less easier it is precipitated.

Wherein the tributyl citrate is generally called tri-n-butyl citrate, the chemical name of the tributyl citrate is 3-hydroxy-3-carboxyl glutaric acid tributyl ester, which is an ester compound.

According to the present disclosure, the dosage of the polylactic acid melt is 49.5-79 wt %, the dosage of the first solid modifier is 20-50 wt %, and the dosage of the liquid modifier is 0.2-0.5 wt %, based on the total weight of the modified polylactic acid melt; preferably, the dosage of the polylactic acid melt is 53-66.8 wt %, the dosage of the first solid modifier is 25-35 wt %, and the dosage of the liquid modifier is 0.2-0.3 wt %, based on the total weight of the modified polylactic acid melt. In the present disclosure, the total amount of dosages of the polylactic acid melt, the first solid modifier and the liquid modifier is 100%.

According to the present disclosure, the method further comprises: in step (b), the first solid modifier is fed into the zone I 2c of the twin-screw extruder via a first solid modifier hopper 8c, and a second solid modifier is fed into the zone I 2c of the twin-screw extruder via a second solid modifier hopper 9c.

According to the present disclosure, the first solid modifier and the second solid modifier are identical or different, each is a toughening agent and/or a reinforcing agent.

In the present disclosure, the toughening agent is one or more selected from the group consisting of polybutylene adipate terephthalate, polypropylene carbonate, polybutylene succinate, polytetramethylene glycol-succinic acid/adipic acid copolyester, preferably polybutylene adipate terephthalate and/or polypropylene carbonate.

In the present disclosure, the reinforcing agent is talc and/or calcium carbonate.

According to the present disclosure, the dosage of the polylactic acid melt is 49.5-79 wt %, the dosage of the first solid modifier is 20-50 wt %, the dosage of the second solid modifier is 0-7 wt %, and the dosage of the liquid modifier is 0.2-0.5 wt %, based on the total weight of the modified polylactic acid melt; preferably, the dosage of the polylactic acid melt is 53-66.8 wt %, the dosage of the first solid modifier is 25-35 wt %, the dosage of the second solid modifier is 3-7 wt %, and the dosage of the liquid modifier is 0.2-0.3 wt %, based on the total weight of the modified polylactic acid melt. In the present disclosure, the total amount of dosages of the polylactic acid melt, the first solid modifier, the second solid modifier and the liquid modifier is 100%.

According to the present disclosure, the method further comprises: in step (d), the polylactic acid melt, the first solid modifier, the liquid modifier and the auxiliary material are contacted, wherein the auxiliary material enters the zone V 5c of the twin-screw extruder via the second auxiliary material hopper 13c.

According to the present disclosure, the auxiliary material is one or more selected from the group consisting of a chain extender, a cross-linking agent, an antioxidant and a lubricant.

According to the present disclosure, the dosage of the polylactic acid melt is 49.5-79 wt %, the dosage of the first solid modifier is 20-50 wt %, the dosage of the liquid modifier is 0.2-0.5 wt %, the dosage of the chain extender is 0-0.3 wt %, the dosage of the cross-linking agent is 0-0.3 wt %, the dosage of the antioxidant is 0-0.5 wt %, and the dosage of the lubricant is 0-0.4 wt %, based on the total weight of the modified polylactic acid melt; preferably, the dosage of the polylactic acid melt is 53-66.8 wt %, the dosage of the first solid modifier is 25-35 wt %, the dosage of the liquid modifier is 0.2-0.3 wt %, the dosage of the chain extender is 0.1-0.2 wt %, the dosage of the cross-linking agent is 0.1-0.2 wt %, the dosage of the antioxidant is 0.2-0.3 wt %, and the dosage of the lubricant is 0.2-0.3 wt %, based on the total weight of the modified polylactic acid melt. In the present disclosure, the total amount of the dosages of the polylactic acid melt, the first solid modifier, the liquid modifier, the chain extender, the crosslinking agent, the antioxidant and the lubricant is 100%.

The present disclosure also provides a modified polylactic acid material prepared with the aforementioned method.

Through above technical solution, the method has the beneficial effects that the online modification of the polylactic acid melt obtained by polymerization is realized by adding the modifier online, so that the secondary processing is omitted, the production cost is greatly reduced, and the degradation of the polylactic acid resulting from the secondary processing can be avoided, such that the excellent performance of the final product is ensured.

The present disclosure provides a polylactic acid devolatilization evaporator, wherein the polylactic acid devolatilization evaporator comprises:

a container including a circular tube-shaped cylinder body 3 that extends vertically;

a stirring shaft 5 which is at least partially disposed in the cylinder body 3, and the stirring shaft 5 is coaxial with the cylinder body 3;

a stirring belt 6 which is connected to the stirring shaft 5, the stirring belt 6 is disposed in a spiral shape around a central axis of the cylinder body 3, the stirring belt 6 includes an outer belt surface facing an inner circumferential surface of the cylinder body 3, and the outer belt surface is spaced apart from the inner circumferential surface of the cylinder body 3 for each other. Unless otherwise specified in the present disclosure, the use of the directional term such as "upper and lower" generally refers to the positional relationship when the cylinder body of the container extends vertically.

Figure 9:
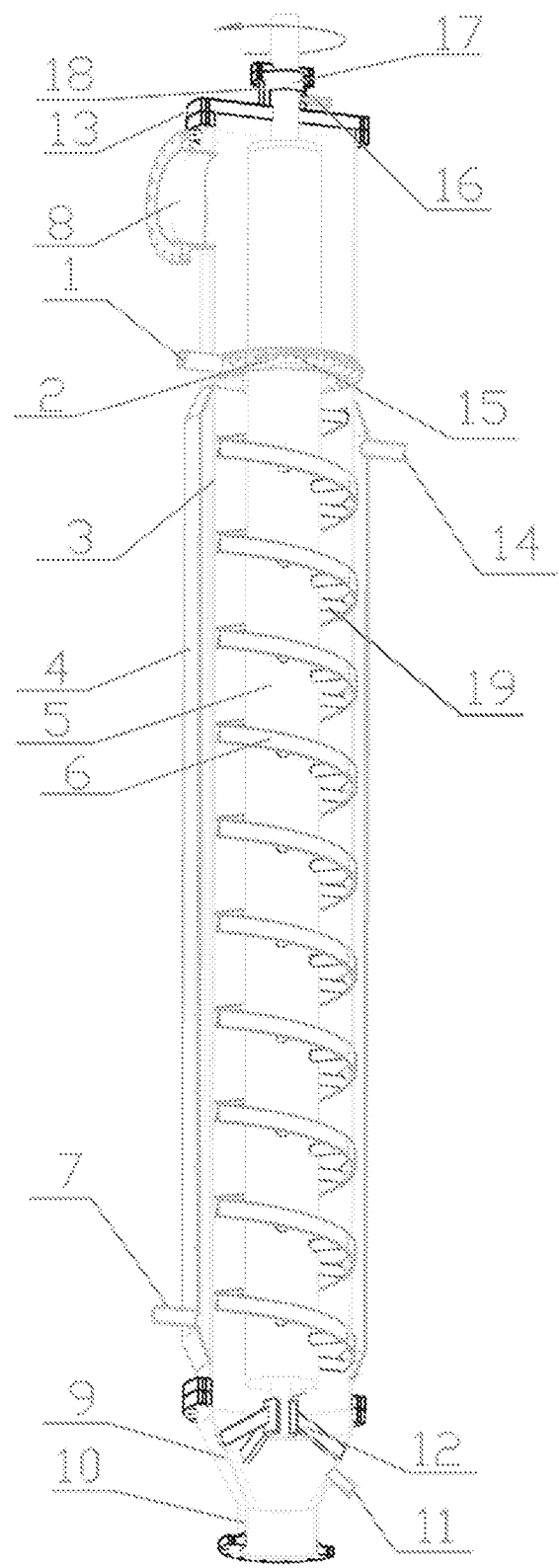
FIG. 9 is a schematic view showing the structure of a polylactic acid devolatilization evaporator according to an embodiment of the present disclosure.

The polylactic acid devolatilization evaporator of the present disclosure can be used for the devolatilization process of polylactic acid, it is certain that the evaporator can also be applied in the devolatilization process of polymers with similar properties. The container accommodates the material to be treated and an internal component of the evaporator, it comprises a cylinder body 3, wherein the cylinder body 3 is formed into a circular tube shape, and can be disposed to vertically extend when in use, such that the material can be stirred and treated by using a rotating stirring element; the stirring shaft 5 is a transmission part that can be connected to a power driving member (e.g., an engine, an electric motor) to be driven to rotate around the central axis of the cylinder body 3; the stirring belt 6 is connected with the stirring shaft 5 so as to rotate following the stirring shaft 5. In addition, the polylactic acid devolatilization evaporator comprises a feeding pipe 1 passing through a cylinder body 3, and a distributor 2 connected to the feeding pipe 1, the distributor 2 includes a ring-shaped pipe extending circumferentially around the central axis of cylinder body 3, the ring-shaped pipe is provided with a material distribution port 15. As shown in FIG. 9, the feeding pipe 1 penetrates through the cylinder body 3 and is connected with the distributor 2 in the cylinder body 3, the distributor 2 is a circumferential annular pipe and is provided with a material distribution port 15 thereon; the feeding pipe 1 can convey materials into the distributor 2 and distribute the materials on the inner wall of the cylinder body 3 relatively uniformly through the material distribution port 15. In other embodiments, the feeding pipe extending from other portions of the container (e.g., the sealing cover 13) into the interior of the cylinder body 3 may be used, with or without the use of the distributor 2.

Further, the distributor 2 is located on the upper side of the stirring belt 6, the material distribution port 15 faces the inner circumferential surface of the cylinder body 3, and the material distribution port 15 preferably inclines downward. The material distribution port 15 of the distributor 2 may be formed at a radially outer side to face the inner circumferential surface of the cylinder body 3, so that the material may adhere to the inner circumferential surface of the cylinder body 3 after being sprayed and flow downward along the inner wall of the cylinder body 3 by gravity. Preferably, the material distribution openings 15 are slightly inclined downwards, such that the material sprayed from the material distribution port reaches the inner circumferential surface of the cylinder body 3 at a position closer to the height position of the stirring belt 6 located below. The material distribution port 15 may be a hole, a slit or the like.

As shown in FIG. 9, the stirring belt 6 is formed in a spiral shape around the central axis of the cylinder body 3, it has an outer belt surface facing the inner circumferential surface of the cylinder body 3, and the outer belt surface is spaced apart from the inner circumferential surface of the cylinder body 3. The pitch of the helical stirring belt 6 may be 0.1-2 times, preferably 0.2-1.2 times, and most preferably 0.3-0.8 times of the inner diameter of the cylinder body 3; the width of the outer belt surface of the helical stirring belt 6 may be 0.01-0.15 times, preferably 0.02-0.1 times, and most preferably 0.03-0.08 times the inner diameter of the cylinder body 3. When the viscous material is adhered to the inner circumferential surface of the cylinder body 3, the rotating stirring belt 3 can enable the material to be located between the outer side belt surface and the inner circumferential surface of the cylinder body 3, in addition, according to the spiral direction (e.g., left-handed rotation or right-handed rotation) of the stirring belt 6, the stirring belt 6 can downwards scrape the material on the inner circumferential surface of the cylinder body 3 by adjusting the rotating direction (e.g., clockwise or anticlockwise rotation) of the stirring shaft 5, so that the material is more uniformly coated on the inner circumferential surface of the cylinder body 3. After the material is heated on the side wall of the cylinder body 3, the viscosity of the material gradually increases along with the gradual evaporation of the micromolecule volatile components contained in the material. By means of the scraping force imposed on the material by the stirring belt 6, it allows the material with a thick slurry form after removing a portion of the volatile ingredient to move downwards and helically along the inner wall of the cylinder body, in this way, it can prevent that the material from being fastened and adhering to an inner wall of the cylinder body due to excessive viscosity, and avoid that the material cannot be heated sufficiently because the material sticks together and agglomerates in a local areas of the inner wall of the cylinder body and then fall into the bottom of said cylinder body, such that the material can be heated in a relatively uniform manner, the devolatilization effect is improved by preventing the material from color darkening and pyrolysis due to excessive heating and avoiding the problem of insufficient devolatilization resulting from that a portion of the material is not sufficiently heated.

Regarding the rotation direction of the stirring belt 6, refer to FIG. 9, wherein the stirring belt 6 is in a left-handed rotation, the stirring belt 6 rotates clockwise, i.e. the material can be scraped downwards axially by the lower side edge of each position, and when the stirring belt is in a right-handed rotation, it can rotate counterclockwise correspondingly. The core structure of the stirring belt 6 is the outer belt surface, and the stirring belt 6 is not limited to a belt-like structure, as long as it has the outer belt surface spaced from the inner circumferential surface of the cylinder body 3, which belongs to the protection scope of the present disclosure. Without doubt, it is a preferable embodiment to form a belt-shaped stirring belt.

Optionally, the outer band surface is spaced from the inner circumferential surface by a distance of 2 mm to 30 mm. The intervals between the outer side belt surface and the inner circumferential surface of the stirring belt 6 at different positions may be kept consistent, so that a uniform material layer is formed on the inner circumferential surface of the cylinder body 3, the interval may be within a range of 2 mm-30 mm, such that a material layer with a thickness of 2 mm-30 mm can be formed on the inner circumferential surface of the cylinder body 3.

In an embodiment shown in FIG. 9, the stirring belt 6 is radially spaced from the stirring shaft 5, and the stirring belt 6 is connected with the stirring shaft 5 by a connection rod 19. Referring to FIG. 9, the stirring shaft 5 may extend from the upper portion to the lower portion of the cylinder body 3, and the outer diameter of the stirring shaft 5 is smaller than the inner diameter of the spiral structure formed by the stirring belt 6, and the stirring belt 6 is connected to the stirring shaft 5 by the connection rod 19, so that a large space is formed between the stirring belt 6 and the stirring shaft 5, allowing the gaseous fluid generated during the devolatilization process of the material to be discharged. Of course, the stirring belt 6 and the stirring shaft 5 can also be connected in other modes, for example, a spiral plate with openings may be arranged between the stirring belt 6 and the stirring shaft 5, the outer edge of the spiral plate is welded with the spiral stirring belt 6, the inner edge of the spiral plate is welded with the stirring shaft 5, so that the stirring shaft 5 and the stirring belt 6 are connected to form a rigid body, the stirring belt can be driven by the stirring shaft to rotate in the evaporator, and volatile gas evaporated in the evaporator can rise to the upper space of the evaporator through the opening on the spiral plate and then is discharged via the discharge port 8.

Furthermore, the polylactic acid devolatilization evaporator comprises a support frame 12 arranged at the bottom of the container, and the lower end of the stirring shaft 5 is rotatably supported on the support frame 12. Referring to FIG. 9, the supporting frame 12 is formed substantially in the shape of a tripod to support the lower end of the stirring shaft 5 and allow the stirring shaft 5 to rotate. The support frame 12 may be supported on the tapered inner circumferential surface of the conical cylinder 9, but of course, the support frame 12 may be supported on the inner circumferential surface of the cylinder body 5 in other embodiments.

As shown in FIG. 9, the polylactic acid devolatilization evaporator comprises a clamp ferrule 4 wrapped outside the cylinder body 3, and a sealed cavity is formed between the clamp ferrule 4 and the cylinder body 3. A steam inlet pipe 14 is arranged at the upper end of the clamp ferrule 4, and a steam condensate outlet pipe 7 is disposed at the lower end of the clamp ferrule 4. Steam introduced into the clamp ferrule 4 transfers heat to the viscous material which creeps down along the inner wall of the cylinder through the cylinder body 3, so that components with relatively low boiling points in the material, such as a solvent for diluting a catalyst, unpolymerized lactide monomer, or small molecular acid or ester substances generated by side reactions such as hydrolysis in the polymerization process, are gasified into gas and volatilized from the material. Of course, it is also possible to use heat transfer oil or hot water as the heating medium. However, when a liquid heating medium is used, the heating medium should be introduced from the bottom of the clamp ferrule 4 and discharged from the top of the clamp ferrule 4. In order to reduce the heat loss caused by the heat dissipation of the system to the environment and prevent scalding accidents, it is generally required to arrange a heat insulation layer with the thickness not less than 5 cm outside the clamp ferrule 4.

In addition, the container includes a sealing cover 13 connected to the upper end of the cylinder body 3 and a sealing box 18 disposed on the sealing cover, the stirring shaft 5 rotatably penetrates the sealing cover 13 and the sealing box 18, a sealing filler 17 is provided between the stirring shaft 5 and the sealing box 18, and a sealing gas injection pipe 16 is preferably formed on the sealing box 18. Referring to FIG. 9, a sealing cap 13 is sealed at the upper end of the cylinder body 3, and the sealing cap 13 is integrally connected with a sealing box 18, the sealing box 18 is substantially formed with a tubular shape, and the stirring shaft 5 passes through the sealing cap 13 and the sealing box 18 and surrounds the stirring shaft 5 by a sealing filler 17, thereby improving sealing performance. Moreover, it is preferable that a sealing gas injection pipe 16 is provided at a side portion of the sealing box 18, and a gas can be injected into a gap between the sealing box 18 and the stirring shaft 5 through the sealing gas injection pipe 16, such that a slight positive pressure can be maintained in the gap, the entry of external gas or impurities into the gap between the sealing box 18 and the stirring shaft 5 can be prevented. The injected gas may be an inert gas, such as nitrogen, argon, etc.

In addition, the upper part of the cylinder body 3 is provided with a discharge pipe 8 which can be connected with a vacuum apparatus, the lower end of the cylinder body 3 is connected with a conical cylinder 9, the lower end of the conical cylinder 9 forms a discharge port 10, the side wall of the conical cylinder 9 is connected with an inert gas injection pipe 11. The inner diameter of the conical cylinder 9 is continuously reduced downwards, and materials after devolatilization can be discharged through a discharge port 10 at the bottom; a protective gas can be injected into the cylinder body 3 through the inert gas injection pipe 11, and the air in the cylinder body is exhausted, so as to avoid the chemical reaction between the materials in the cylinder body and the air; the discharge pipe 8 may be connected with a vacuum apparatus to vacuumize the cylinder body 3 and reduce the pressure therein for performing devolatilization and evaporation of the material; in addition, gas may be injected through the inert gas injection pipe 11 to reduce the partial pressure of the gaseous material generated by devolatilization and promote the devolatilization.

Figure 10:
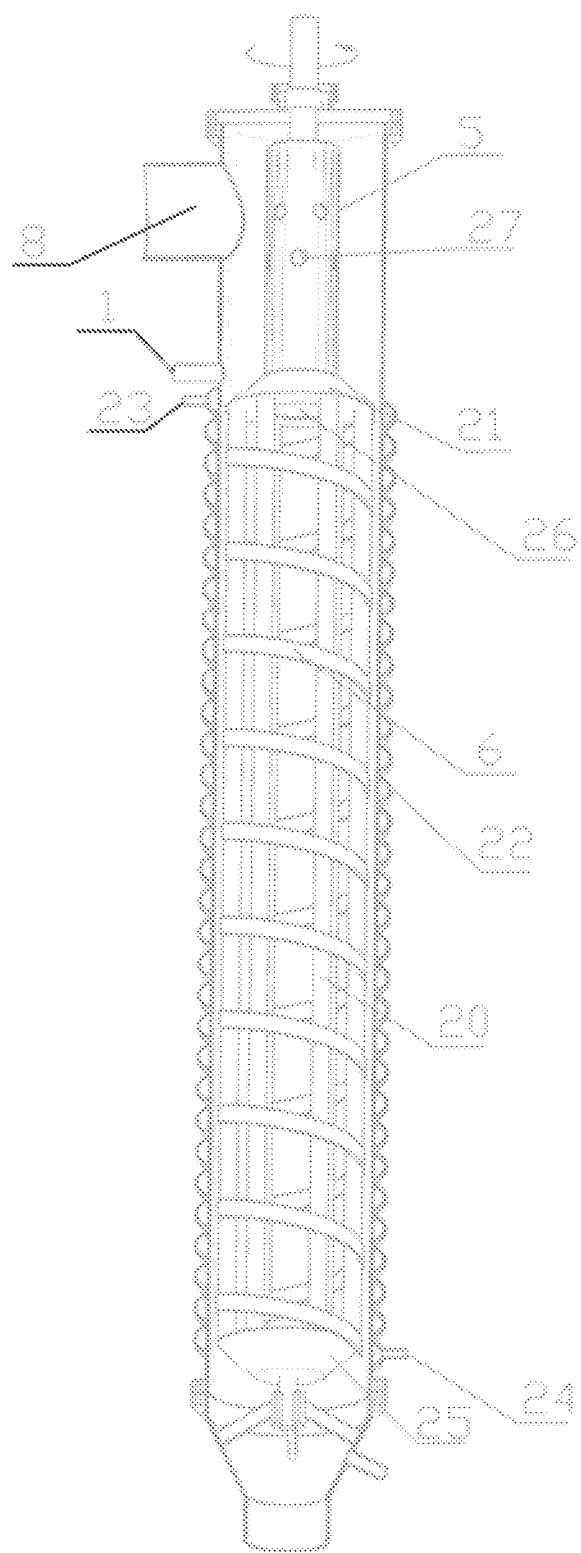
FIG. 10 illustrates a schematic view showing the structure of a polylactic acid devolatilization evaporator according to another embodiment of the present disclosure.

According to another embodiment of the present disclosure, as shown in FIG. 10, the polylactic acid devolatilization evaporator comprises a plurality of support rods 20 circumferentially spaced around the central axis of the cylinder body 3, and an upper connection base 21 and a lower connection base 25 connected to both ends of the support rods 20, wherein the upper connection base 21 is connected with the stirring shaft 5, the stirring shaft 5 has a hollow tubular structure, 4 to 16 exhaust holes 27 are circumferentially opened on the side wall of the tubular stirring shaft 5, the total area of the exhaust holes is approximately equal to the cross-sectional area of the tubular stirring shaft. An exhaust hole 26 is provided in the center of upper connection base 21, and the cross-sectional area of the hole is also approximately equal to the cross-sectional area of the tubular stirring shaft. The volatile gaseous component evaporated after the material is heated in the evaporator, may enter the inner chamber of the stirring shaft 5 through the exhaust hole of the upper connection base 25, and is discharged into the space on the upper portion the evaporator from the exhaust hole on the side wall of the stirring shaft 5, and is finally discharged from the evaporator via a discharge port 8. The support rods are attached to the radially inner surface of the stirring belt 6. The clearance between the radially outer side surface of the stirring belt 6 and the inner side surface of the cylinder body 3 is within a range of 2-30 mm. Referring to FIG. 10, a plurality of support rods 20 and two connection bases 21, 25 constitute a support structure of the stirring belt 6, and the support rods 20 are attached to the radially inner surface of the stirring belt 6, which also forms a passage in the inner space surrounded by the stirring belt 6 for allowing gas to be discharged. The upper connecting base 21 is connected with the stirring shaft 5 so as to drive the support rod 20 and the stirring belt 6 to rotate through the stirring shaft 5. The gap between the outer edge of the lower end of the upper connection base 21 and the inner wall of the cylinder body 3 has a width of 1-25 mm, and after the material introduced from the feeding pipe 1 enters the evaporator, the material flows downwards along the inner wall of the cylinder body 3 through the gap between the upper connection base 21 and the inner wall of the cylinder body 3. When the outlet of the feeding pipe 1 is not provided with a distributor but the feed liquid is distributed by using the gap between the upper connection 21 and the inner wall of the cylinder body 3, it is preferable that the feeding pipe 1 is communicated with the cylinder body 3 along the tangential direction of the cylinder body 3.

In an embodiment shown in FIG. 10, a heating spiral coil pipe 22 is welded to the outer wall of the cylinder body 3, the heat conduction oil or high-temperature hot water enters the heating spiral coil pipe 22 through a heating medium inlet pipe 24 and then flows out from a liquid heating medium outlet pipe 23. In order to reduce the heat loss caused by the heat dissipation of the system to the environment and prevent scalding accidents, it is generally required to arrange a heat insulation layer with the thickness not less than 5 cm outside the heating spiral coil pipe.

When the evaporator provided by the present disclosure is used for devolatilizing polylactic acid, the inlet temperature range of the heating medium which is introduced into the clamp ferrule 4 or the heating spiral coil pipe 22 is 180-240° C., the preferred temperature range is 190-230° C., and the most preferred temperature range is 200-225° C.; the pressure in the evaporator is in the range of 0.1 kPa-20 kPa, preferably in the range of 1 kPa-10 kPa, and most preferably in the range of 2 kPa-8 kPa; the rotation speed of the mixing shaft is within a range of 5-120 rpm, preferably 10-60 rpm, most preferably 15-45 rpm.

By adopting the technical solution provided by the present disclosure, after the material enters the devolatilization device, the material can be relatively uniformly distributed on the inner surface of the cylinder body at the upper part of the devolatilization evaporator and subjected to heating, so that the volatile components in the material are gasified and enter the gas phase space in the cylinder body. As the volatile small molecule components contained in the material are continuously evaporated, the viscosity of the material gradually increases during the process of flowing downwards along the side wall of the cylinder. After the content of volatile components in the material is reduced to a certain degree, the material cannot flow downwards smoothly along the side wall by the gravity of the material because the viscosity is too high. The present disclosure arranges the spiral stirring belt around the stirring shaft of the evaporator and close to the side wall of the cylinder body, and can apply a downward inclined scraping force to the materials adhered on the inner wall of the cylinder body along with the stirring shaft driving the stirring belt to rotate in the evaporator, such that the material with a thick slurry form after removing a portion of the volatile ingredient can move downwards and helically along the inner wall of the cylinder body, in this way, it can prevent that the material from being fastened and adhering to an inner wall of the cylinder body due to excessive viscosity, and avoid that the material cannot be heated sufficiently because the material sticks together and agglomerates in a local areas of the inner wall of the cylinder body and then fall into the bottom of said cylinder body, such that the material can be heated in a relatively uniform manner during the whole devolatilization process, and the retention time lengths of the materials in the high-temperature environment in the devolatilization evaporator are approximately the same, thus it is beneficial to improving the quality of the devolatilized polylactic acid product. In addition, after volatile components to be removed are subjected to heating and gasifying in the devolatilization evaporator provided by the present disclosure, the volatile components can quickly escape from the thin-layer material on the side wall of the cylinder body and then are smoothly discharged from the evaporator through the gaseous material flow channel in the cylinder body, so that the high devolatilization efficiency can be obtained.

The present invention will be described in detail below with reference to examples. Unless otherwise specified in the following examples, the reagents and culture media used herein are all commercially available products, and the applied methods pertain to conventional methods.

Examples 1.1 to 1.2 and Comparative Example 1.1

These examples are used for illustrating the lactic acid fermentation strains associated with the present disclosure. Wherein:

1. Culture medium

MRS liquid culture medium comprises: 10 g of peptone, 5 g of yeast extract, 10 g of beef extract, 20 g of glucose, 2 g of dipotassium phosphate, 2 g of diammonium citrate, 5 g of anhydrous sodium acetate, 0.25 g of manganese sulfate, 0.58 g of magnesium sulfate, 1 mL of tween 80 and 1,000 mL of distilled water, wherein the pH was 6.5, and the sterilization was carried out at 121° C. for 20 min;

Acidogenic fermentation medium comprises: 180 g/L of glucose, 10 g/L of yeast extract, 2 g/L of sodium acetate, 0.5 g/L of $KH_2PO_4$, 0.5 g/L of $MgSO_4 \cdot 7H_2O$, 0.2 g/L of $MnSO_4$, and 1 ml/L of tween 80, 90 g/L of $CaCO_3$.

2. The content of lactic acid was detected by high performance liquid chromatography:

Chromatograph: Agilent Technologies 1260 Infinity II;
Detector: RID;
Separation column: Aminex HPX-87H Column 300×7.8 mm;
Mobile phase: 0.05M sulfuric acid;
Flow rate: 0.5 mL/min;
Sample injection amount: 20 μL;
The retention time of lactic acid was about 14 min.

3. The contents of glucose and L-lactic acid were detected by a biosensor:

Instrument: SBA-40E type biosensor;
Enzyme membrane: D-glucosidase and L-lactate membranes;
Sample injection amount: 25 μL.

4. The optical purity of lactic acid was detected by high performance liquid chromatography:

Chromatograph: Agilent Technologies 1260 Infinity;
Detector: wavelength 254 nm, sensitivity 0.32 AUFS;
Separation column: MCI GEL-CRS10W (3 u) 4.6 ID×50 mm;
Mobile phase: 0.002M copper sulfate;
Flow rate: 0.5 mL/min;
Sample injection amount: 20 μL.

The sample was diluted to the total concentration of lactic acid being within a range of 0.5-1 g/L and subjected to detection. The retention time of D-lactic acid was about 11 min, the retention time of L-lactic acid was about 13 min, and the optical purity of the L-lactic acid was calculated according to the peak area.

The glucose-lactic acid conversion rate was calculated by the following formula: total mass of lactic acid at the end of fermentation/initial mass of glucose.

Example 1.1

A single colony of the *Lactobacillus rhamnosus* strain CGMCC No. 19507 was selected and inoculated in an MRS liquid culture medium, and the mixture was cultured overnight at 37° C. and 150 rpm to obtain a seed solution with $OD_{600}$ of 12. The seed solution was then inoculated into 200 mL of an acidogenic fermentation culture medium in a proportion of 10% (v/v), and the mixture was subjected to shake bed cultivation at 37° C. and 150 rpm for 6 hours to allow the strains to grow, and then the temperature was raised to 48° C., the mixture was subjected to shake bed cultivation at 150 rpm for 42 hours to obtain a fermentation broth (the total fermentation time was 48 hours). After the fermentation was finished, the total yield of the lactic acid and the optical purity of the L-lactic acid were measured by using high performance liquid chromatography.

As a result, when the *Lactobacillus rhamnosus* strain CGMCC No. 19507 were fermented at 48° C. under the shake flask level of 200 mL, the lactic acid content in the fermentation broth obtained by fermenting the *Lactobacillus rhamnosus* strain for 48 hours was 216 g/L, the conversion rate of the glucose-lactic acid was 97%, and the optical purity of L-lactic acid was 99.8%.

Example 1.2

The lactic acid was produced by fermentation according to the method of Example 1.1, except that the *Lactobacillus rhamnosus* strain CGMCC No. 19507 were replaced with *Lactobacillus rhamnosus* strain CGMCC No. 19508, as a result, when the *Lactobacillus rhamnosus* strain CGMCC No. 19508 were fermented at 48° C. under the shake flask level of 200 mL, the lactic acid content in the fermentation broth obtained by fermenting the *Lactobacillus rhamnosus* strain for 48 hours was 215.3 g/L, the conversion rate of the glucose-lactic acid was 96.5%, and the optical purity of L-lactic acid was 99.5%.

Comparative Example 1.1

The lactic acid was produced by fermentation according to the method of Example 1.1, except that the *Lactobacillus rhamnosus* strain CGMCC No. 19507 were replaced with the *Lactobacillus rhamnosus* strain CGMCC No. 16834 (the strains were disclosed in CN109628339A);

As a result, the content of lactic acid in the obtained fermentation broth was 157 g/L, and the optical purity of L-lactic acid was 99%.

As can be seen from the results of Examples 1.1-1.2 and Comparative Example 1.1, *Lactobacillus rhamnosus* strain CGMCC No. 19507 and *Lactobacillus rhamnosus* strain CGMCC No. 19508 are superior to *Lactobacillus rhamnosus* strain CGMCC No. 16834 in terms of L-lactic acid yield and optical purity of the product. Therefore, the present disclosure provides a novel production strain with low fermentation cost, environmental friendliness, high L-lactic acid production speed and high optical purity of the product, and provides an excellent potential choice for industrial microbial fermentation and production of the L-lactic acid.

Examples 2.1 to 2.7 and Comparative Examples 2.1 to 2.2

These examples are used for illustrating the method of preparing D-lactic acid by fermentation according to the present disclosure. Wherein:

The dry matter content refers to a percentage of the mass of a test sample dried at about 130° C. for 40 min relative to the mass of the sample before the drying process.

The starch milk used was the starch milk from the COFCO Biochemical Energy (Yushu) Co., Ltd. The $Ca(OH)_2$ content in the lime milk was 20 wt %. The amylase was as follows: a compound enzyme system consisting of the high-temperature resistant alpha-amylase, beta-amylase and isoamylase of the Novozymes (China) Biotechnology Co., Ltd. with a weight ratio of 1:0.1:0.2. The saccharifying enzyme was AMG 300 L of Novozymes (China) Biotechnology Co., Ltd. The corn steep liquor was concentrated corn steep liquor from the COFCO Biochemical Energy (Yushu) Co., Ltd. The pure glucose was purchased from the Sinopharm Chemical Reagent Co., Ltd.

The fermentation tank used herein was a 100 L fermentation tank with a model number BIOTECH-100JS manufactured by the Shanghai Baoxing Bio-Engineering Equipment Co., Ltd.

Unless otherwise specified in the present disclosure, the adopted fermentation strains were *Lactobacillus plantarum* under accession number CGMCC No. 16835 (see CN109504630A), the *Lactobacillus plantarum* strains were preserved in an ultra-low temperature refrigerator at −80° C., and the glycerol tube was activated and re-cultured once every 1-3 months.

The content of D-lactic acid was measured by the High Performance Liquid Chromatography (HPLC) under the conditions including: the chromatographic column was aminex HPX-87H Column 300×7.8 mm; the column temperature was 55° C.; the mobile phase was 0.005M sulfuric acid; the flow rate was 0.5 mL/min; the sample size was 20 μL, differential refractive index detector.

Example 2.1

Preparing starch sugar: 6 g of amylase (corresponding to 200 U/kg of dry starch basis) was added into 30 kg of starch milk (wherein the dry content of starch was 40% by weight) having a pH of 5.8, the mixture was subjected to a spray liquefaction with steam at 110° C. (the time was about 4 s), then subjected to flash evaporation (pressure difference was 0.08±0.02 MPa), and a heat preservation at 95° C. for 60 min. The temperature was lowered to 60° C. through heat exchange to obtain a liquefied liquid. The pH was adjusted to 5, the diastase with a weight of 0.5% relative to the starch dry basis (equivalent to 1000 U/kg starch dry basis) was added, the mixture was stirred uniformly, and subjected to heat preservation at 60° C. for 24 h to obtain saccharified solution with a DE value of 99%.

Mixing materials in a fermentation tank: the saccharified liquid was directly added into a fermentation tank, and the sterilized corn steep liquor was added, the added amount of the sterilized corn steep liquor enabled the content of nitrogen in the fermentation broth to be 3 g/L, the content of glucose in the fermentation broth was controlled to be 190 g/L (such that the content of the carbon element in the fermentation broth was 76 g/L). The lime milk corresponding to 20% weight of the fermentation broth was added for controlling pH of the fermentation system to be about 6±0.2, it was not required to monitor the pH, the fermentation temperature was controlled to be 40±3° C., and the rotation speed of stirring was 100 rpm.

Fermentation: the well-cultivated seed solution with the $OD_{600}=10$ was inoculated into a fermentation tank at the inoculation amount corresponding to 10% of the fermentation broth volume, and was subjected to cultivation until exhaustion of the glucose.

Results: the fermentation period was 50 h, the total glucose-lactic acid conversion rate was 99%, and the yield of the D-lactic acid reached 188 g/L.

Example 2.2

Preparing starch sugar: 6 g of amylase (corresponding to 200 U/kg of dry starch basis) was added into 30 kg of starch milk (wherein the dry content of starch was 40% by weight) having a pH of 5.8, the mixture was subjected to a spray liquefaction with steam at 110° C. (the time was about 2 s), then subjected to flash evaporation (pressure difference was 0.08±0.02 MPa), and a heat preservation at 95° C. for 90 min. The temperature was lowered to 60° C. through heat exchange to obtain a liquefied liquid. The pH was adjusted to 5, the diastase with a weight of 0.4% relative to the starch dry basis (equivalent to 800 U/kg starch dry basis) was added, the mixture was stirred uniformly, and subjected to heat preservation at 60° C. for 24 h to obtain saccharified solution with a DE value of 96%.

Mixing materials in a fermentation tank: the saccharified liquid was directly added into a fermentation tank, and the sterilized corn steep liquor was added, the added amount of the sterilized corn steep liquor enabled the content of nitrogen in the fermentation broth to be 3 g/L, the content of glucose in the fermentation broth was controlled to be 190 g/L (such that the content of the carbon element in the fermentation broth was 76 g/L). The lime milk corresponding to 25% weight of the fermentation broth was added for controlling pH of the fermentation system to be about 6.2±0.2, it was not required to monitor the pH, the fermentation temperature was controlled to be 40±3° C., and the rotation speed of stirring was 100 rpm.

Fermentation: the well-cultivated seed solution with the $OD_{600}$=10 was inoculated into a fermentation tank at the inoculation amount corresponding to 10% of the fermentation broth volume, and was subjected to cultivation until exhaustion of the glucose.

Results: the fermentation period was 48 h, the glucose-lactic acid conversion rate was 95%, and the yield of the D-lactic acid reached 180 g/L.

Example 2.3

Preparing starch sugar: 6 g of amylase (corresponding to 200 U/kg of dry starch basis) was added into 30 kg of starch milk (wherein the dry content of starch was 30% by weight) having a pH of 5.8, the mixture was subjected to a spray liquefaction with steam at 110° C. (the time was about 3 s), then subjected to flash evaporation (pressure difference was 0.08±0.02 MPa), and a heat preservation at 95° C. for 60 min. The temperature was lowered to 60° C. through heat exchange to obtain a liquefied liquid. The pH was adjusted to 5, the diastase with a weight of 0.5% relative to the starch dry basis (equivalent to 1000 U/kg starch dry basis) was added, the mixture was stirred uniformly, and subjected to heat preservation at 60° C. for 24 h to obtain saccharified solution with a DE value of 99%.

Mixing materials in a fermentation tank: the saccharified liquid was directly added into a fermentation tank, and the sterilized corn steep liquor was added, the added amount of the sterilized corn steep liquor enabled the content of nitrogen in the fermentation broth to be 3 g/L, the content of glucose in the fermentation broth was controlled to be 160 g/L (such that the content of the carbon element in the fermentation broth was 64 g/L). The lime milk corresponding to 25% weight of the fermentation broth was added for controlling pH of the fermentation system to be about 6.2±0.2, it was not required to monitor the pH, the fermentation temperature was controlled to be 40±3° C., and the rotation speed of stirring was 100 rpm.

Fermentation: the well-cultivated seed solution with the $OD_{600}$=10 (corresponding to 3.33 dry cell weight/L) was inoculated into a fermentation tank at the inoculation amount corresponding to 10% of the fermentation broth volume, and was subjected to cultivation until exhaustion of the glucose.

Results: the fermentation period was 44 h, the glucose-lactic acid conversion rate was 99%, and the yield of the D-lactic acid reached 158 g/L.

Example 2.4

Preparing starch sugar: 3 g of amylase (corresponding to 100 U/kg of dry starch basis) was added into 30 kg of starch milk (wherein the dry content of starch was 40% by weight) having a pH of 5.8, the mixture was subjected to a spray liquefaction with steam at 100° C. (the time was about 1 s), then subjected to flash evaporation (pressure difference was 0.08±0.02 MPa), and a heat preservation at 80° C. for 90 min. The temperature was lowered to 60° C. through heat exchange to obtain a liquefied liquid. The pH was adjusted to 5, the diastase with a weight of 0.5% relative to the starch dry basis (equivalent to 1000 U/kg starch dry basis) was added, the mixture was stirred uniformly, and subjected to heat preservation at 55° C. for 24 h to obtain saccharified solution with a DE value of 95%.

Mixing materials in a fermentation tank: the saccharified liquid was directly added into a fermentation tank, and the sterilized corn steep liquor was added, the added amount of the sterilized corn steep liquor enabled the content of nitrogen in the fermentation broth to be 3 g/L, the content of glucose in the fermentation broth was controlled to be 190 g/L (such that the content of the carbon element in the fermentation broth was 76 g/L). The lime milk corresponding to 18% weight of the fermentation broth was added for controlling pH of the fermentation system to be about 5.8±0.5, it was not required to monitor the pH, the fermentation temperature was controlled to be 38±1° C., and the rotation speed of stirring was 50 rpm.

Fermentation: the well-cultivated seed solution with the $OD_{600}$=10 was inoculated into a fermentation tank at the inoculation amount corresponding to 10% of the fermentation broth volume, and was subjected to cultivation until exhaustion of the glucose.

Results: the fermentation period was 52 h, the glucose-lactic acid conversion rate was 95%, and the yield of the D-lactic acid reached 180 g/L.

Example 2.5

Preparing starch sugar: 6 g of amylase (corresponding to 200 U/kg of dry starch basis) was added into 30 kg of starch milk (wherein the dry content of starch was 40% by weight) having a pH of 5.8, the mixture was subjected to a spray liquefaction with steam at 120° C. (the time was about 4 s), then subjected to flash evaporation (pressure difference was 0.08±0.02 MPa), and a heat preservation at 100° C. for 90 min. The temperature was lowered to 65° C. through heat exchange to obtain a liquefied liquid. The pH was adjusted to 3, the diastase with a weight of 1% relative to the starch dry basis (equivalent to 2000 U/kg starch dry basis) was added, the mixture was stirred uniformly, and subjected to heat preservation at 60° C. for 24 h to obtain saccharified solution with a DE value of 98%.

Mixing materials in a fermentation tank: the saccharified liquid was directly added into a fermentation tank, and the sterilized corn steep liquor was added, the added amount of the sterilized corn steep liquor enabled the content of nitrogen in the fermentation broth to be 3 g/L, the content of glucose in the fermentation broth was controlled to be 160 g/L (such that the content of the carbon element in the fermentation broth was 64 g/L). The lime milk corresponding to 25% weight of the fermentation broth was added for controlling pH of the fermentation system to be about 6.2±0.3, it was not required to monitor the pH, the fermentation temperature was controlled to be 44±1° C., and the rotation speed of stirring was 150 rpm.

Fermentation: the well-cultivated seed solution with the $OD_{600}$=10 was inoculated into a fermentation tank at the inoculation amount corresponding to 10% of the fermentation broth volume, and was subjected to cultivation until exhaustion of the glucose.

Results: the fermentation period was 47 h, the glucose-lactic acid conversion rate was 96%, and the yield of the D-lactic acid reached 154 g/L.

Example 2.6

The D-lactic acid was prepared with the method of Example 2.1, except that the sodium citrate was used as the neutralizing agent in the fermentation process, the added amount and the addition mode were as follows: the 10 wt % sodium citrate solution was continuously fed into the fermentation system to control the pH of the fermentation system at 6.

Results: the fermentation period was 48 h, the glucose-lactic acid conversion rate was 90%, and the yield of the D-lactic acid reached 171 g/L.

Example 2.7

The D-lactic acid was prepared with the method of Example 2.1, except that sodium hydroxide was used as the neutralizing agent in the fermentation process, the added amount and the addition mode were as follows: 4 wt % sodium hydroxide solution was continuously fed into the fermentation system to control the pH of the fermentation system at 6±0.2.

As a result: the fermentation period is 38 h, the glucose-lactic acid conversion rate is 100%, and the D-lactic acid yield reaches 160 g/L.

Example 2.8

The D-lactic acid was prepared with the method of Example 2.1, except that the preparation of the saccharification liquid was carried out by using the following method:

2.25 g of amylase (corresponding to 200 U/kg of dry starch basis) was added into 11.25 kg of starch milk (wherein the dry content of starch was 15% by weight) having a pH of 5.8, the mixture was subjected to a spray liquefaction with steam at 120° C. (the time was about 4 s), then subjected to flash evaporation (pressure difference was 0.08±0.02 MPa), and a heat preservation at 100° C. for 90 min. The temperature was lowered to 65° C. through heat exchange to obtain a liquefied liquid. The pH was adjusted to 3, the diastase with a weight of 1% relative to the starch dry basis (equivalent to 2000 U/kg starch dry basis) was added, the mixture was stirred uniformly, and subjected to heat preservation at 65° C. for 20 h to obtain saccharified solution with a DE value of 97%.

Results: the fermentation period was 45 h, the total glucose-lactic acid conversion rate was 96%, and the yield of the D-lactic acid reached 155 g/L.

Comparative Example 2.1

The D-lactic acid was prepared with the method of Example 2.1, except that the pure glucose solution was used for replacing the starch sugar as the carbon source.

Results: the fermentation period was 44 h, the glucose-lactic acid conversion rate was 100%, and the yield of the D-lactic acid reached 190 g/L.

Comparative Example 2.2

The D-lactic acid was prepared with the method of Example 2.1, except that *Lactobacillus rhamnosus* (CGMCC No. 16834, published in CN 109628339A) was used as the fermentation strains.

Results: the fermentation period was 80 h, the glucose-lactic acid conversion rate was 12%, and the yield of the D-lactic acid reached 19 g/L.

Comparative Example 2.3

The D-lactic acid was prepared with the method of Example 2.1, except that the stirring speed was controlled to be 180 rpm, and the 4 wt % sodium hydroxide solution was continuously fed into the fermentation system to control the pH of the fermentation system to be 5.5±0.2.

Results: the fermentation period was 63 h, the total glucose-lactic acid conversion rate was 83%, and the yield of the D-lactic acid reached 133 g/L.

Comparative Example 2.4

The D-lactic acid was prepared with the method of Example 2.1, except that the well-cultivated seed solution with the $OD_{600}$=10 was inoculated into a fermentation tank at the inoculation amount corresponding to 20% of the fermentation broth volume, and the stirring speed was controlled at 180 rpm.

Results: the fermentation period was 39 h, the total glucose-lactic acid conversion rate was 88%, and the yield of the D-lactic acid reached 141 g/L.

Comparative Example 2.5

The D-lactic acid was prepared with the method of Example 2.1, except that the saccharified solution was added in an amount such that the carbon content in the fermentation broth was 50 g/L, and the 4 wt % sodium hydroxide solution was continuously fed into the fermentation system to control the pH of the fermentation system to be 5±0.2.

Results: the fermentation period was 38 h, the total glucose-lactic acid conversion rate was 93%, and the yield of the D-lactic acid reached 116 g/L.

As can be seen from the comparison of the results of Example 2.1 and Comparative Example 2.1, the method provided by the present disclosure adopts saccharified liquid (starch sugar) as the main carbon source for lactic acid fermentation, the fermentation period, the glucose-lactic acid conversion rate and the D-lactic acid yield of the method are not significantly different from those of the traditional fermentation process adopting glucose as the carbon source. But the method provided by the present disclosure has lower raw material cost than the traditional process. Taking the amounts of the saccharified solution and glucose used in Example 2.1 and Comparative Example 2.1 as examples, the cost of starch feedstock in Example 2.1 is about 60 yuan, and the cost of glucose feedstock in Comparative Example 2.1 is about 90 yuan. The production cost can be saved by 1,000,000 yuan per year from producing 1,000 tons of D-lactic acid per year in a D-lactic acid production workshop.

Although the Example 2.8 also utilizes saccharified solution (starch sugar) as a main carbon source for lactic acid fermentation, starch milk of low concentration is used as a raw material in the starch sugar production process. Compared with the method of Example 2.1, the method of obtaining the saccharified solution by liquefying the starchy raw material with high-concentration 30 wt % or more can greatly shorten the time for treating the raw material, thereby improving the efficiency of pretreating the raw material. When the method is applied to lactic acid fermentation production, the operation cost of raw material pretreatment can be reduced, the overall production cost is decreased, and the production efficiency is improved.

According to the comparison of the results of Example 2.1 and the Comparative Example 2.3-2.5, the purposes of shortening the fermentation period, reducing the production cost and improving the saccharide-acid conversion rate and the production intensity can be fulfilled only under the lactic acid fermentation conditions provided by the present disclosure in combination with the method provided by the present disclosure.

Examples 3.1 to 3.7 and Comparative Examples 3.1 to 3.6

These examples are used for illustrating the fermentative preparation of lactic acid according to the present disclosure. Wherein:

Unless otherwise specified in the present disclosure, the adopted fermentation strains were *Pediococcus acidilactici* under accession number CGMCC No. 16833 (particularly refer to CN109536409A), the *Pediococcus acidilactici* strains were preserved in an ultra-low temperature refrigerator at −80° C., and the glycerol tube was activated and re-cultured once every 1-3 months.

In the following examples, the preparation method of the fresh *Pediococcus acidilactici* seed solution was as follows: inoculating the low-temperature frozen *Pediococcus acidilactici* strain in the MRS liquid culture medium, wherein the appropriate inoculation amount of the strains was 1-10 vol %. The strains were cultured overnight under the conditions consisting of 40±2° C. and the rotation speed of 170±30 rpm to obtain a fresh seed solution.

The preparation method of the MRS liquid culture medium comprising: 200 g/L of glucose, 5 g/L of yeast extract, 10 mL/L of corn steep liquor with solid content of 40%, 2 g/L of sodium acetate, 0.5 g/L of $KH_2PO_4$, 0.5 g/L of $MgSO_4.7H_2O$, 0.25 g/L of $MnSO_4.H_2O$ and 1 mL/L of tween.

In the following examples, the preparation method of the cellulose hydrolysate comprises: the cellulose hydrolysate was prepared by subjecting the cellulose raw materials to crushing, acidolysis by sulfuric acid (the concentration is 1.6 wt %), steam explosion (under the condition of 160° C. for 40 min) and enzymolysis by cellulase (Cellic CTec3 cellulose complex enzyme produced by the Novozymes (China) Biotechnology Co., Ltd.), and then subjecting to extrusion with filter cloth. The specific preparation method comprises the following steps:

1. The lignocellulose raw materials were crushed to the particles having a granularity of 50±10 mm, the crushed lignocellulose raw materials were put into a screw feeder, subjected to extruding and dehydrating until the dry matter content was 40±5 wt %, a compact material plug was formed, the compact material plug may resist the leakage of steam in a container while ensuring that the cellulose raw material was continuously introduced into the treatment container;

2. After the material plug was treated by the screw feeder, sulfuric acid was mixed into the material plug with an added amount of 2±1 wt % relative to the weight of the material plug, the material plug and the sulfuric acid were mixed in an acid mixing tank to obtain an acidic cellulose raw materials;

3. The acidic cellulose materials were contacted with steam in a cooking treatment container under the conditions consisting of a pressure of 0.6 MPa and a time of 50 min. The cellulose materials were then discharged from the container in a continuous discharge manner;

4. The obtained product was subjected to washing with water, the pH was adjusted to 5±0.1, the temperature was heated to 50° C., cellulase was added, wherein the addition amount of the cellulase was 0.15 g based on the dry weight of each gram of the product. The obtained product was subjected to heat preservation at 50° C. and stirring for 72 h to obtain the cellulase enzymatic hydrolysate.

In the following examples, the corn steep liquor was concentrated corn steep liquor from the COFCO Biochemical Energy (Yushu) Co., Ltd., the $KH_2PO_4$, $MgSO_4.7H_2O$, and $MnSO_4.H_2O$ were purchased from Sinopharm Chemical Reagent Co., Ltd. The cellulase was a Cellic CTec3 cellulose complex enzyme product purchased from the Novozymes (China) Biotechnology Co., Ltd. Unless otherwise specified, the fermentation tank used herein was a 2-5 L fermentation tank with the model Bio-Stat commercially available from the Sartorius AG.

In the following examples, the calculation method of the saccharide-lactic acid conversion rate was as follows: total weight of lactic acid at the end of fermentation/total weight of glucose and pentose at the initial stage. The pentose comprises: xylose and arabinose. The glucose content was measured as follows: a biosensor analyzer (a biosensor analyzer with the model SBA-40D from the Biology Institute of Shandong Academy of Science). The high temperature sterilization was carried out at 120° C. for 20 min.

In the following examples, the method for measuring the content of pentose was high performance liquid chromatography (HPLC) method, and the conditions can be referred from LIU Jianwei, et al., "Detection of Composition of Xylose Mother Liquor by HPLC", Journal of Anhui Agriculture Science, Vol. 37 (5), pp. 1881-1882.

In the following examples, the lactic acid was measured by high performance liquid chromatography under the following conditions:

Instrument device: Agilent Technologies 1260 Infinity II;
Detector: RID;
Separation column: Aminex HPX-87H Column 300×7.8 mm; Column temperature: 55° C.
Mobile phase: 0.005M sulfuric acid;
Flow rate: 0.5 mL/min;
Sample injection amount: 20 µL;
The retention time of lactic acid was about 14 min.

Example 3.1

2 L fermentation tank was used for the small-scale pilot test.

Preparation of a culture medium: the cellulose raw material was straw, 30 vol % of cellulase enzymatic hydrolysate was added and used as a carbon source, 8 vol % of corn steep liquor was added and used as a nitrogen source; 1 g/L of inorganic salt $KH_2PO_4$, 0.5 g/L $MgSO_4.7H_2O$, 0.25 g/L $MnSO_4.H_2O$ were further added, the balance was water, the mixture was sterilized at high temperature and cooled to 40° C. for standby. Wherein the content of the pentose was 44 g/L, and the content of the glucose was 100 g/L.

Pre-fermentation: 1.2 L of culture medium was added into a fermentation tank, the fresh *Pediococcus acidilactici* seed solution was inoculated into the fermentation tank according to the inoculation amount of 5 vol % (the concentration was $OD_{600}=0.45$), the temperature was controlled at 42° C., the fermentation rotation speed was 150 r/min, the air was introduced by starting trace aeration, the ventilation amount was 0.05 vvm in terms of oxygen. Sodium hydroxide solution (with concentration 4 wt %) was used as a neutralizing agent, the solution was fed-batch during the fermentation process and the pH was controlled at 6.

Continuous fermentation: when the content of *Pediococcus acidilactici* in the fermentation system reached $OD_{600}=10$, the aeration was stopped, the lactic acid fermentation process was continued under the conditions consisting of a temperature of 42° C., the fermentation rotation speed of 150 r/min, the sodium hydroxide solution (with concentration of 4 wt %) was taken as a neutralizing agent, the solution was fed-batch during the fermentation process and the pH was controlled at 6.

Results: the total fermentation time was 75 h, wherein the pre-fermentation time was 15 h, and the continuous fermentation time was 60 h. After the fermentation was finished, there was not obvious glucose residue, the consumption of pentose was 48%. The total saccharide-lactic acid conversion rate reached 78%, and the lactic acid yield may reach 95 g/L.

Example 3.2

2 L fermentation tank was used for the small-scale pilot test.

Preparation of a culture medium: the cellulose raw material was straw, 10 vol % of cellulase enzymatic hydrolysate was added and used as a carbon source, 3 vol % of corn steep liquor was added and used as a nitrogen source; 1 g/L of inorganic salt $KH_2PO_4$, 0.5 g/L $MgSO_4.7H_2O$, 0.25 g/L $MnSO_4.H_2O$ were further added, the balance was water, the mixture was sterilized at high temperature and cooled to 40° C. for standby. Wherein the content of the pentose was 15 g/L, and the content of the glucose was 36 g/L.

Pre-fermentation: 1.2 L of culture medium was added into a fermentation tank, the fresh *Pediococcus acidilactici* seed solution was inoculated into the fermentation tank according to the inoculation amount of 1 vol % (the concentration was $OD_{600}=0.09$), the temperature was controlled at 37° C., the fermentation rotation speed was 150 r/min, the air was introduced by starting trace aeration, the ventilation amount was 0.05 vvm in terms of oxygen. Sodium hydroxide solution (with concentration 4 wt %) was used as a neutralizing agent, the solution was fed-batch during the fermentation process and the pH was controlled at 6.2.

Continuous fermentation: when the content of *Pediococcus acidilactici* in the fermentation system reached $OD_{600}=10$, the aeration was stopped, the lactic acid fermentation process was continued under the conditions consisting of a temperature of 37° C., the fermentation rotation speed of 150 r/min, the sodium hydroxide solution (with concentration of 4 wt %) was taken as a neutralizing agent, the solution was fed-batch during the fermentation process and the pH was controlled at 6.2.

Results: the total fermentation time was 48 h, wherein the pre-fermentation time was 8 h, and the continuous fermentation time was 40 h. After the fermentation was finished, there was not obvious glucose residue, the consumption of pentose was 53%. The total saccharide-lactic acid conversion rate reached 80%, and the lactic acid yield may reach 35 g/L.

Example 3.3

2 L fermentation tank was used for the small-scale pilot test.

Preparation of a culture medium: the cellulose raw material was straw, 20 vol % of cellulase enzymatic hydrolysate was added and used as a carbon source, 5 vol % of corn steep liquor was added and used as a nitrogen source; 1 g/L of inorganic salt $KH_2PO_4$, 0.5 g/L $MgSO_4.7H_2O$, 0.25 g/L $MnSO_4.H_2O$ were further added, the balance was water, the mixture was sterilized at high temperature and cooled to 40° C. for standby. Wherein the content of the pentose was 30 g/L, and the content of the glucose was 70 g/L.

Pre-fermentation: 1.2 L of culture medium was added into a fermentation tank, the fresh *Pediococcus acidilactici* seed solution was inoculated into the fermentation tank according to the inoculation amount of 3 vol % (the concentration was $OD_{600}=0.27$), the temperature was controlled at 39° C., the fermentation rotation speed was 150 r/min, the air was introduced by starting trace aeration, the ventilation amount was 0.05 vvm in terms of oxygen. Sodium hydroxide solution (with concentration 4 wt %) was used as a neutralizing agent, the solution was fed-batch during the fermentation process and the pH was controlled at 6.5.

Continuous fermentation: when the content of *Pediococcus acidilactici* in the fermentation system reached $OD_{600}=10$, the aeration was stopped, the lactic acid fermentation process was continued under the conditions consisting of a temperature of 39° C., the fermentation rotation speed of 100 r/min, the sodium hydroxide solution (with concentration of 4 wt %) was taken as a neutralizing agent, the solution was fed-batch during the fermentation process and the pH was controlled at 6.5.

Results: the total fermentation time was 66 h, wherein the pre-fermentation time was 15 h, and the continuous fermentation time was 51 h. After the fermentation was finished, there was not obvious glucose residue, the consumption of pentose was 47%. The total saccharide-lactic acid conversion rate reached 79%, and the lactic acid yield may reach 66 g/L.

Example 3.4

5 L fermentation tank was used for the small-scale pilot test.

Preparation of a culture medium: the cellulose raw material was oat hull, 15 vol % of cellulase enzymatic hydrolysate was added and used as a carbon source, 4 vol % of corn steep liquor was added and used as a nitrogen source; 1 g/L of inorganic salt $KH_2PO_4$, 0.5 g/L $MgSO_4.7H_2O$, 0.25 g/L $MnSO_4.H_2O$ were further added, the balance was water, the mixture was sterilized at high temperature and cooled to 45° C. for standby. Wherein the content of the pentose was 20 g/L, and the content of the glucose was 55 g/L.

Pre-fermentation: 3.0 L of culture medium was added into a fermentation tank, the fresh *Pediococcus acidilactici* seed solution was inoculated into the fermentation tank according to the inoculation amount of 7 vol % (the concentration was $OD_{600}=0.63$), the temperature was controlled at 45° C., the fermentation rotation speed was 50 r/min, the air was introduced by starting trace aeration, the ventilation amount was 0.008 vvm in terms of oxygen. Sodium hydroxide solution (with concentration 4 wt %) was used as a neutralizing agent, the solution was fed-batch during the fermentation process and the pH was controlled at 5.3.

Continuous fermentation: when the content of *Pediococcus acidilactici* in the fermentation system reaches $OD_{600}$=10, the aeration was stopped, the lactic acid fermentation process was continued under the conditions consisting of a temperature of 45° C., the fermentation rotation speed of 70 r/min, the ammonium hydroxide solution (with concentration of 14 wt %) was taken as a neutralizing agent, the solution was fed-batch during the fermentation process and the pH was controlled at 5.3.

Results: the total fermentation time was 55 h, wherein the pre-fermentation time was 12 h, and the continuous fermentation time was 43 h. After the fermentation was finished, there was not obvious glucose residue, the consumption of pentose was 51%. The total saccharide-lactic acid conversion rate reached 78%, and the lactic acid yield may reach 51 g/L.

Example 3.5

2 L fermentation tank was used for the small-scale pilot test.

Preparation of a culture medium: the cellulose raw material was corncob, 25 vol % of cellulase enzymatic hydrolysate was added and used as a carbon source, 7 vol % of corn steep liquor was added and used as a nitrogen source; 1 g/L of inorganic salt $KH_2PO_4$, 0.5 g/L $MgSO_4.7H_2O$, 0.25 g/L $MnSO_4.H_2O$ were further added, the balance was water, the mixture was sterilized at high temperature and cooled to 40° C. for standby. Wherein the content of the pentose was 35 g/L, and the content of the glucose was 85 g/L.

Pre-fermentation: 1.2 L of culture medium was added into a fermentation tank, the fresh *Pediococcus acidilactici* seed solution was inoculated into the fermentation tank according to the inoculation amount of 5 vol % (the concentration was $OD_{600}$=0.45), the temperature was controlled at 40° C., the fermentation rotation speed was 120 r/min, the air was introduced by starting trace aeration, the ventilation amount was 0.01 vvm in terms of oxygen. Ammonium hydroxide solution (with concentration 12 wt %) was used as a neutralizing agent, the solution was fed-batch during the fermentation process and the pH was controlled at 6.5.

Continuous fermentation: when the content of *Pediococcus acidilactici* in the fermentation system reaches $OD_{600}$=10, the aeration was stopped, the lactic acid fermentation process was continued under the conditions consisting of a temperature of 40° C., the fermentation rotation speed of 120 r/min, the sodium hydroxide solution (with concentration of 4 wt %) was taken as a neutralizing agent, the solution was fed-batch during the fermentation process and the pH was controlled at 6.5.

Results: the total fermentation time was 75 h, wherein the pre-fermentation time was 18 h, and the continuous fermentation time was 57 h. After the fermentation was finished, there was not obvious glucose residue, the consumption of pentose was 52%. The total saccharide-lactic acid conversion rate reached 81%, and the lactic acid yield may reach 84 g/L.

Example 3.6

100 L fermentation tank was used for the pilot plant level test, wherein the fermentation tank is the fermentation tank with a volume of 100 L and a model number BIOTECH-100JS manufactured by the Shanghai Baoxing Bio-Engineering Equipment Co., Ltd.

Preparation of a culture medium: the cellulose raw material was straw, 20 vol % of cellulase enzymatic hydrolysate was added and used as a carbon source, 6 vol % of corn steep liquor was added and used as a nitrogen source; 1 g/L of inorganic salt $KH_2PO_4$, 0.5 g/L $MgSO_4.7H_2O$, 0.25 g/L $MnSO_4.H_2O$ were further added, the balance was water, the mixture was sterilized at high temperature and cooled to 45° C. for standby. Wherein the content of the pentose was 30 g/L, and the content of the glucose was 70 g/L.

Pre-fermentation: 57 L of culture medium was added into a fermentation tank, the fresh *Pediococcus acidilactici* seed solution was inoculated into the fermentation tank according to the inoculation amount of 5 vol % (the concentration was $OD_{600}$=0.45), the temperature was controlled at 42° C., the fermentation rotation speed was 80 r/min, the air was introduced by starting trace aeration, the ventilation amount was 0.01 vvm in terms of oxygen. Ammonium hydroxide solution (with concentration 14 wt %) was used as a neutralizing agent, the solution was fed-batch during the fermentation process and the pH was controlled at 6.0.

Continuous fermentation: when the content of *Pediococcus acidilactici* in the fermentation system reached $OD_{600}$=10, the aeration was stopped, the lactic acid fermentation process was continued under the conditions consisting of a temperature of 42° C., the fermentation rotation speed of 50 r/min, the ammonium hydroxide solution (with concentration of 14 wt %) was taken as a neutralizing agent, the solution was fed-batch during the fermentation process and the pH was controlled at 6.

Results: the total fermentation time was 62 h, wherein the pre-fermentation time was 14 h, and the continuous fermentation time was 48 h. After the fermentation was finished, there was not obvious glucose residue, the consumption of pentose was 46%. The total saccharide-lactic acid conversion rate reached 78%, and the lactic acid yield may reach 65 g/L.

Example 3.7

The lactic acid was prepared according to the method of Example 3.1, except that a sodium citrate solution (with concentration 11 wt %) was used as a neutralizing agent.

Results: the total fermentation time was 80 h, wherein the pre-fermentation time was 20 h, and the continuous fermentation time was 60 h. After the fermentation was finished, there was not obvious glucose residue, the consumption of pentose was 49%. The total saccharide-lactic acid conversion rate reached 80%, and the lactic acid yield may reach 97 g/L.

Example 3.8

The lactic acid was prepared according to the method of Example 3.1, except that the fermentation was continued in the following manner:

When the content of *Pediococcus acidilactici* in the fermentation system reached $OD_{600}$=8, the aeration was stopped, the lactic acid fermentation process was continued under the conditions consisting of a temperature of 42° C., the fermentation rotation speed of 150 r/min, the sodium hydroxide solution (with concentration of 4 wt %) was taken as a neutralizing agent, the solution was fed-batch during the fermentation process and the pH was controlled at 6.

Results: the total fermentation time was 70 h, wherein the pre-fermentation time was 12 h, and the continuous fermentation time was 58 h. After the fermentation was finished, there was not obvious glucose residue, the consumption of pentose was 48%. The total saccharide-lactic acid conversion rate reached 72%, and the lactic acid yield may reach 90 g/L.

Example 3.9

The lactic acid was prepared according to the method of Example 3.1, except that the fermentation was continued in the following manner:
when the content of *Pediococcus acidilactici* in the fermentation system reaches $OD_{600}$=13, the aeration was stopped, the lactic acid fermentation process was continued under the conditions consisting of a temperature of 42° C., the fermentation rotation speed of 150 r/min, the sodium hydroxide solution (with concentration of 4 wt %) was taken as a neutralizing agent, the solution was fed-batch during the fermentation process and the pH was controlled at 6.
Results: the total fermentation time was 72 h, wherein the pre-fermentation time was 16 h, and the continuous fermentation time was 56 h. After the fermentation was finished, there was not obvious glucose residue, the consumption of pentose was 50%. The total saccharide-lactic acid conversion rate reached 77%, and the lactic acid yield may reach 93 g/L.

Comparative Example 3.1

The lactic acid was prepared according to the method of Example 3.1, except that the anaerobic fermentation was used in the whole course, i.e., air was not introduced during the pre-fermentation and the continuous fermentation processes.
Results: the total fermentation time was 90 h. After the fermentation was finished, there was not obvious glucose residue, the consumption of pentose was 42%. The total saccharide-lactic acid conversion rate reached 73%, and the lactic acid yield may reach 86 g/L.

Comparative Example 3.2

The lactic acid was prepared according to the method of Example 3.1, except that the aeration amount during the pre-fermentation process was 0.1 vvm in terms of oxygen.
Results: the total fermentation time was 72 h, wherein the pre-fermentation time was 12 h, and the continuous fermentation time was 60 h. After the fermentation was finished, there was not obvious glucose residue, the consumption of pentose was 52%. The total saccharide-lactic acid conversion rate reached 66%, and the lactic acid yield may reach 81 g/L.

Comparative Example 3.3

The lactic acid was prepared according to the method of Example 3.1, except that the inoculation amount of the inoculated *Pediococcus acidilactici* seed solution was 1 vol %.
Results: the total fermentation time was 90 h, wherein the pre-fermentation time was 20 h, and the continuous fermentation time was 70 h. After the fermentation was finished, there was not obvious glucose residue, the consumption of pentose was 33%. The total saccharide-lactic acid conversion rate reached 66%, and the lactic acid yield may reach 76 g/L.

Comparative Example 3.4

The lactic acid was prepared according to the method of Example 3.1, except that the fermentation was stopped when the consumption of pentose in the culture medium reached 60%.
Results: the total fermentation time was 120 h, wherein the pre-fermentation time was 15 h, and the continuous fermentation time was 105 h. After the fermentation was finished, there was not obvious glucose residue, the consumption of pentose was 60%. The total saccharide-lactic acid conversion rate reached 69%, and the lactic acid yield may reach 87 g/L.

Comparative Example 3.5

The lactic acid was prepared according to the method of Example 3.1, except that the *Pediococcus acidilactici* biomass $OD_{600}$ in the fermentation system after the pre-fermentation was not less than 20.
Results: the total fermentation time was 68 h, wherein the pre-fermentation time was 18 h, and the continuous fermentation time was 50 h. After the fermentation was finished, there was not obvious glucose residue, the consumption of pentose was 49%. The total saccharide-lactic acid conversion rate reached 66%, and the lactic acid yield may reach 80 g/L.

Comparative Example 3.6

The lactic acid was prepared according to the method of Example 3.1, except that air was introduced during both the pre-fermentation process and the continuous fermentation process, i.e. air was introduced in a mode of performing aeration in the whole course.
Results: the total fermentation time was 66 h, wherein the pre-fermentation time was 14 h, and the continuous fermentation time was 52 h. After the fermentation was finished, there was not obvious glucose residue, the consumption of pentose was 56%. The total saccharide-lactic acid conversion rate reached 54%, and the lactic acid yield may reach 67 g/L.

As can be seen by comparing the results of Example 3.1 with those of Comparative Example 3.1, a use of the preferred embodiment provided by the present disclosure, i.e. the mode of introducing air during the pre-fermentation stage, may results in the reduced total fermentation time and save the time cost in lactic acid production and application. In addition, each of the consumption of pentose, the saccharide-lactic acid conversion rate, and the yield of lactic acid in the fermentation culture medium is slightly increased, thus the production efficiency is improved.

As can be seen from the comparison of the results of Example 3.1 and those of Comparative Example 3.2, although the increase in the amount of introduced oxygen can slightly reduce the total fermentation time and the consumption of pentose in the culture medium, the saccharide-lactic acid conversion rate and the lactic acid yield are significantly reduced. It can be seen from the result that the increased consumption of pentose is not used for lactic acid fermentation, but supplying the growth of microbial cells, which is not beneficial to the production efficiency of lactic acid fermentation.

As indicated by the comparison of the results of Example 3.1 and Comparative Example 3.3, when the inoculation amount of *Pediococcus acidilactici* is lower than the preferable range of the inoculation amount, the total fermentation time during the lactic acid fermentation and production process is increased, each the consumption amount of pentose, the saccharide-lactic acid conversion rate and the lactic acid production amount in the culture medium is decreased. The overall production efficiency is reduced, which is not beneficial to industrial scale production and application.

It is demonstrated by the comparison of the results of Example 3.1 with those of Comparative Example 3.4, when the consumption amount of the pentose in the culture medium exceeds the preferable consumption amount range of the present disclosure, the saccharide-lactic acid conversion rate and the lactic acid yield do not increase correspondingly along with an increase of the total fermentation time. In addition, the overall production efficiency is low, which is not conducive to industrial scale production application.

As can be seen from a comparison of the results of Example 3.1 with those of Comparative Example 3.5, when there is an excessive amount of *Pediococcus acidilactici* in the fermentation system at the end of the pre-fermentation stage, the total fermentation time is slightly reduced, but the pre-fermentation time therein is increased accordingly, both the total saccharide-lactic acid conversion rate and the lactic acid yield are reduced, and the overall production efficiency is decreased. In combination with the result in regard to an increased consumption of pentose, it is likely that the nutrients in the fermentation system are mainly provided for growth of the thallus instead of the lactic acid production.

It is revealed from a comparison of the results of Example 3.1 with those of Comparative Example 3.6, both the total saccharide-lactic acid conversion rate and the lactic acid yield are slightly reduced although the fermentation time is decreased to some extent. According to the comparison of the consumption of pentose, under the condition of whole-course aeration, more nutrient components in the fermentation system are supplied for thallus growth instead of lactic acid production, such that the production efficiency is reduced, which is not conducive to the industrial scale production and application.

Examples 4.1 to 4.5 and Comparative Examples 4.1 to 4.2

These examples were used for illustrating the separation process of lactic acid associated with the present disclosure, wherein:

the lactic acid fermenting thallus was *Lactobacillus rhamnosus* with an accession number of CGMCC No. 16834 (which was disclosed in CN109628339A).

The rotary evaporator was purchased from Shanghai Yanrong biochemical instrument factory, with an instrument model of RE-52 AA.

The wiped film evaporator was purchased from UIC Company, with an instrument model of GmbH.

The content of lactic acid was measured by the high performance liquid chromatography.

The parameters for producing purified lactic acid in Examples and Comparative Examples were shown in Table 1.

Example 4.1

(1) The lactic acid fermentation broth (with the lactic acid content of 16.6 wt %) of *Lactobacillus rhamnosus* was sequentially subjected to solid-liquid separation and decoloration, wherein the decolorizing agent was activated carbon;

(2) The product obtained in the step (1) was subjected to ion exchange with the anion exchange resin (purchased from Xi'an Lanxiao Technology New Material Co., Ltd., with a model number LSD296) according to the volume ratio of 1:2, so as to obtain a lactic acid solution;

(3) The lactic acid concentrated solution obtained in the step (2) was subjected to vacuum concentration in a rotary evaporator, in order to obtain a lactic acid concentrated solution with the lactic acid content of 85 wt % and the water content of 15 wt %, wherein the vacuum concentration conditions included that the temperature was 40° C., and the vacuum degree was 0.7 mbar;

(4) the lactic acid concentrated solution obtained in the step (3) was subjected to a molecular distillation in a wiped film evaporator to obtain refined lactic acid S1 with the lactic acid content of 99 wt %, wherein the conditions of the wiped film evaporator comprise: the rotation speed of scraper was 70 r/min, the internal temperature of the steam clamp ferrule was 110° C., the feedstock flow rate was 10 mL/min, and the vacuum was 0.4 mbar.

Example 4.2

(1) The lactic acid fermentation broth (with the lactic acid content of 14.5 wt %) of *Lactobacillus rhamnosus* was sequentially subjected to solid-liquid separation and decoloration, wherein the decolorizing agent was activated carbon;

(2) The product obtained in the step (1) was subjected to ion exchange with the anion exchange resin (purchased from Xi'an Lanxiao Technology New Material Co., Ltd., with a model number LSA-700B) according to the volume ratio of 1:5, so as to obtain a lactic acid solution;

(3) The lactic acid concentrated solution obtained in the step (2) was subjected to vacuum concentration in a rotary evaporator, in order to obtain a lactic acid concentrated solution with the lactic acid content of 80 wt % and the water content of 20 wt %, wherein the vacuum concentration conditions included that the temperature was 60° C., and the vacuum degree was 0.8 mbar;

(4) the lactic acid concentrated solution obtained in the step (3) was subjected to a molecular distillation in a wiped film evaporator to obtain refined lactic acid S2 with the lactic acid content of 98 wt %, wherein the conditions of the wiped film evaporator comprise: the rotation speed of scraper was 90 r/min, the internal temperature of the steam clamp ferrule was 120° C., the feedstock flow rate was 12 mL/min, and the vacuum was 0.1 mbar.

Example 4.3

(1) The lactic acid fermentation broth (with the lactic acid content of 14.4 wt %) of *Lactobacillus rhamnosus* was sequentially subjected to solid-liquid separation and decoloration, wherein the decolorizing agent was activated carbon;

(2) The product obtained in the step (1) was subjected to ion exchange with the anion exchange resin (purchased from Xi'an Lanxiao Technology New Material Co., Ltd., with a model number D303) according to the volume ratio of 1:7, so as to obtain a lactic acid solution;

(3) The lactic acid concentrated solution obtained in the step (2) was subjected to vacuum concentration in a rotary evaporator, in order to obtain a lactic acid concentrated solution with the lactic acid content of 80 wt % and the water content of 20 wt %, wherein the vacuum concentration conditions included that the temperature was 30° C., and the vacuum degree was 0.8 mbar;

(4) the lactic acid concentrated solution obtained in the step (3) was subjected to a molecular distillation in a wiped film evaporator to obtain refined lactic acid S3 with the lactic acid content of 99 wt %, wherein the conditions of the wiped film evaporator comprise: the rotation speed of scraper was 100 r/min, the internal temperature of the steam clamp ferrule was 110° C., the feedstock flow rate was 10 mL/min, and the vacuum was 0.08 mbar.

Example 4.4

The separation of lactic acid was performed according to the method of Example 4.1, except that the lactic acid fermentation broth of *Lactobacillus rhamnosus* (with the lactic acid content 16.6 wt %) was replaced with a lactic acid-containing solution having a lactic acid content of 13.3 wt %, so as to obtain the refined lactic acid S4.

Example 4.5

The separation of lactic acid was performed according to the method of Example 4.1, except that the step (1) was omitted, that is, the lactic acid fermentation broth of *Lactobacillus rhamnosus* (with the lactic acid content 16.6 wt %) was directly subjected to ion exchange to obtain refined lactic acid S5.

Comparative Example 4.1

The lactic acid fermentation broth of *Lactobacillus rhamnosus* (with the lactic acid content 16.6 wt %) was separated according to the method disclosed in CN103724183A to obtain refined lactic acid D1.

Comparative Example 4.2

The separation of lactic acid was performed according to the method of Example 4.1, except that the step (3) was omitted, that is, the lactic acid concentrated solution obtained in the step (2) was directly subjected to molecular distillation, so as to obtain refined lactic acid D2.

The movable air compressor was purchased from Shanghai Guosha Compressor Co., Ltd., with a model number W1.5/20.

The liquid booster pump was commercially available from the Anhui Tenglong Pump and Valve Manufacturing Co., Ltd., with a model number CQB 32-25-125F.

A lactate detection method, which adopted a high performance liquid chromatography detection method as follows: chromatograph: Agilent Technologies 1260 Infinity II; detector: RID; separation column: Aminex HPX-87H Column 300×7.8 mm; mobile phase: 0.005M sulfuric acid; flow rate: 0.5 mL/min; sample injection amount: 20 μL; the retention time of lactate was within a range of 10-20 min.

The lactic acid fermentation strain was *Lactobacillus rhamnosus* with an accession number CGMCC No. 16834 (CN109628339A).

The preparation method of the lactate fermentation broth comprises the following steps: the *Lactobacillus* was inoculated into a fermentation culture medium containing a carbon source, a nitrogen source and other components to perform lactic acid fermentation, the temperature was controlled to within a range of 37-45° C. and the pH was controlled to within a range of 5.5-6.3 during the fermentation process, the stirring was performed at a low speed until a carbon source in the substrate was depleted, the fermentation was finished to obtain a fresh fermentation broth; wherein the content of lactate in the lactate fermentation broth was 150 g/L in terms of ammonium lactate.

Downstream treatment refers to concentration, i.e., cations and anions were initially removed by ion exchange, the water was then removed by molecular distillation.

The liquid volume, lactate content and lactate yield for the downstream treatment were shown in Table 2.

TABLE 1

|  | Lactic acid-containing solution | | Content of impurity in the lactic acid solution wt % | Lactic acid concentrated solution | | Content of lactic acid in the refined lactic acid, wt % |
| --- | --- | --- | --- | --- | --- | --- |
|  | Lactic acid content wt % | Impurity content wt % |  | Lactic acid content wt % | Water content wt % |  |
| Example 4.1 | 16.6 | 13.9 | 3.2 | 85 | 15 | 99 |
| Example 4.2 | 14.5 | 9.9 | 5.8 | 80 | 20 | 98 |
| Example 4.3 | 14.4 | 10.1 | 7.3 | 80 | 20 | 99 |
| Example 4.4 | 13.3 | 12.6 | 6.9 | 82 | 18 | 98 |
| Example 4.5 | 16.6 | 14.1 | 5.6 | 70 | 25 | 80 |
| Comparative Example 4.1 | 16.6 | 13.9 | 3.2 | 75 | 25 | 82 |
| Comparative Example 4.2 | 16.6 | 13.9 | 3.2 | — | — | 90 |

As can be seen from the data in Table 1, the method provided by the present disclosure is adopted to carry out ion exchange, vacuum concentration and molecular distillation treatment in regard to the lactic acid-containing solution, it is conducive to improving the content of lactic acid in refined lactic acid and increasing purity of the lactic acid.

Examples 5.1 to 5.6 and Comparative Examples 5.1 to 5.4

These examples were used for illustrating the method and system for separating lactate according to the present disclosure. Wherein The plate-and-frame filter was purchased from the Haining Yunfei Filter Equipment Co., Ltd., with a model number YF-100-1.

Example 5.1

(1) 1,000 L of lactate fermentation broth and 20 g of perlite were injected into a mixing tank with a stirring device in a separation unit, then subjected to stirring and mixing at the temperature of 20° C. and the rotation speed of 50 rpm until the perlite was completely suspended in the fermentation broth to obtain a mixed material;

(2) The mixed material was poured into a plate-and-frame filter by a booster pump, and subjected to filtering under the condition of stirring and a pressure of 0.2 MPa until the mixed material was completely filtered, and the booster pump was turned off, such that a first feed liquid and a filter cake were obtained, wherein the mesh number of filter cloth in the plate-and-frame filter was 800 meshes;

(3) After the filtering process was finished, the compressed air with a pressure of 0.15 MPa was introduced into a liquid inlet of the plate-and-frame filter in order to blow out lactate permeation liquid remained in the filter cake from the top until the blown-out liquid was very little and only a small amount of liquid foam was entrained in the compressed air, the first top blowing was stopped;

(4) After the first top blowing was finished, water was poured into a liquid inlet of the plate-and-frame filter until the water flow at an outlet was continuous, an inlet valve and an outlet valve were closed, a soaking process was performed for 60 min, a lactate residual liquid in the thallus cells was obtained after the soaking process with water was completed;

(5) Following completion of the water washing process, the compressed air with a pressure of 0.15 MPa was again introduced into the liquid inlet of the plate-and-frame filter to carry out a second top blowing, such that the water washing liquid in the filter cake was replaced;

(6) the mixed liquid consisting of the first material liquid, the lactate permeate liquid, the lactate residual liquid and the water washing liquid was subjected to a downstream treatment so as to obtain a lactate S1.

Example 5.2

(1) 1,000 L of lactate fermentation broth and 10 g of perlite were injected into a mixing tank with a stirring device in a separation unit, then subjected to stirring and mixing at the temperature of 30° C. and the rotation speed of 20 rpm until the perlite was completely suspended in the fermentation broth to obtain a mixed material;

(2) The mixed material was poured into a plate-and-frame filter by a booster pump, and subjected to filtering under the condition of stirring and a pressure of 0.3 MPa until the mixed material was completely filtered, and the booster pump was turned off, such that a first feed liquid and a filter cake were obtained, wherein the mesh number of filter cloth in the plate-and-frame filter was 500 meshes;

(3) After the filtering process was finished, the compressed air with a pressure of 0.1 MPa was introduced into a liquid inlet of the plate-and-frame filter in order to blow out lactate permeation liquid remained in the filter cake from the top until the blown-out liquid was very little and only a small amount of liquid foam was entrained in the compressed air, the first top blowing was stopped;

(4) After the first top blowing was finished, water was poured into a liquid inlet of the plate-and-frame filter until the water flow at an outlet was continuous, an inlet valve and an outlet valve were closed, a soaking process was performed for 30 min, a lactate residual liquid in the thallus cells was obtained after the soaking process with water was completed;

(5) Following completion of the water washing process, the compressed air with a pressure of 0.1 MPa was again introduced into the liquid inlet of the plate-and-frame filter to carry out a second top blowing, such that the water washing liquid in the filter cake was replaced;

(6) the mixed liquid consisting of the first material liquid, the lactate permeate liquid, the lactate residual liquid and the water washing liquid was subjected to a downstream treatment so as to obtain a lactate S2.

Example 5.3

(1) 1,000 L of lactate fermentation broth and 30 g of perlite were injected into a mixing tank with a stirring device in a separation unit, then subjected to stirring and mixing at the temperature of 30° C. and the rotation speed of 20 rpm until the perlite was completely suspended in the fermentation broth to obtain a mixed material;

(2) The mixed material was poured into a plate-and-frame filter by a booster pump, and subjected to filtering under the condition of stirring and a pressure of 0.4 MPa until the mixed material was completely filtered, and the booster pump was turned off, such that a first feed liquid and a filter cake were obtained, wherein the mesh number of filter cloth in the plate-and-frame filter was 1,000 meshes;

(3) After the filtering process was finished, the compressed air with a pressure of 0.25 MPa was introduced into a liquid inlet of the plate-and-frame filter in order to blow out lactate permeation liquid remained in the filter cake from the top until the blown-out liquid was very little and only a small amount of liquid foam was entrained in the compressed air, the first top blowing was stopped;

(4) After the first top blowing was finished, water was poured into a liquid inlet of the plate-and-frame filter until the water flow at an outlet was continuous, an inlet valve and an outlet valve were closed, a soaking process was performed for 90 min, a lactate residual liquid in the thallus cells was obtained after the soaking process with water was completed;

(5) Following completion of the water washing process, the compressed air with a pressure of 0.25 MPa was again introduced into the liquid inlet of the plate-and-frame filter to carry out a second top blowing, such that the water washing liquid in the filter cake was replaced;

(6) the mixed liquid consisting of the first material liquid, the lactate permeate liquid, the lactate residual liquid and the water washing liquid was subjected to a downstream treatment so as to obtain a lactate S3.

Example 5.4

(1) 1,000 L of lactate fermentation broth and 60 g of perlite were injected into a mixing tank with a stirring device in a separation unit, then subjected to stirring and mixing at the temperature of 0° C. and the rotation speed of 100 rpm until the perlite was completely suspended in the fermentation broth to obtain a mixed material;

(2) The mixed material was poured into a plate-and-frame filter by a booster pump, and subjected to filtering under the condition of stirring and a pressure of 0.35 MPa until the mixed material was completely filtered, and the booster pump was turned off, such that a first feed liquid and a filter cake were obtained, wherein the mesh number of filter cloth in the plate-and-frame filter was 600 meshes;

(3) After the filtering process was finished, the compressed air with a pressure of 0.1 MPa was introduced into a liquid inlet of the plate-and-frame filter in order to blow out lactate permeation liquid remained in the filter cake from the top until the blown-out liquid was very little and only a small amount of liquid foam was entrained in the compressed air, the first top blowing was stopped;

(4) After the first top blowing was finished, water was poured into a liquid inlet of the plate-and-frame filter until the water flow at an outlet was continuous, an inlet valve and an outlet valve were closed, a soaking process was performed for 60 min, a lactate residual liquid in the thallus cells was obtained after the soaking process with water was completed;

(5) Following completion of the water washing process, the compressed air with a pressure of 0.05 MPa was again introduced into the liquid inlet of the plate-and-frame filter to carry out a second top blowing, such that the water washing liquid in the filter cake was replaced;

(6) the mixed liquid consisting of the first material liquid, the lactate permeate liquid, the lactate residual liquid and the water washing liquid was subjected to a downstream treatment so as to obtain a lactate S1.

Example 5.5

(1) 1,000 L of lactate fermentation broth and 100 g of perlite were injected into a mixing tank with a stirring device in a separation unit, then subjected to stirring and mixing at the temperature of 40° C. and the rotation speed of 20 rpm until the perlite was completely suspended in the fermentation broth to obtain a mixed material;

(2) The mixed material was poured into a plate-and-frame filter by a booster pump, and subjected to filtering under the condition of stirring and a pressure of 0.05 MPa until the mixed material was completely filtered, and the booster pump was turned off, such that a first feed liquid and a filter cake were obtained, wherein the mesh number of filter cloth in the plate-and-frame filter was 800 meshes;

(3) After the filtering process was finished, the compressed air with a pressure of 0.05 MPa was introduced into a liquid inlet of the plate-and-frame filter in order to blow out lactate permeation liquid remained in the filter cake from the top until the blown-out liquid was very little and only a small amount of liquid foam was entrained in the compressed air, the first top blowing was stopped;

(4) After the first top blowing was finished, water was poured into a liquid inlet of the plate-and-frame filter until the water flow at an outlet was continuous, an inlet valve and an outlet valve were closed, a soaking process was performed for 120 min, a lactate residual liquid in the thallus cells was obtained after the soaking process with water was completed;

(5) Following completion of the water washing process, the compressed air with a pressure of 0.05 MPa was again introduced into the liquid inlet of the plate-and-frame filter to carry out a second top blowing, such that the water washing liquid in the filter cake was replaced;

(6) the mixed liquid consisting of the first material liquid, the lactate permeate liquid, the lactate residual liquid and the water washing liquid was subjected to a downstream treatment so as to obtain a lactate S5.

Example 5.6

(1) 1,000 L of lactate fermentation broth and 5 g of perlite were injected into a mixing tank with a stirring device in a separation unit, then subjected to stirring and mixing at the temperature of 10° C. and the rotation speed of 50 rpm until the perlite was completely suspended in the fermentation broth to obtain a mixed material;

(2) The mixed material was poured into a plate-and-frame filter by a booster pump, and subjected to filtering under the condition of stirring and a pressure of 0.45 MPa until the mixed material was completely filtered, and the booster pump was turned off, such that a first feed liquid and a filter cake were obtained, wherein the mesh number of filter cloth in the plate-and-frame filter was 500 meshes;

(3) After the filtering process was finished, the compressed air with a pressure of 0.3 MPa was introduced into a liquid inlet of the plate-and-frame filter in order to blow out lactate permeation liquid remained in the filter cake from the top until the blown-out liquid was very little and only a small amount of liquid foam was entrained in the compressed air, the first top blowing was stopped;

(4) After the first top blowing was finished, water was poured into a liquid inlet of the plate-and-frame filter until the water flow at an outlet was continuous, an inlet valve and an outlet valve were closed, a soaking process was performed for 30 min, a lactate residual liquid in the thallus cells was obtained after the soaking process with water was completed;

(5) Following completion of the water washing process, the compressed air with a pressure of 0.3 MPa was again introduced into the liquid inlet of the plate-and-frame filter to carry out a second top blowing, such that the water washing liquid in the filter cake was replaced;

(6) the mixed liquid consisting of the first material liquid, the lactate permeate liquid, the lactate residual liquid and the water washing liquid was subjected to a downstream treatment so as to obtain a lactate S6.

Comparative Example 5.1

The lactate was separated according to the method of CN104557515A, the centrifugation was carried out to replace the gas cap water wash of the Example 5.1, and the centrifugal clear liquid was subjected to a downstream treatment so as to obtain a lactate D1.

Comparative Example 5.2

The lactate was separated according to the method of CN104557515A, the centrifugation was carried out to replace the gas cap water wash of the Example 5.1, the solid phase after centrifugation was washed with equal volumes of water for twice, the water washing liquid and the centrifugal clear liquid were mixed and then subjected to a downstream treatment so as to obtain a lactate D2.

Comparative Example 5.3

The lactate was separated according to the method of Example 5.1, the steps (3)-(5) were eliminated, the filtrate obtained from step (2) was directly subjected to a downstream treatment so as to obtain a lactate D3.

Comparative Example 5.4

The lactate was separated according to the method of Example 5.1, the steps (3) and (5) were eliminated, the filtrate obtained from step (2) and the filter cake washing liquid obtained in the step (4) were directly subjected to a downstream treatment so as to obtain a lactate D4.

TABLE 2

| | Liquid subjected to downstream treatment | | Lactate yield, |
|---|---|---|---|
| | Volume/L | Lactate content/g · mL$^{-1}$ | % |
| Lactate fermentation broth | 1000 | 150 | 100 |
| Example 5.1 | 1200 | 118 | 94 |
| Example 5.2 | 1230 | 115 | 96 |
| Example 5.3 | 1280 | 109 | 93 |
| Example 5.4 | 1280 | 110 | 94 |
| Example 5.5 | 1290 | 108 | 93 |
| Example 5.6 | 1290 | 108 | 93 |
| Comparative Example 5.1 | 1220 | 98 | 80 |
| Comparative Example 5.2 | 1450 | 89 | 86 |
| Comparative Example 5.3 | 840 | 149 | 84 |
| Comparative Example 5.4 | 1550 | 86 | 89 |

As can be seen from the results of Table 2, when compared with the Comparative Examples 5.1-5.2, the method provided by the present disclosure has higher lactate content and lactate yield; the Comparative Example 5.3 does not carry out gas cap water washing, although the lactate content is similar to that of the fermentation broth, the lactate yield is only 84%; the Comparative Example 5.4 does not perform the gas top blowing, and only carry out the water washing process, although the lactic yield is close to 89%, but the solution was too dilute and the lactate content was low. Therefore, as compared with Comparative Examples 5.1-5.4, the method for separating lactate provided by the present disclosure has higher separation effect and lower cost in the industrialized process.

Examples 6.1 to 6.12 and Comparative Examples 6.1 to 6.5

The examples are used for illustrating the polylactic acid prepared by the apparatus and method of the present disclosure. Wherein, (1) The color and lustre of the polylactic acid (PLA) slice was the most visual indicator for reflecting the quality of the PLA slice, and influenced the color of downstream products to a certain extent. The color and luster was a general term for lustre (degree of extinction) and color (degree of yellowness), and was a reflection of reflected light in terms of spatial distribution, spectral distribution and directionality. The color and lustre was measured by the principle of colorimetry and photometry and the International Commission on illumination (or Commission Internationale De L'Eclairage, or "CIE" for abbreviation in French) measurement standard, and was usually measured by a hunter (L, a, b) colorimeter, and the results are expressed by L value, a value and b value. The L value represented whiteness, the higher was the L value, the higher were the brightness and the whiteness; when the a value was large, it indicated a large red color index; when the b value was large, it indicated a large yellow color index. The color and lustre parameters were measured by a CM-5 spectrocolorimeter, wherein the CM-5 spectrocolorimeter was purchased from Konika Minolta Co., Ltd. in Japan;

(2) The monomer content of the polylactic acid slices was detected by using a gas chromatograph GC580, wherein the gas chromatograph GC580 was purchased from Perkin Elmer Incorporation, USA;

(3) Mechanical property measurement

In the present disclosure, the tensile strength and the elongation at break were tested by an intelligent electronic tensile testing machine, the instrument with the model number XLW was purchased from the Jinan Labthink Electromechanical Technology Co., Ltd.

(4) Weight average molecular weight

In the present disclosure, the weight average molecular weight was measured by using a gel permeation chromatograph (GPC).

(5) Source of raw materials

Both the hindered phenol antioxidants and the phosphite ester antioxidants were commercially available from Meryer (Shanghai) Chemical Technology Co., Ltd.

Example 6.1

(1) Lactide melting step: under the protection of continuous nitrogen, lactide was added into a lactide melting tank I and was melted at 95° C. for 1 h to obtain a molten lactide;

(2) First polymerization reaction process: the molten lactide was introduced into a first polymerization reactor II, and a catalyst stannous octoate, a ring-opening polymerization initiator polyethylene glycol and a high-efficiency composite stabilizer CS-12 (the composite stabilizer CS-12 was formed by compounding beta-(3,5-di-tert-butyl-4-hydroxyphenyl) octadecyl propionate (AT-76) and bi-(2,4-di-tert-butylphenyl) pentaerythritol diphosphite (AT-626) according to a mass ratio of 2:1) were added simultaneously, a first polymerization reaction was performed under the conditions consisting of a temperature of 155° C., a pressure of 50 kPa and a reaction time of 3 h, the conversion rate reached 55%.

(3) Second polymerization reaction process: the first melt after the first polymerization reaction was introduced into a second polymerization reactor III, a second polymerization reaction was performed under the conditions consisting of a temperature of 195° C., a pressure of 6 MPa and a reaction time 1 h, the conversion rate reached 95%;

(4) Demonomerization process: the second melt in the second polymerization reactor was introduced into a demonomerization reactor IV, and a terminator phosphorous acid was added to perform a demonomerization reaction under the conditions consisting of the vibration exciter amplitude A=0.15 mm, the vibration frequency f=25 Hz, the temperature of 210° C., the pressure of 1 KPa and the reaction time of 0.5 h, the content of the finally obtained polylactic acid residual lactide monomer was 4.1%;

(5) Pelletizing process: the polylactic acid melt was continuously introduced into a twin-screw extruder V through a melt pipeline and a charging pump, and subjected to water-cooling pelletizing, dehydration, screening, crystallization, dehumidification and drying to finally obtain the polylactic acid resin, wherein the temperature of a pelletizer was 210° C.

Example 6.2

(1) Lactide melting step: under the protection of continuous nitrogen, lactide was added into a lactide melting tank I and was melted at 90° C. for 1 h to obtain a molten lactide;

(2) First polymerization reaction process: the molten lactide was introduced into a first polymerization reactor II, and a catalyst stannous octoate, a ring-opening polymerization initiator polyethylene glycol and a high-efficiency composite stabilizer CS-9 (the composite stabilizer CS-12 was formed by compounding tetra [beta-(3,5-di-tert-butyl-4-hydroxyphenyl) propionic acid] pentaerythritol tetra (alcohol) ester (AT-10) and tri-(2,4-di-tert-butylphenyl) phosphite (AT-168) according to a mass ratio of 2:1) were added simultaneously, a first polymerization reaction was performed under the conditions consisting of a temperature of 150° C., a pressure of 50 kPa and a reaction time of 3 h, the conversion rate reached 95%.

(3) Second polymerization reaction process: the first melt after the first polymerization reaction was introduced into a second polymerization reactor III, a second polymerization reaction was performed under the conditions consisting of a temperature of 190° C., a pressure of 6 MPa and a reaction time 1 h, the conversion rate reached 95%;

(4) Demonomerization process: the second melt in the second polymerization reactor was introduced into a demonomerization reactor IV, and a terminator phosphorous acid was added to perform a demonomerization reaction under the conditions consisting of the vibration exciter amplitude A=0.25 mm, the vibration frequency f=30 Hz, the temperature of 215° C., the pressure of 1 KPa, and the reaction time of 0.5 h, the content of the finally obtained polylactic acid residual lactide monomer was 0.8%;

(5) Pelletizing process: the polylactic acid melt was continuously introduced into a twin-screw extruder V through a melt pipeline and a charging pump, and subjected to water-cooling pelletizing, dehydration, screening, crystallization, dehumidification and drying to finally obtain the polylactic acid resin, wherein the temperature of a pelletizer was 205° C.

Examples 6.3 to 6.12

Polylactic acid was prepared according to the same apparatus and method as in example 6.1, except that: the composite stabilizer CS1-12 was replaced, and the conditions in step (d) were modified, the conditions for preparation are shown in Table 3, and the test results are shown in Table 4.

Comparative Example 6.1

The conventional PLA slices were used, which had the weight average molecular weight of 150,000, the melt index of 6 g/10 min, the L value 75.15, the a value −1.13, the b value 19.08 of the color and lustre, and the monomer content of 5.2%.

Comparative Example 6.2

The polylactic acid was prepared with the same apparatus and method as in Example 6.1, except that the composite stabilizer CS1-12 was replaced with D-2, which was prepared by compounding AT-76 and AT-626 according to the mass ratio of 1:3, the test results were shown in Table 4.

Comparative Example 6.3

The polylactic acid was prepared with the same apparatus and method as in Example 6.1, except that in the step (4), the vibration exciter had an amplitude A=0 mm and the vibration frequency f=0 Hz, the test results were shown in Table 4.

Comparative Example 6.4

The polylactic acid was prepared with the same apparatus and method as in Example 6.1, except that the step (3) was not performed, the test results were shown in Table 4.

Comparative Example 6.5

The polylactic acid was prepared with the same apparatus and method as in Example 6.1, except that the mass ratio of the used amounts of the lactide, the catalyst, the high-efficiency composite stabilizer, the initiator and the terminator was 1:0.006:0.003:0.007:0.006, the test results were shown in Table 4.

TABLE 3

| Sample name | Composite stabilizer | Electromagnetic vibration exciter | |
| --- | --- | --- | --- |
| | | Amplitude A (mm) | Vibration frequency f (Hz) |
| Comparative Example 6.1 | — | — | — |
| Comparative Example 6.2 | D-2 | — | — |
| Comparative Example 6.3 | CS-12 | 0 | 0 |
| Comparative Example 6.4 | CS-9 | 0 | 0 |
| Comparative Example 6.5 | CS-9 | 0 | 0 |
| Example 6.1 | CS-12 | 0.15 | 25 |
| Example 6.2 | CS-9 | 0.15 | 20 |
| Example 6.3 | CS-1 | 0.15 | 30 |
| Example 6.4 | CS-2 | 0.20 | 35 |
| Example 6.5 | CS-3 | 0.20 | 40 |
| Example 6.6 | CS-4 | 0.25 | 45 |
| Example 6.7 | CS-5 | 0.25 | 20 |
| Example 6.8 | CS-6 | 0.3 | 20 |
| Example 6.9 | CS-7 | 0.3 | 25 |
| Example 6.10 | CS-8 | 0.3 | 30 |
| Example 6.11 | CS-10 | 0.15 | 35 |
| Example 6.12 | CS-11 | 0.15 | 40 |

Test Example 1

The samples of Examples 6.1-6.12 and Comparative Examples 6.1-6.5 were taken, and the color values were measured by using a CM-5 spectrocolorimeter, the test results were shown in Table 4, wherein the Table 4 illustrated the color values of the PLA slices and the content of residual lactide monomer.

Test Example 2

The samples of Examples 6.1-6.12 and Comparative Examples 6.1-6.5 were taken, and the content of the polylactic acid slice monomers was measured by using a gas chromatograph GC580, and the test results were shown in Table 4.

TABLE 4

| Sample name | Monomer content (%) | Color values | | |
| --- | --- | --- | --- | --- |
| | | L value | a value | b value |
| Comparative Example 6.1 | 5.2 | 75.15 | −1.13 | 19.08 |
| Comparative Example 6.2 | 4.2 | 76.18 | −1.36 | 21.24 |
| Comparative Example 6.3 | 4.1 | 78.19 | −1.46 | 18.16 |
| Comparative Example 6.4 | 4.2 | 75.15 | −1.33 | 4.49 |
| Comparative Example 6.5 | 4.3 | 75.23 | −1.13 | 4.25 |
| Example 6.1 | 4.1 | 72.63 | −1.20 | 6.32 |
| Example 6.2 | 0.8 | 75.13 | −1.03 | 4.19 |
| Example 6.3 | 4.0 | 70.15 | −1.72 | 16.97 |
| Example 6.4 | 3.7 | 70.32 | −1.43 | 17.65 |
| Example 6.5 | 3.2 | 69.82 | −1.06 | 14.37 |
| Example 6.6 | 2.9 | 68.95 | −1.28 | 13.02 |
| Example 6.7 | 2.5 | 70.65 | −1.31 | 7.34 |
| Example 6.8 | 1.7 | 71.54 | −1.46 | 9.16 |
| Example 6.9 | 1.1 | 70.95 | −1.29 | 8.23 |
| Example 6.10 | 2.1 | 72.78 | −1.16 | 6.06 |
| Example 6.11 | 2.3 | 70.25 | −1.29 | 11.05 |
| Example 6.12 | 1.2 | 73.20 | −1.14 | 5.86 |

As can be seen from Table 4:

(1) Based on the data comparison between the color values of PLA slices prepared from PLA polymerization processes in Examples 6.1-6.12 using different composite stabilizers and the color values of PLA slices prepared in Comparative Example 6.1 using the existing conventional PLA slices and the PLA slices prepared in Comparative Examples 6.2-6.5, Wherein the existing conventional PLA slice of the Comparative Example 6.1 has the L value 75.15 and the b value 19.08; however, the PLA slices of the Comparative Examples 6.2 to 6.5 exhibit high b value and large yellowness, the reason may be that the conditions defined in the technical solution of the present disclosure are not used in the PLA polymerization process.

In Examples 6.1 to 6.12, the b value of the PLA slice is significantly reduced after the composite stabilizer is added, which demonstrates that the polymerization reaction has higher thermal stability and thermal oxidation resistance after addition of the composite stabilizer, so that the PLA slice with desirable color index can be obtained. Moreover, as can be seen from Table 4, the b value of the PLA slice obtained from Example 6.2 by adding the composite stabilizer CS-9 is merely 4.19, the effect is the best.

(2) As can be seen from the comparison between the monomer content in the polylactic acid prepared in Examples 6.1 to 6.12 and the monomer content in the polylactic acid prepared in Comparative Example 6.1 using the existing conventional PLA slices and the polylactic acid prepared in Comparative Examples 6.2-6.5:

Wherein the content of residual lactide monomer in the PLA slice in Comparative Example 6.1 is 5.2%;

Wherein the content of residual lactide monomer in the PLA slice in Comparative Example 6.2 is 4.2%;

Wherein the demonomerization process in the Comparative Example 6.3, the electromagnetic vibration exciter has an amplitude A=0 mm, and a vibration frequency f=0 Hz, and the content of the residual lactide monomer in the PLA slice is 4.1%;

Wherein the content of residual lactide monomer in the PLA slice in Comparative Examples 6.4-6.5 is within a range of 4.2-4.3%;

Wherein the demonomerization process in the Examples 6.1-6.12, the electromagnetic vibration exciter has an amplitude A=0.15-0.30 mm, and a vibration frequency f=20-45 Hz, and the content of the residual lactide monomer in the PLA slices has a minimum 0.8%.

Therefore, the results of Examples 6.1 to 6.12 demonstrate that the introduction of the vibration force field can increase the shear rate of the polylactic acid melt, thus the melt interface stretches and compresses so as to generate the corresponding oscillation, increase the volatilization amount of lactide monomer, meet the requirement of rapidly removing monomers, and control the content of the lactide monomer in the residual polylactic acid melt to the minimum.

Examples 7.1 to 7.7 and Comparative Examples 7.1 to 7.6

The examples were provided to illustrate the apparatus and method for online preparation of the modified polylactic acid material from polylactic acid melt according to the present disclosure. Wherein:

(1) Mechanical property measurement

In the present disclosure, the tensile strength and the elongation at break are tested by an intelligent electronic tensile testing machine, and the instrument with the model number XLW was purchased from the Jinan Labthink Electromechanical Technology Co., Ltd.

(2) Weight average molecular weight

In the present disclosure, the weight average molecular weight was measured by using a gel permeation chromatograph.

(3) Source of raw materials

The polybutylene adipate terephthalate was purchased from Xinjiang Blue Ridge Tunghe Chemical Industry Joint Stock Co., Ltd.;

The polypropylene carbonate was purchased from the Inner Mongolia Mengxi High-tech New Material Joint Stock Co., Ltd.;

The polybutylene succinate was purchased from the BASF SE;

The polytetramethylene glycol-succinic acid/adipic acid copolyester was purchased from the Kingfa science and technology Co., Ltd.;

The talc was purchased from Shanghai Chengzhi Chemical Products Co., Ltd.; The calcium carbonate was purchased from Zhejiang Tianshi Nanometer Science and Technology Co., Ltd.;

The tributyl citrate was purchased from Meryer (Shanghai) Chemical Technology Co., Ltd.;

The epoxidized soybean oil was purchased from Dongguan Hengtai Chemical Co., Ltd.;

The adipic acid diethylene glycol monobutylether ester was purchased from Changchun Institute of Applied Chemistry (CIAC);

The chain extenders were purchased from the BASF SE;

The crosslinking agent was purchased from Dongguan Huanzong Trade Co., Ltd.;

The antioxidant was purchased from Tianjin Rainlon New Materials Co., Ltd.;

The lubricant was purchased from the Sichuan Tianyu Oil Chemical Co., Ltd.

Example 7.1

This example aimed to illustrate a modified polylactic acid material prepared with the device and method of the present disclosure.

As shown in FIG. 8:

(a) 59.1 parts by weight of polymerized polylactic acid melt were continuously output via the polylactic acid melt pipeline and fed into a polylactic acid melt feedstock metering pump 10C (hereinafter referred to as "melt feedstock metering pump"), and subsequently continuously output and fed into Zone IV of the twin-screw extruder;

(b) 35 parts by weight of a first solid modifier polybutylene adipate terephthalate and 5 parts by weight of a second solid modifier talc were respectively added into a first solid modifier hopper 8c and a second solid modifier hopper 9c;

(c) 0.3 part by weight of liquid modifier tributyl citrate was passed through a liquid feedstock metering pump 12c and fed into a zone II of the twin-screw extruder in a lateral feeding mode;

(d) 0.1 part by weight of chain extender, 0.1 part by weight of cross-linking agent, 0.2 part by weight of antioxidant and 0.2 part by weight of lubricant were uniformly mixed and then added into an auxiliary material hopper 6c, and 100 parts by weight of the prepared modified polylactic acid polymerization melt was uniformly blended in zones V to XI of a twin-screw extruder and then extruded and granulated.

The modified polylactic acid material was prepared as a consequence.

Example 7.2

This example aimed to illustrate a modified polylactic acid material prepared with the device and method of the present disclosure.

(a) 53 parts by weight of polymerized polylactic acid melt were continuously output via the polylactic acid melt pipeline 15 and fed into a polylactic acid melt feedstock metering pump 10c (hereinafter referred to as "melt feedstock metering pump"), and subsequently continuously output and fed into Zone IV of the twin-screw extruder;

(b) 39 parts by weight of a first solid modifier polybutylene adipate terephthalate and 7 parts by weight of a second solid modifier talc were respectively added into a first solid modifier hopper 8c and a second solid modifier hopper 9c;

(c) 0.2 part by weight of liquid modifier epoxidized soybean oil was passed through a liquid feedstock metering pump 12c and fed into a zone II of the twin-screw extruder in a lateral feeding mode;

(d) 0.2 part by weight of chain extender, 0.1 part by weight of cross-linking agent, 0.3 part by weight of antioxidant and 0.2 part by weight of lubricant were uniformly mixed and then added into an auxiliary material hopper 6c, and 100 parts by weight of the prepared modified polylactic acid polymerization melt was uniformly blended in zones V to XI of a twin-screw extruder and then extruded and granulated.

The modified polylactic acid material was prepared as a consequence.

Examples 7.3 to 7.7

The modified polylactic acid material was prepared with the same device and method as in Example 7.1, except for that the first solid modifier, the second solid modifier, the liquid modifier, the chain extender, the crosslinking agent, the antioxidant and the lubricant in Example 7.1 were altered accordingly, as specifically shown in Table 5.

TABLE 5

| No. | Polylactic acid melt (part by weight) | First solid modifier (part by weight) | Second solid modifier (part by weight) | Liquid modifier (part by weight) | Chain extender (part by weight) | Crosslinking agent (part by weight) | Antioxidant (part by weight) | Lubricant (part by weight) |
| --- | --- | --- | --- | --- | --- | --- | --- | --- |
| | To prepare 100 parts by weight of a modified polylactic acid polymerization melt | | | | | | | |
| Example 7.3 | 66.3 | 25 Polypropylene carbonate | 5 Talc | 0.3 Epoxidized soybean oil | 0.1 | 0.1 | 0.2 | 0.3 |
| Example 7.4 | 64 | 25 Polybutylene succinate | 7 Talc | 0.3 Adipic acid diethylene glycol monobutylether ester (DGBEA) | 0.15 | 0.15 | 0.3 | 0.4 |
| Example 7.5 | 66.8 | 25 Polybutylene glycol-succinic acid/adipic acid copolyester | 5 Talc | 0.3 Tributyl citrate | 0.2 | 0.1 | 0.2 | 0.2 |
| Example 7.6 | 64.1 | 30 Polypropylene carbonate | 3 Calcium carbonate | 0.3 Tributyl citrate | 0.1 | 0.2 | 0.3 | 0.3 |
| Example 7.7 | 57.3 | 35 Polybutylene succinate | 5 Calcium carbonate | 0.3 Epoxidized soybean oil | 0.1 | 0.2 | 0.2 | 0.2 |

Comparative Example 7.1

The modified polylactic acid material was prepared according to the same method as in Example 7.2, except for that the blown film grade polylactic acid chips manufactured by the COFCO were used, and according to the formula of Example 7.2, 53 parts by weight of polylactic acid chips were mechanically mixed with 39 parts by weight of polybutylene adipate terephthalate, 7 parts by weight of talc, 0.2 parts by weight of epoxidized soybean oil, 0.2 parts by weight of chain extender, 0.1 part by weight of cross-linking agent, 0.3 part by weight of antioxidant, and 0.2 part by weight of lubricant, and then extruded by a twin-screw extruder for granulation.

The modified polylactic acid material was prepared as a consequence.

Comparative Examples 7.2 to 7.6

The modified polylactic acid material was prepared with the same device and method as in Example 7.1, except for that the content of the polylactic acid melt and the content of the first solid modifier and the second solid modifier were different, as shown in Table 6.

TABLE 6

| Unit (part by weight) | Polylactic acid melt | First solid modifier | Second solid modifier | Liquid modifier | Chain extender | Crosslinking agent | Antioxidant | Lubricant |
|---|---|---|---|---|---|---|---|---|
| | | | To prepare 100 parts by weight of a modified polylactic acid polymerization melt | | | | | |
| Comparative Example 7.2 | 80.0 | 17 Polypropylene carbonate | 2 Talc | 0.3 Epoxidized soybean oil | 0.1 | 0.1 | 0.2 | 0.3 |
| Comparative Example 7.3 | 82.0 | 15 Polybutylene succinate | 1 Talc | 0.1 Adipic acid diethylene glycol monobutyl-ether ester | 0.4 | 0.4 | 0.6 | 0.5 |
| Comparative Example 7.4 | 51.0 | 40 Polybutylene glycol-succinic acid/adipic acid copolyester | 8 Talc | 0.3 Tributyl citrate | 0.2 | 0.1 | 0.2 | 0.2 |
| Comparative Example 7.5 | 46.2 | 36 Polypropylene carbonate | 9 Calcium carbonate | 0.3 Tributyl citrate | 0.1 | 0.2 | 0.3 | 0.3 |
| Comparative Example 7.6 | 80.4 | 15 Polybutylene succinate | 2 Calcium carbonate | 0.6 Epoxidized soybean oil | 0.5 | 0.5 | 0.5 | 0.5 |

Test Example 3

The modified polylactic acid materials prepared in Examples 7.1-7.7 and Comparative Examples 7.1-7.6 were subjected to tests of tensile strength and elongation at break, and the results were shown in Table 7.

TABLE 7

| Samples | Weight average molecular weight (g/mol) | Tensile strength (MPa) | Elongation at break (%) | Production cost (yuan/ton) |
|---|---|---|---|---|
| Comparative Example 7.1 | 154,059 | 45.0 | 98 | 4,600 |
| Comparative Example 7.2 | 178,265 | 46.8 | 108 | 3,100 |
| Comparative Example 7.3 | 178,398 | 50.2 | 103 | 3,100 |
| Comparative Example 7.4 | 179,115 | 51.9 | 105 | 3,100 |
| Comparative Example 7.5 | 178,855 | 50.6 | 99 | 3,100 |
| Comparative Example 7.6 | 179,065 | 52.0 | 100 | 3,100 |
| Example 7.1 | 179,174 | 55.0 | 120 | 3,100 |
| Example 7.2 | 184,059 | 56.2 | 125 | 3,100 |
| Example 7.3 | 180,243 | 54.8 | 118 | 3,100 |
| Example 7.4 | 183,224 | 53.1 | 109 | 3,100 |
| Example 7.5 | 179,986 | 52.9 | 121 | 3,100 |
| Example 7.6 | 183,054 | 56.0 | 120 | 3,100 |
| Example 7.7 | 181,752 | 52.3 | 119 | 3,100 |

As can be seen from the results in Table 7, the polylactic acid modified materials prepared in Examples 7.1-7.7 of the present disclosure have superior properties, wherein the polylactic acid modified material prepared in Example 7.2 of the present disclosure has excellent properties, namely the molecular weight is 184,059 g/mol, the tensile strength is 56.2 MPa, and the elongation at break is 125%.

Examples 8.1 to 8.2 and Comparative Example 8.1

The examples were provided to illustrate the polylactic acid devolatilization evaporator according to the present disclosure.

Example 8.1

A polylactic acid/lactide material with a conversion rate of 94.6% obtained from lactide by a melt polymerization method was passed through a devolatilization apparatus as shown in FIG. 9 at a flow rate of 10 kg/h so as to remove the residual monomers.

In the Example, the clearance between the outer edge of the stirring belt 6 and the inner wall of the cylinder body 3 was 25 mm, the screw pitch of the stirring belt 6 was 0.5 times of the inner diameter of the cylinder body 3, the width of the stirring belt 6 is 0.075 times of the inner diameter of the cylinder body 3, the rotation speed of the stirring shaft 5 was 15 r/min, the temperature of the steam introduced into the clamp ferrule 4 was 200° C., the absolute pressure in the evaporator was 8 kPa.

The measured content of monomers in the polylactic acid slice at the discharge port of the film evaporator was 0.16 wt %.

Example 8.2

A polylactic acid/lactide material with a conversion rate of 95.8% obtained from lactide by a melt polymerization method was passed through a devolatilization apparatus as shown in FIG. 10 at a flow rate of 10 kg/h so as to remove the residual monomers.

In the Example, the clearance between the outer edge of the stirring belt 6 and the inner wall of the cylinder body 3 was 5 mm, the screw pitch of the stirring belt 6 was 0.75 times of the inner diameter of the cylinder body 3, the width of the stirring belt 6 is 0.06 times of the inner diameter of the cylinder body 3, the rotation speed of the stirring shaft 5 was 45 r/min, the temperature of the steam introduced into the clamp ferrule 4 was 220° C., the absolute pressure in the evaporator was 2 KPa.

The measured content of monomers in the polylactic acid slice at the discharge port of the film evaporator was 0.09 wt %.

Comparative Example 8.1

A polylactic acid/lactide material with a conversion rate of 95.2% obtained from lactide by a melt polymerization method was passed through a devolatilization apparatus provided by the Chinese utility model patent CN 204932896 U at a flow rate of 10 kg/h so as to remove the residual monomers.

In the Comparative Example, the clearance between the inner wall of the cylinder body and the scraper outside the stirring shaft was 5 mm. Under the operating conditions that the rotation speed of the stirring shaft was 30 r/min, the temperature of the heat conduction oil introduced into the clamp ferrule was 200° C. and the absolute pressure in the evaporator was 5 kPa, the measured content of the monomers in the polylactic acid slice at the discharge port of the film evaporator was 0.32 wt %; when the rotation speed of the stirring shaft was increased to 45 r/min, the temperature of the heat conduction oil introduced into the clamp ferrule 4 was raised to 220° C., and the absolute pressure in the evaporator was reduced to 2 kPa, a lot of polylactic acid material was adhered to a scraper of the evaporator to form hangs on the wall, such that the system cannot normally operate.

As can be seen from the comparison between Examples 8.1-8.2 and Comparative Example 8.1, the devolatilization of polylactic acid/lactide can be performed by using the devolatilization device provided by the present disclosure, so as to reduce the monomer content in polylactic acid to 0.2 wt % or even below 0.1 wt %, the technical effect is significantly superior to the prior art.

Examples 9.1 to 9.5

The examples served to illustrate the preparation method of lactide according to the present disclosure.

The lactic acid raw material was subjected to preheating, primary concentration, secondary concentration, pre-condensation polymerization, condensation polymerization, and depolymerization (stannous octoate was used as a catalyst) respectively, so as to carry out the continuous production of lactide, wherein the conditions in each stage were shown in Table 8, the yield and optical purity of the finally obtained lactide were shown in Table 9.

TABLE 8

| | | Example 9.1 | Example 9.2 | Example 9.3 | Example 9.4 | Example 9.5 |
|---|---|---|---|---|---|---|
| Secondary concentration | Preheat temperature (° C.) | 90 | 100 | 105 | 110 | 120 |
| | Pressure (kPa) | 50 | 45 | 30 | 25 | 20 |
| Primary concentration | Preheat temperature (° C.) | 90 | 100 | 105 | 110 | 120 |
| | Pressure (kPa) | 50 | 45 | 20 | 25 | 30 |
| | Water content (wt %) | <1 | <1 | <1 | <1 | <1 |
| Pre-condensation polymerization | Temperature (° C.) | 140 | 145 | 150 | 155 | 160 |
| | Pressure (kPa) | 30 | 25 | 20 | 15 | 10 |
| | Time (h) | 0.5 | 2 | 1.2 | 1 | 1.5 |
| | Polymerization degree | 2-3 | 2-3 | 2-3 | 2-3 | 2-3 |
| Condensation polymerization | Temperature (° C.) | 165 | 160 | 180 | 175 | 170 |
| | Pressure (kPa) | 6 | 8 | 5 | 4 | 3 |
| Depolymerization | Temperature (° C.) | 210 | 200 | 195 | 190 | 185 |
| | Pressure (kPa) | 5 | 4 | 2 | 3 | 1 |

TABLE 9

| Example No. | Lactate yield (%) | Optical purity of lactide (D content %) | Whether or not the metal ions in the product are detected |
|---|---|---|---|
| Example 9.1 | 91.2 | ~5 | Not |
| Example 9.2 | 92.3 | ~4 | Not |
| Example 9.3 | 93.5 | ~4 | Not |
| Example 9.4 | 94.8 | ~3 | Not |
| Example 9.5 | 95.7 | ~3 | Not |

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

What is claimed:
1. A method for producing polylactic acid, comprising:
   (i) inoculating a lactic acid fermentation strain into a lactic acid fermentation culture medium to perform a fermentation, so as to obtain a fermentation broth containing lactate;
   (ii) separating the fermentation broth to obtain a lactic acid;
   (iii) synthesizing a polymer-grade lactide by using the lactic acid as a raw material;

(iv) subjecting the polymer-grade lactide to a polymerization reaction in a polymerization reaction device to obtain a polylactic acid, wherein the polymerization reaction device comprises:
a polymerization reactor comprising a flow channel; and
a stirring component disposed in the flow channel of the polymerization reactor, wherein:
the stirring component includes a magnetic induction element, an electromagnetic winding mechanism, and a gap formed between the electromagnetic winding mechanism and the magnetic induction element,
the electromagnetic winding mechanism is disposed around the magnetic induction element and encircles an inner wall of the polymerization reactor, and
thread grooves formed on the magnetic induction element, wherein
the magnetic induction element and the electromagnetic winding mechanism can generate an electromagnetic induction, thereby allowing the magnetic induction element to autorotate around its axis which is collinear with an axis of the polymerization reactor, and
the polymer-grade lactide is configured to pass through the gap and be stirred by the magnetic induction element.

2. The method of claim 1, wherein the lactic acid fermentation strain is selected from *Lactobacillus rhamnosus* under accession number CGMCC No. 19507, *Lactobacillus rhamnosus* under accession number CGMCC No. 19508, *Lactobacillus rhamnosus* under accession number CGMCC No. 16834, *Pediococcus acidilactici* under accession number CGMCC No. 16833 or *Lactobacillus plantarum* under accession number CGMCC No. 16835.

3. The method of claim 1, wherein the fermentation is performed under a stirring condition, the stirring device used for stirring comprises a stirring paddle body and a brush type strip arranged to hang down from the stirring paddle body, such that the brush type strip is rotatable along with the rotation of the stirring paddle body and contacts with the bottom of a lactic acid fermentation tank, and the precipitate at the bottom of the lactic acid fermentation tank is swept and stirred by the brush type strip.

4. The method of claim 1, wherein the lactic acid fermentation strain is inoculated into the lactic acid fermentation culture medium to perform the fermentation by inoculating *Lactobacillus plantarum* into a fermentation culture medium to perform a lactic acid fermentation, wherein at least a part of a carbon source in the fermentation culture medium is provided by starch sugar.

5. The method of claim 1, wherein the lactic acid fermentation strain is inoculated into the lactic acid fermentation culture medium to perform the fermentation by inoculating *Pediococcus acidilactici* into a fermentation culture medium, then introducing oxygen-containing gas into a fermentation system for pre-fermentation until the concentration of the *Pediococcus acidilactici* in the fermentation system reaches $OD_{600}$=8-13; and subsequently stopping introduction of the oxygen-containing gas, and continuing the fermentation process until the consumption of the five-carbon sugar in the fermentation system reaches 45-55 wt %, wherein before inoculation, the fermentation culture medium contains 30-100 g/L glucose and 15-45 g/L five-carbon sugar, and the ventilation amount of the oxygen-containing gas is 0.005-0.05 vvm in terms of oxygen.

6. The method of claim 1, wherein the method for obtaining lactic acid by separating the fermentation broth comprises:

(A) subjecting the fermentation broth containing lactate and a filter aid to mixing and solid-liquid separation sequentially to obtain a first feed liquid and a filter cake;
(B) carrying out gas cap washing treatment in regard to the filter cake to obtain a second feed liquid;
(C) performing downstream treatment in regard to the mixed solution of the first feed liquid and the second feed liquid so as to prepare the lactic acid;
wherein the lactate is selected from ammonium lactate and/or sodium lactate.

7. The method of claim 1, wherein the method for obtaining lactic acid by separating the fermentation broth comprises:
(1) subjecting the fermentation broth containing lactic acid to an ion exchange to obtain a lactic acid solution;
(2) carrying out vacuum concentration in regard to the lactic acid solution to obtain a lactic acid concentrated solution;
(3) performing molecular distillation of the lactic acid concentrated solution so as to prepare a refined lactic acid;
wherein the content of lactic acid in the fermentation broth is within a range of 5-30 wt %.

8. The method of claim 1, further comprising synthesizing polylactic acid from lactide in an air-isolated manner using a continuous feeding system, wherein the continuous feeding system comprises a raw material bag/box and a raw material collector for collecting and outputting lactide, wherein the raw material bag/box is connected with an inert gas input pipeline, a discharge pipe is movably inserted into the raw material bag/box, a cyclone separator is connected with the downstream of the discharge pipe, and a solid matter outlet of the cyclone separator is connected with the raw material collector.

9. The method of claim 1, further comprising removing residual monomers of the polymerization reaction using a polylactic acid devolatilization evaporator, wherein the polylactic acid devolatilization evaporator comprises:
a container including a circular tube-shaped cylinder body that extends vertically;
a stirring shaft which is at least partially disposed in the cylinder body and coaxial with the cylinder body;
a stirring belt which is connected to the stirring shaft and disposed in a spiral shape around a central axis of the cylinder body, the stirring belt includes an outer belt surface facing an inner circumferential surface of the cylinder body, and the outer belt surface is spaced apart from the inner circumferential surface of the cylinder body for each other.

10. The method of claim 1, wherein the method for synthesizing a polymer grade lactide from a lactic acid comprises:
(1) subjecting the lactic acid to a pre-condensation polymerization reaction under a first polymerization condition to obtain a lactic acid prepolymer with a polymerization degree less than 5 and a gas phase containing lactic acid;
(2) subjecting the lactic acid prepolymer to a condensation polymerization reaction in a falling-film reactor under a second polymerization condition to obtain a lactic acid oligomer with a polymerization degree less than 10;
(3) depolymerizing the lactic acid oligomer under the action of a catalyst to obtain a lactide-containing product.

11. The method of claim 1, wherein the polymer-grade lactide is configured to pass through the gap and further perform periodic axial pulsation.

12. The method of claim 1, wherein the polymerization reaction device further comprises a main shaft rod on which the magnetic induction element is sleeved.

13. The method of claim 1, wherein the magnetic induction element comprises a main body portion that is cylindrical and a tip portion that is tapered, both sequentially arranged along the flow direction of the polymer-grade lactide.

14. The method of claim 1, wherein the polymerization reaction device further comprises an outer wall and a heat exchange liquid circulation cavity formed between the outer wall and the inner shell.

15. The method of claim 14, wherein the polymerization reaction device further comprises a circulation pipe fitting, a static mixer, and a circulation pump, and the polymer-grade lactide flows between the flow channel of the polymerization reactor and the circulating pipe fitting while passing through at least the static mixer and the gap.

16. The method of claim 1, wherein the electromagnetic winding mechanism is kept between a power-on state and then a power-off state.

\* \* \* \* \*